(12) United States Patent
Balagadde et al.

(10) Patent No.: US 7,407,799 B2
(45) Date of Patent: Aug. 5, 2008

(54) MICROFLUIDIC CHEMOSTAT

(75) Inventors: Frederick Balagadde, Pasadena, CA (US); Carl L. Hansen, Pasadena, CA (US); Emil Kartalov, Pasadena, CA (US); Stephen R. Quake, Stanford, CA (US)

(73) Assignee: California Institute of Technology, Pasadena, CA (US)

( * ) Notice: Subject to any disclaimer, the term of this patent is extended or adjusted under 35 U.S.C. 154(b) by 344 days.

(21) Appl. No.: 11/012,852

(22) Filed: Dec. 14, 2004

(65) Prior Publication Data

US 2005/0164376 A1   Jul. 28, 2005

Related U.S. Application Data

(60) Provisional application No. 60/536,863, filed on Jan. 16, 2004.

(51) Int. Cl.
  *C12P 19/04*   (2006.01)
  *C12M 1/00*   (2006.01)
(52) U.S. Cl. .................................. 435/289.1
(58) Field of Classification Search .............. 435/288.5, 435/289.1, 294.1, 297.1, 293.1, 304.2, 306.1
  See application file for complete search history.

(56) References Cited

U.S. PATENT DOCUMENTS

| | | |
|---|---|---|
| 3,570,515 A | 3/1971 | Kinner |
| 3,747,628 A | 7/1973 | Holster et al. |
| 4,046,159 A | 9/1977 | Pegourie |
| 4,119,368 A | 10/1978 | Yamakazi |
| 4,153,855 A | 5/1979 | Feingold |
| 4,245,673 A | 1/1981 | Bouteille et al. |
| 4,434,704 A | 3/1984 | Surjaatmadja |
| 4,898,582 A | 2/1990 | Faste |
| 4,992,312 A | 2/1991 | Frisch |
| 5,085,562 A | 2/1992 | Van Lintel |
| 5,088,515 A | 2/1992 | Kamen |
| 5,096,388 A | 3/1992 | Weinberg |
| 5,126,115 A | 6/1992 | Fujita et al. |
| 5,164,558 A | 11/1992 | Huff et al. |
| 5,171,132 A | 12/1992 | Miyazaki |
| 5,224,843 A | 7/1993 | Van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,423,287 A | 6/1995 | Usami et al. |
| 5,529,465 A | 6/1996 | Zengerle et al. |
| 5,593,130 A | 1/1997 | Hansson et al. |
| 5,595,650 A | 1/1997 | Manz |
| 5,642,015 A | 6/1997 | Whitehead et al. |
| 5,659,171 A | 8/1997 | Young et al. |
| 5,660,370 A | 8/1997 | Webster |
| 5,681,024 A | 10/1997 | Lisec et al. |
| 5,705,018 A | 1/1998 | Hartley |
| 5,759,014 A | 6/1998 | Van Lintel |
| 5,775,371 A | 7/1998 | Pan et al. |
| 5,779,868 A | 7/1998 | Parce et al. |
| 5,788,468 A | 8/1998 | Dewa et al. |
| 5,836,750 A | 11/1998 | Cabuz |
| 5,842,787 A | 12/1998 | Kopf-Sill et al. |
| 5,875,817 A | 3/1999 | Carter |
| 5,876,187 A | 3/1999 | Forster et al. |
| 5,932,799 A | 8/1999 | Moles |
| 5,942,443 A | 8/1999 | Parce et al. |
| RE36,350 E | 10/1999 | Swedberg et al. |
| 6,007,309 A | 12/1999 | Hartley |
| 6,043,080 A | 3/2000 | Lipshutz et al. |
| 6,054,277 A * | 4/2000 | Furcht et al. .................. 435/6 |
| 6,107,044 A | 8/2000 | Nikiforov |

(Continued)

FOREIGN PATENT DOCUMENTS

EP   0 592 094 A2   4/1994

(Continued)

OTHER PUBLICATIONS

"Biochips," Nature Biotechnology, vol. 18, Supplement 2000, pp. IT43-IT44, 2000.
"Chapter 9: Microfluidic Devices," Micromachined Transducers Sourcebook, pp. 779-882, 1998.
"Electro Microfluidic Dual In-Line Package (EMDIP)," Sandia National Laboratories, 2 pages, no date.
"Last Chance For Micromachines," The Economist Technology Quarterly, printed from website http://www.economist.com/science/displayStory.cfm?Story_ID=442930 on Jan. 25, 2001, 8 pages, Dec. 7, 2000.
"The Liver Chip," Technology Review, pp. 64-67, Mar. 2003.
Ahn, Chong H. et al., "Fluid Micropumps Based On Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

(Continued)

*Primary Examiner*—Jon P Weber
*Assistant Examiner*—Kailash C Srivastava
(74) *Attorney, Agent, or Firm*—Townsend and Townsend and Crew LLP

(57) ABSTRACT

A chemostat is described that includes a growth chamber having a plurality of compartments. Each of the compartments may be fluidly isolated from the rest of the growth chamber by one or more actuatable valves. The chemostat may also include a nutrient supply-line to supply growth medium to the growth chamber, and an output port to remove fluids from the growth chamber. Also, a method of preventing biofilm formation in a growth chamber of a chemostat is described. The method may include the steps of adding a lysis agent to a isolated portion of the growth chamber, and reuniting the isolated portion with the rest of the growth chamber.

15 Claims, 38 Drawing Sheets

U.S. PATENT DOCUMENTS

| | | | |
|---|---|---|---|
| 6,123,769 | A | 9/2000 | Sanjoh |
| 6,155,282 | A | 12/2000 | Zachary et al. |
| 6,174,365 | B1 | 1/2001 | Sanjoh |
| 6,296,673 | B1 | 10/2001 | Santarsiero et al. |
| 6,345,502 | B1 | 2/2002 | Tai et al. |
| 6,408,878 | B2 | 6/2002 | Unger et al. |
| 6,409,832 | B2 | 6/2002 | Weigl et al. |
| 6,508,988 | B1 | 1/2003 | Van Dam et al. |
| 6,509,188 | B1* | 1/2003 | Trosch et al. ............ 435/292.1 |
| 6,581,441 | B1 | 6/2003 | Paul |
| 6,596,545 | B1 | 7/2003 | Wagner et al. |
| 6,599,736 | B2* | 7/2003 | McCaskill et al. ....... 435/288.5 |
| 6,627,076 | B2 | 9/2003 | Griffiths |
| 6,653,124 | B1* | 11/2003 | Freeman ................ 435/297.1 |
| 6,662,818 | B2 | 12/2003 | Paul et al. |
| 6,664,104 | B2 | 12/2003 | Pourahmadi et al. |
| 6,677,131 | B2 | 1/2004 | Yuen |
| 6,716,620 | B2* | 4/2004 | Bashir et al. ............ 435/287.2 |
| 6,752,922 | B2 | 6/2004 | Huang et al. |
| 6,767,706 | B2 | 7/2004 | Quake et al. |
| 2001/0027745 | A1 | 10/2001 | Weigl et al. |
| 2002/0037499 | A1 | 3/2002 | Quake et al. |
| 2002/0145231 | A1 | 10/2002 | Quake et al. |
| 2002/0158022 | A1 | 10/2002 | Huang et al. |
| 2002/0164816 | A1 | 11/2002 | Quake et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/09595 A2 | 2/2001 |
| WO | WO 01/09595 A3 | 2/2001 |
| WO | WO 02/60582 A2 | 8/2002 |
| WO | WO 03/037781 A1 | 5/2003 |

OTHER PUBLICATIONS

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. MIcro Electro Mech. Syst. Tech. Digest, vol. 12, pp. 222-227, 1999.

Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.

Black, Harvey, "Tiny Technology Promises Tremendous Profits," The Scientist, vol. 15, No. 21, 4 pages, Oct. 29, 2001.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brechtel, R. et al., "Control Of The Electroosmotic Flow By Metal-Salt-Containing Buffers," Journal of Chromatography A, vol. 716, pp. 97-105, 1995.

Bryzek, Janusz et al., "Micromachines On The March", IEEE Spectrum, vol. 31, No. 5, pp. 20-31, May 1994.

Buchaillot, Lionel et al., "Silicon Nitride Thin Films Young's Modulus Determination By An Optical Non Destructive Method," Jpn. J. Appl. Phys., vol. 36, Part 2, No. 6B, pp. L794-L797, Jun. 15, 1997.

Calkins, Kathryn, "Mycometrix: Rubber Chips," BioCentury, 2 pages, Oct. 16, 2000.

Chang, Jun Keun et al., "Functional Integration Of Serial Dilution And Capillary Electrophoresis On A PDMS Microchip," Biotechnology and Bioprocess Engineering, vol. 8, No. 4, pp. 233-239, 2003.

Chen, Chihchen et al., "Gray-Scale Photolithography Using Microfluidic Photomasks," PNAS, vol. 100, No. 4, pp. 1499-1504, Feb. 18, 2003.

Chiu, Daniel T. et al., "Patterned Deposition Of Cells And Proteins Onto Surfaces By Using Three-Dimensional Microfluidic Systems," PNAS, vol. 97, No. 6, pp. 2408-2413; Mar. 14, 2000.

Chou, Hou-Pu et al., "A Microfabricated Device For Sizing And Sorting DNA Molecules," Proc. Natl. Acad. Sci., vol. 96, pp. 11-13, Jan. 1999.

Chou, Hou-Pu et al., "A Microfabricated Rotary Pump," Biomedical Microdevices, vol. 3, No. 4, pp. 323-330, 2001.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Cowen, S. et al., "An On-Chip Miniature Liquid Chromatography System: Design, Construction And Characterization," Micro Total Analysis Systems, Proceedings of the μTAS '94 Workshop, University of Twente, The Netherlands, pp. 2 cover pages and 295-298, 1995.

Delamarche, Emmanuel et al., "Patterned Delivery Of Immunoglobulins To Surfaces Using Microfluidic Networks," Science, vol. 276, pp. 779-781, May 2, 1997.

Duffy, David C. et al., "Patterning Electroluminescent Materials With Feature Sizes As Small As 5μm Using Elastomeric Membranes As Masks For Dry Lift-Off," Advanced Materials, vol. 11, No. 7, pp. 546-552, 1999.

Duffy, David C. et al., "Rapid Prototyping Of Microfluidic Switches In Poly(dimethyl siloxane) And Their Actuation By Electro-Osmotic Flow," J. Micromech. Microeng., vol. 9, pp. 211-217, 1999.

Duffy, David C. et al., "Rapid Prototyping Of Microfluidic Systems In Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis On Flexible Silicone Microdevices: Analysis Of DNA Restriction Fragments And Detection Of Single DNA Molecules On Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Eyal, Shulamit et al., "Velocity-Independent Microfluidic Flow Cytometry," Electrophoresis, vol. 23, pp. 2653-2657, 2002.

Fahrenberg, J. et al., "A Microvalve System Fabricated By Thermoplastic Molding," J. Micromech. Microeng., vol. 5, pp. 169-171, 1995.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Fitzgerald, Deborah A., "Making Every Nanoliter Count," The Scientist, vol. 15, No. 21, 8 pages, Oct. 29, 2001.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical And Fluidic Packaging Of Surface Micromachined Electro-Microfluidic Devices," 8 pages, no date.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Garno, Jayne C. et al., "Production Of Periodic Arrays Of Protein Nanostructures Using Particle Lithography," Langmuir, vol. 18, No. 21, pp. 8186-8192, 2002.

Gass, V. et al., "Integrated Flow-Regulated Silicon Micropump," Sensors and Actuators A, vol. 43, pp. 335-338, 1994.

Geng, Xindu et al., "Retention Model For Proteins In Reversed-Phase Liquid Chromatography," Journal of Chromatography, vol. 296, pp. 15-30, 1984.

Gerlach, Torsten, "Pumping Gases By A Silicon Micro Pump With Dynamic Passive Valves," Transducers '97, 1997 International Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics—A Review," J. Micromech. Microeng., vol. 3, pp. 168-192, 1993.

Greene, Chana, "Characterizing The Properties Of PDMS," pp. 1-11, Summer 2000.

Grover, William H. et al., "Monolithic Membrane Valves And Diaphragm Pumps For Practical Large-Scale Integration Into Glass Microfluidic Devices," Sensors and Actuators B, vol. 89, pp. 315-323, 2003.

Guérin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Hansen, Carl. L. et al., "A Robust And Scalable Microfluidic Metering Method That Allows Protein Crystal Growth By Free Interface Diffusion," PNAS, vol. 99, No. 26, pp. 16531-16536, Dec. 24, 2002.

Hansen, Carl. L. et al., "Systematic Investigation Of Protein-Phase Behavior With A Microfluidic Formulator," PNAS Early Edition, 6 pages, 2004.

Harrison, D. Jed et al., "Integration Of Analytical Systems Incorporating Chemical Reactions And Electrophoretic Separation," Micro Total Analysis Systems, Proceedings of the μTAS '94 Workshop, University of Twente, The Netherlands, pp. 2 cover pages and 105-115, 1995.

Harrison, D. Jed et al., "Micromachining A Miniaturized Capillary Electrophoresis-Based Chemical Analysis System On A Chip," Science, vol. 261, pp. 895-897, Aug. 13, 1993.

Hicks, Jennifer, "Genetics And Drug Discovery Dominate Microarray Research," R&D Magazine, pp. 28-33, Feb. 1999.

Hofmann, Oliver et al., "Modular Approach To Fabrication Of Three-Dimensional Microchannel Systems In PDMS—Application To Sheath Flow Microchips," Lab on a Chip, vol. 1, pp. 108-114, 2001.

Hong, Jong Wook et al., "A Nanoliter-Scale Nucleic Acid Processor With Parallel Architecture," Nature Biotechnology, vol. 22, No. 4, pp. 1-5, Apr. 2004.

Horn, Howard, "Lab Chips Sector: Microtechnologies Are Changing Healthcare And More," Life Sciences, pp. 19-21, Mar. 20, 2001.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting. Optical Society of America, vol. 8, Postconference Edition, A215, pp. 107-110, Jun. 15-17, 1988.

Hosokawa, Kazuo et al., "A Microfluidic Device For Mixing Of Capillary-Drive Liquids," IEEJ Trans. SM, vol. 123, No. 1, pp. 23-24, 2003.

Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct. 15, 1999.

Ikuta, Koji et al., "Three Dimensional Micro Integrated Fluid Systems (MIFS) Fabricated By Stereo Lithography," IEEE, pp. 1-6, 1994.

Jacobson, Stephen C. et al., "High-Speed Separations On A Microchip," Analytical Chemistry, vol. 66, No. 7, pp. 1114-1118, Apr. 1, 1994.

Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.

Jacobson, Stephen C. et al., "Open Channel Electrochromatography On A Microchip," Analytical Chemistry, vol. 66, No. 14, pp. 2369-2373, Jul. 15, 1994.

Jerman, Hal, "Electrically-Activated, Normally-Closed Diaphragm Valves," Transducers '91, 1991 International Conference on Solid-State Sensors and Actuators, pp. cover, 1045-1048, 1991.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Jung, D. R. et al., "Chemical And Physical Interactions At Metal/Self-Assembled Organic Monolayer Interfaces," pp. 1-54, 1994.

Kagan, C. R., "Organic-Inorganic Hybrid Materials As Semiconducting Channels In Thin-Film Field-Effect Transistors," Science, vol. 286, pp. 945-947, Oct. 29, 1999.

Kamentsky, Louis A. et al., "Spectrophotometer: New Instrument For Ultrarapid Cell Analysis," Science, vol. 150, pp. 630-631, Oct. 29, 1965.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluidic Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. Ed-25, No. 10, pp. 1257-1260, Oct. 1978.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Fully Integrated PCR-Capillary Electrophoresis Microsystem For DNA Analysis," Lab On A Chip, vol. 1, pp. 102-107, 2001.

Lagally, Eric T. et al., "Monolithic Integrated Microfluidic DNA Amplification And Capillary Electrophoresis Analysis System," Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Lin, L. Y. et al., "Free-Space Micromachined Optical Switches For Optical Networking," IEEE Journal of Selected Topics in Quantum Electronics, vol. 5, No. 1, pp. 4-9, Jan. 1999.

Liu, Jian et al., "A Nanoliter Rotary Device For Polymerase Chain Reaction," Electrophoresis, vol. 23, pp. 1531-1536, 2002.

Lötters, J C et al., "The Mechanical Properties Of The Rubber Elastic Polymer Polydimethylsiloxane For Sensor Applications," J. Micromech. Microeng., vol. 7, pp. 145-147, 1997.

Lucy, Charles A. et al., "Characterization Of The Cationic Surfactant Induced Reversal Of Electroosmotic Flow In Capillary Electrophoresis," Anal. Chem., vol. 68, pp. 300-305, 1996.

Maluf, N., "An Introduction To Microelectromechanical Systems Engineering," Artech House Publishers, Boston London, pp. 42-45, Dec. 1999.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, Sid, "Fundamental Changes Ahead For Lab Instrumentation," R&D Magazine, 5 pages, Feb. 1999.

Marsili, Ray, "Lab-On-A-Chip Poised to Revolutionize Sample Prep," R&D Magazine, 5 pages, Feb. 1999.

Mastrangelo, C. H. et al., "Vacuum-Sealed Silicon Micromachined Incandescent Light Source," IEDM, pp. 503-506, 1989.

McDonald, J. Cooper et al., "Fabrication Of Microfluidic Systems In Poly(dimethylsiloxane)," Electrophoresis, vol. 21, pp. 27-40, 2000.

McDonald, J. Cooper et al., "Poly(dimethylsiloxane) As A Material For Fabricating Microfluidic Devices," Accounts of Chemical Research, vol. 35, No. 7, pp. 491-499, 2002.

Muller, Richard S. et al., "Surface-Micromachined Microoptical Elements And Systems," Proceedings of the IEEE, vol. 86, No. 8, pp. 1705-1720, Aug. 1998.

Ng, Jessamine M. K. et al., "Components For Integrated Poly(Dimethylsiloxane) Microfluidic Systems," Electrophoresis, vol. 23, pp. 3461-3473, 2002.

Oleschuk, Richard D. et al., "Analytical Microdevices For Mass Spectrometry," Trends In Analytical Chemistry, vol. 19, No. 6., pp. 379-388, 2000.

Olsson, Anders et al., "Simulation Studies Of Diffuser And Nozzle Elements For Valve-Less Micropumps," Transducers '97, 1997 International Conference on Solid-State Sensors and Actuators, Chicago, Illinois, pp. 1039-1042, Jun. 16-19, 1997.

Pethig, Ronald et al., "Applications Of Dielectrophoresis In Biotechnology," Tibtech, vol. 15, pp. 426-432, Oct. 1997.

Qin, Dong et al., "Elastomeric Light Valves," Adv. Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen R. et al., "From Micro- To Nanofabrication With Soft Materials," Science, vol. 290, pp. 1536-1540, Nov. 24, 2000.

Rapp, R. et al., "LIGA Micropump For Gases And Liquids," Sensors and Actuators A, vol. 40, pp. 57-61, Jan. 1994.

Roylance, Lynn Michelle et al., "A Batch-Fabricated Silicon Accelerometer," IEEE Transactions on Electron Devices, vol. ED-26, No. 12, pp. 1911-1917, Dec. 1979.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping And Development Of Microfluidic And BioMEMS Devices," IVD Technology, 12 pages, Jun. 2002.

Schasfoort, Richard B. M. et al., "Field-Effect Flow Control For Microfabricated Fluidic Networks," Science, vol. 286, pp. 942-945, Oct. 29, 1999.

Schueller, Oliver J. A. et al., "Fabrication Of Glassy Carbon Microstructures By Soft Lithography," Sensors and Actuators A, vol. 72, pp. 126-139, 1999.

Shoji, Shuichi, "Fluids For Sensor Systems," Topics in Current Chemistry, vol. 194, pp. 167-188, 1998.

Shoji, Shuichi et al., "Smallest Dead Volume Microvalves For Integrated Chemical Analyzing Systems," Transducers '91, 1991 International Conference on Solid-State Sensors and Actuators, San Francisco, California, pp. cover, 1052-1055, 1991.

Sklar, Larry A. et al., Sample Handling For Kinetics And Molecular Assembly In Flow Cytometry, SPIE, vol. 3256, pp. 144-153, 1998.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One By One," PNAS, vol. 97, No. 20, pp. 10687-10690, Sep. 26, 2000.

Swart, Remco et al., "Recent Progress In Open Tubular Liquid Chromatography," Trends in Analytical Chemistry, vol. 16, No. 6, pp. 332-342, 1997+A326.

Tawfik, Dan S. et al., "Man-Made Cell-Like Compartments For Molecular Evolution," Nature Biotechnology, vol. 16, pp. 652-656, Jul. 1998.

Terry, Stephen C. et al., "A Gas Chromatographic Air Analyzer Fabricated On A Silicon Wafer," IEEE Transactions on Electron Devices, vol. ED-26, pp. 1880-1886, Dec. 1979.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Vahey, Paul G. et al., "Development Of A Positive Pressure Driven Micro-Fabricated Liquid Chromatographic Analyzer Through Rapid-Prototyping With Poly(dimethylsiloxane) Optimizing Chromatographic Efficiency With Sub-Nanoliter Injections," Talanta, vol. 51, pp. 1205-1212, 2000.

Van De Pol, F.C.M. et al., "A Thermo-Pneumatic Actuation Principle For A Microminiature Pump And Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the μTAS '94 Workshop, University of Twente, The Netherlands, 17 pages, Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Van Der Woerd, Mark et al., "The Promise Of Macromolecular Crystallization In Microfluidic Chips," Journal of Structural Biology, vol. 142, pp. 180-187, 2003.

Velev, Orlin D., "On-Chip Manipulation Of Free Droplets," Nature, vol. 426, pp. 515-516, Dec. 4, 2003.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vieider, Christian et al., "A Pneumatically Actuated Micro Valve With A Silicon Rubber Membrane For Integration With Fluid Handling Systems," Transducers '95, 8th International Conference on Solid-State Sensors and Actuators and Eurosensors IX, Stockholm, Sweden, pp. 284-286, Jun. 25-29, 1995.

Washizu, Masao et al., "Molecular Dielectrophoresis Of Biopolymers," IEEE Transactions on Industry Applications, vol. 30, No. 4, pp. 835-843, Jul. 1994.

Webster, J. R. et al., "Monolithic Capillary Gel Electrophoresis Stage With On-Chip Detector," IEEE, pp. 491-496, 1996.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Wilbur, James L. et al., "Lithographic Molding: A Convenient Route To Structures With Sub-Micrometer Dimensions," Adv. Mater., vol. 7, pp. 649-652, 1995.

Wu, Hongkai et al., "Fabrication Of Complex Three-Dimensional Microchannel Systems In PDMS," J. Am. Chem. Soc., vol. 125, No. 2, pp. 554-559, 2003.

Xia, Younan et al., "Complex Optical Surfaces Formed By Replica Molding Against Elastomeric Masters," Science, vol. 273, pp. 347-349, Jul. 19, 1996.

Xia, Younan et al., "Micromolding Of Polymers In Capillaries: Applications In Microfabrication," Chem. Mater., vol. 8, No. 7, 1559-1566, 1996.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures By Soft Lithography," Adv. Mater., vol. 11, No. 14, pp. 1186-1189, 1999.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves For Microfluidic Network Integration," Journal of Biomechanical Engineering, vol. 121, pp. 2-6, Feb. 1999.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhao, Zhan, et al., "An Integrated Biochip Design And Fabrication," Proceedings of SPIE, vol. 4936, pp. 321-326, 2002.

Zheng, Bo et al., "A Droplet-Based, Composite PDMS/Glass Capillary Microfluidic System For Evaluating Protein Crystallization Conditions By Microbatch And Vapor-Diffusion Methods With On-Chip X-Ray Diffraction," Angew. Chem., pp. 1-4, 2004.

Novick, A. et al., "Description of the Chemostat," Science, 1950, 112, 715-716.

Rotman, B., A Simplified Device for Continuous Growth of Microorganisms, Journal of Bacteriology, 1955, 70, 485-486.

Spicer, C.C., "The Theory of Bacterial Constant Growth Apparatus," Biometrics, 1955, 11, 225-230.

Herbert, D. et al., "The Continuous Culture of Bacteria: a Theoretical and Experimental Study," Journal of General Microbiology, 1956, 14, 601-622.

Herbert, D., "Continuous Culture of Bacteria," Journal of General Microbiology, 1956, 15, R4.

Herbert, D., "Continuous Fermentation," Chemistry & Industry, 1958, 381.

DeLisa, M.P. et al., "Mapping Stress-Induced Changes in Autoinducer Al-2 Production in Chemostat-Cultivated Escherichia coli K-12," Journal of Bacteriology 2001, 183, 2918-2928.

Jannasch, H.W. et al., "Experimental Bacterial Ecology Studied in Continuous Culture," Advances in Microbial Physiology eds. Rose A,H. & Tempest D.W. (Academic Press, London), 1974, 11, 165-212.

Maresova H. et al., "A Chemostat Culture as a Tool for the Improvement of a Recombinant E. coli Strain Over-Producing Penicillin G Acylase," Biotechnoloy and Bioengineering, 2001, 75, 46-52.

Nielson, J., et al., Bioreaction Engineering Principles, 2d ed., (Kluwer Academic/Plenum Publishers, New York), 2003, pp. 42-45.

Wiebe, M.G. et al., "Evolution of a Recombinant (Gucoamylase-Producing) Strain of Fusarium venenatum A3/5 in Chemostat Culture," Biotechnology and Bioengineering, 2001, 73, 146-156.

Novick, A. et al., "Experiments with the Chemostat on Spontaneous Mutations of Bacteria," Proceedings of the National Academy of Sciences of the United States of America, 1950, 36, 708-719.

Lane, P.G. et al., "Analysis of a Continuous-Culture Technique for the Selection of Mutants Tolerant to Extreme Environmental Stress," Biotechnology and Bioengineering, 1999,65, 397-406.

Qu, M.B. et al., Toxicity and Biodegradation Formaldehyde in Anaerobic Methanogenic Culture, Biotechnology and Bioengineering, 1997,55,727-736.

Hancock, R.E.W, "A Brief on Bacterial Biofilms," Nature Genetics, 2001, 29, 360.

Costerton, J.W., et al., "Microbial Biofilms," Annual Review of Microbiology, 1995, 49, 711-745.

Lawrence, J.R., et al., "Optical Sectioning of Microbial Biofilms," Journal of Bacteriology, 1991, 173, 6558-6567.

Blanch, H.W. et al., Biochemical Engineering (Marcel Dekker, Inc., New York), 1996, pp. 305.

Ingraham, J.L. et al., "Measurements of Growth," in Growth of the Bacterial Cell (Sinauer Associates, Inc., Sunderland), p. 230, 1983.

Yokobayashi, Y. et al., "Evolutionary Design of Genetic Circuits and Cell-Cell Communications," Advances in Complex Systems, 2003, 6, 37-45.

Unger, M.A., et al., "Monolithic Microfabricated Valves and Pumps by Multilayer Soft Lithography," Science, 2000, 288, 113-116.

Thorsen, T., "Microfluidic Large-Scale Integration," Science, 2002, 298, 580-584.

Monod, J., "The Growth of Bacterial Cultures," Annual Reviews of Microbiology, 1949, 3, 371-394.

Shuler, M.L. et al., "How Cells Grow," Bioprocess Engineering: Basic Concepts, 2d ed., (Prentice Hall PTR, Upper Saddle River, NJ), pp. 155-200. , 2002.

Heo, J. et al. A Microfluidic Bioreactor Based on Hydrogel-Entrapped E.coli: Cell Viability, Lysis and Intracellular Enzyme Reactions Analytical Chemistry. Jan. 1, 2003, vol. 75, No. 1, pp. 22-26.

Taylor et al. Multifluidic, Multicompartment Device for Neuroscience Research. Langmuir, Dec. 4, 2002, vol. 19, 2003. pp. 1551-1556.

Khoo, Melvin et al., "A Novel Micromachined Magnetic Membrane Microfluid Pump," pp. 1-4, 2000.

Kirk-Othmer, "Concise Encyclopedia of Chemical Technology," John Wiley & Sons, 5 pages, 1985.

* cited by examiner

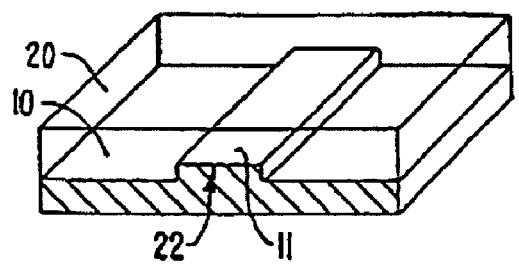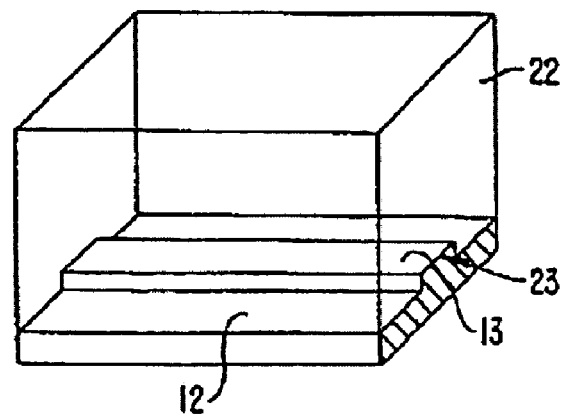
FIG. 8    FIG. 9
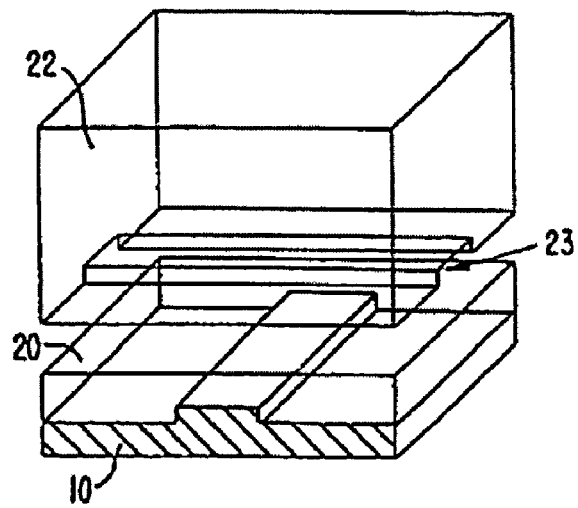
FIG. 10
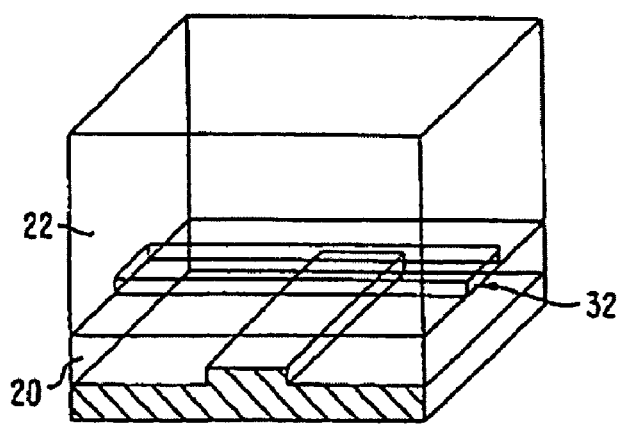
FIG. 11

MICROFLUIDIC CHEMOSTAT

CROSS-REFERENCES TO RELATED APPLICATIONS

This application claims the benefit of U.S. Provisional Application No. 60/536,863, filed Jan. 16, 2004, entitled "MICROFLUIDIC CHEMOSTAT" the entire contents of which are herein incorporated by this reference.

STATEMENT AS TO RIGHTS TO INVENTIONS MADE UNDER FEDERALLY SPONSORED RESEARCH OR DEVELOPMENT

This material is based upon work supported by the Defense Advanced Research Projects Agency (Grant No. N66001-02-1-8929), and the National Science Foundation under Grant No. CTS.0088649. The U.S. Government may therefore have certain rights in the invention.

BACKGROUND OF THE INVENTION

The chemical complexity of pharmaceutical proteins makes it difficult to produce them synthetically for medical treatments. For many of these proteins, the only practical production route is to grow bacterial cultures that have been designed to produce the protein in adequate quantities. Thus, pharmaceutical manufacturers, among others, have an active interest in developing devices and methods for the study of bacterial cultures. One technique for measuring the size and growth rate of bacterial cultures involves counting bacteria colonies using plating, which relies on the colony-forming ability of viable cells. A sample of an appropriately diluted culture is dispersed on a solid medium and the number of colonies that form is determined. Unfortunately, plating can produce inexact measurements because the culture continues to grow at an unknown rate during the period of dilution in preparation for plating. In another technique, the total number of cells can be determined microscopically by determining the number of cells per unit area in a counting chamber (a glass slide with a central depression of known depth, whose bottom is ruled into squares of known area). However, this technique is a hands-on, serial process that is prone to human error.

Counting errors may be reduced by using electronic counting devices, such as a coulter counter, which can determine the size distribution as well as the number of bacteria in a sample culture of known volume. The coulter counter relies on a pore, through which a known volume of suspension is pumped. Although the counter is rapid and accurate, it is also expensive and subject to a number of artifactual complications. Moreover, the pore through which the suspension is pumped is prone to clogging if the media and diluents are not carefully prepared.

Another technique for studying and measuring bacterial cultures involves determining the dry weight of cells in a known volume of suspension. This technique is time consuming and requires a considerable amount of sacrificial culture. As such, it is unsuitable for routine monitoring of the growth rate. Optical density has also been used to determine growth rates using cell density. However, the correlation between cell density and optical density of the culture may change during production of proteins that aggregate and form inclusion bodies.

Chemostats may also be used to study and measure bacterial cultures. These devices can maintain a constant population of bacteria in a state of active growth. This may be done by periodically substituting a fraction of a microbial culture with an equal volume of fresh, sterile, chemically defined growth medium. The influent composition may be such that the ingredients are in optimal amounts except for the growth-limiting factor, whose concentration is kept sufficiently low. At an adequate flow rate, a low concentration of the growth-limiting factor establishes itself in the growth chamber.

At sufficiently low concentrations of the growth-limiting factor the microbial growth rate is directly proportional to the concentration of the growth-limiting factor and independent of other nutrient factors, as well as bacterial metabolites. The bacterial population may automatically proceed towards a steady state of growth, where the cell density remains constant and the growth rate is sufficient to replace the cells lost in the effluent. The steady-state cell concentration may be varied by changing the dilution rate, or the concentration of the growth-limiting factor in the influent.

Data collection with conventional chemostats is not easy to automate, which makes studies and measurements of the bacterial cultures labor intensive. The devices also consume large amounts of growth medium that increase the cost of experiments, especially when costly reagents have to be used.

Another difficulty with chemostats is their tendency to form biofilms on growth-chamber walls and probe surfaces. The biofilms can start when microorganisms (e.g., bacteria from the culture) attach to a wall or probe surface during the course of chemostat operation. Once started, the biofilms are difficult to remove and may consume a significant fraction of the substrate. This may compromise the fixed biomass fundamental conservation principle of the chemostat, inducing hybrid batch/chemostat characteristics. The significance of this artifact may be magnified in laboratory scale chemostats where the surface area to volume ratio is large. Thus there remains a need for chemostat technology that suppresses or prevents biofilm growth, and consumes smaller amounts of growth medium, among other characteristics.

BRIEF SUMMARY OF THE INVENTION

Embodiments of the invention include a chemostat. The chemostat may include a growth chamber having a plurality of compartments, where each of the compartments may be fluidly isolated from the rest of the growth chamber by one or more actuatable valves. The chemostat may also include a nutrient supply-line to supply growth medium to the growth chamber, and an output port to remove fluids from the growth chamber.

Embodiments of the invention may also include a chemostat chip. The chemostat chip may include an array of chemostats, where each of the chemostats includes a growth chamber having a plurality of compartments, where each of the compartments may be fluidly isolated from the rest of the growth chamber by one or more actuatable valves. The chemostats may also include a nutrient supply-line to supply growth medium to the growth chamber, and an output port to remove fluids from the growth chamber.

Embodiments of the invention may further include a method of making a chemostat. The method may include the step of forming a flow layer comprising a flow channel, where a growth chamber of the chemostat includes the flow channel. The method may also include coupling the flow layer between a first control layer and a second control layer, where each of the control layers includes one or more control channels that can be actuatued to fluidly isolate a compartment of the flow channel.

Embodiments of the invention may also further include a method of preventing biofilm formation in a growth chamber of a chemostat. The method may include the steps of adding a lysis agent to a isolated portion of the growth chamber, and reuniting the isolated portion with the rest of the growth chamber.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

FIG. 8 is an illustration of a first elastomeric layer formed on top of a micromachined mold;

FIG. 9 is an illustration of a second elastomeric layer formed on top of a micromachined mold;

FIG. 10 is an illustration of the elastomeric layer of FIG. 9 removed from the micromachined mold and positioned over the top of the elastomeric layer of FIG. 8;

FIG. 11 is an illustration corresponding to FIG. 10, but showing the second elastomeric layer positioned on top of the first elastomeric layer.

DETAILED DESCRIPTION OF THE INVENTION

Figure 1:
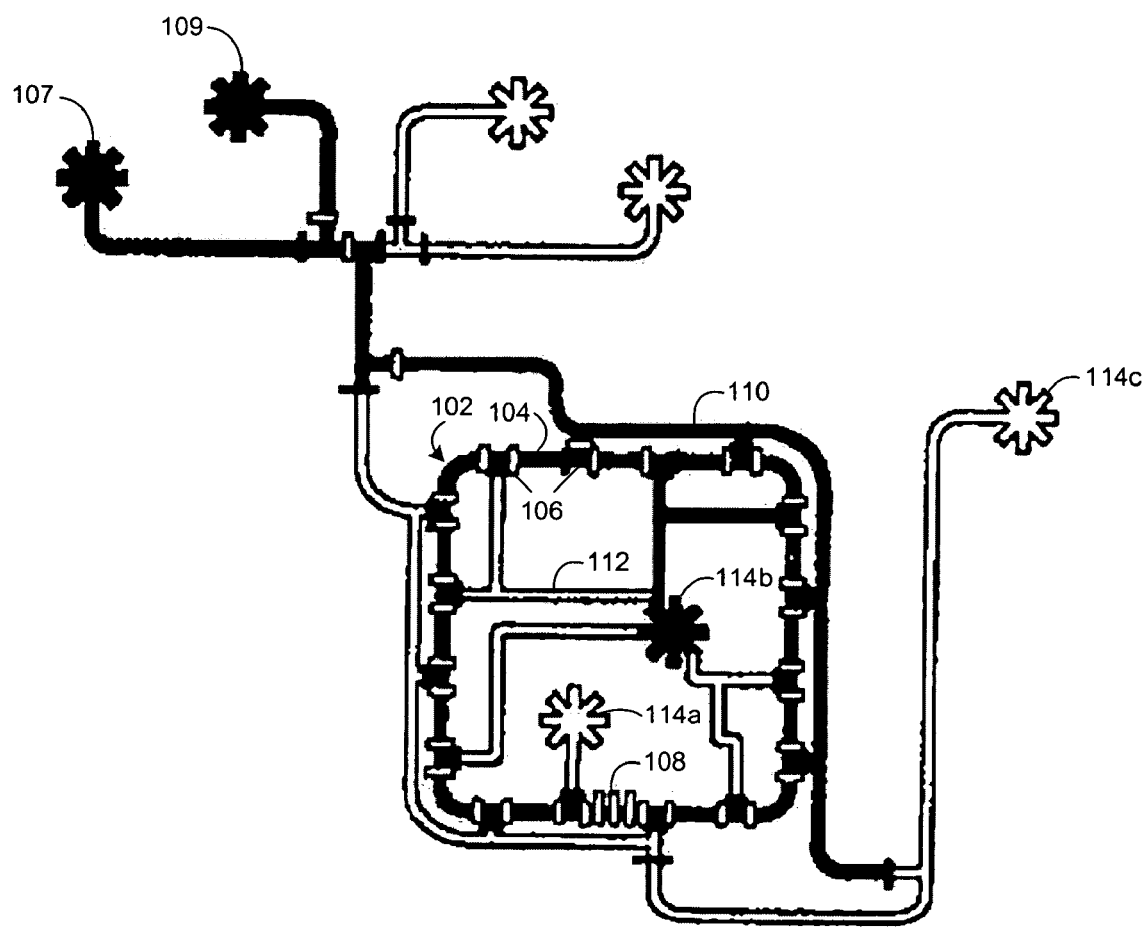
FIG. 1 shows a chemostat according to an embodiment of the invention.

Chemostats of the present invention include microfluidic chemostats having growth chambers divided into two or more compartments. These chemostats can operate with low quantities of growth reagents/medium, which reduces the costs of the chemostat experiments. They may also be operated such that discrete cleaning of the chemostat compartments can occur while an experiment is being conducted, which reduces or prevents the formation of biofilms on the walls of the device.

The small size of the microfluidic chemostats of the invention have high surface area to volume ratio (e.g., about 100 times the surface area to volume ratio of a conventional chemostat). The high ratio permits a larger percentage of the growth chamber surface (e.g., about 55% of the surface or more) to serve as a diffusion interface for the diffusion of gases such as oxygen ($O_2$) and carbon dioxide ($CO_2$). The gas diffusion may be further enhanced by constructing the growth chamber out of materials that have high gaseous permeability (e.g., silicone elastomers such as polydimethylsiloxane (PDMS), which is commercially available as General Electric RTV 615). Using high gaseous permeability materials in the chemostat may help provide a higher level of aeration, which can reduce media acidification and the concentration of toxic metabolites that are attributed to the incomplete oxidation of carbon sources at high cell densities. By reducing the acidity and metabolite concentration of the bacterial growth medium, bacterial cell growth may be less inhibited than in conventional chemostats or batch cultures.

The chemostats of the invention may be operated in a non-continuous mode, such that dilutions may be performed in discrete steps. In a discrete lysing step, one of the compartments is fluidly isolated from the rest of the growth chamber and exposed to a lysis buffer containing a lysing agent that kills the cells in the compartment, including any cells attached to the chamber walls that could grow a biofilm. The lysis buffer may then be removed and fresh growth medium added to the compartment before it rejoins the rest of the growth chamber. Isolating the compartment during the lysing step prevents all the cells in the growth chamber from being exposed to the lysis buffer at once. Instead, the cleaning and dilution that occurs in the discrete lysing step decreases the cell population by a percentage that is about equal to the ratio of the volume of the cleaned chamber to the total volume of the growth chamber. For example, if the growth chamber is divided into 16 equal volume compartments, then cleaning one chamber in a lysing step will dilute the total cell population by 1/16th. Even with a dilution fraction this size or larger, the microfluidic microbial discretized-flow system should reach a steady state.

The chemostats of the present invention may be used in a variety of bacterial culture applications, including the study of bacterial microbes. The studies may include examination and measurement of microbial metabolism, regulatory processes, adaptations and mutations, among others. Studies may also be done on how bacterial microbes respond to changes in their environment. The chemostats can facilitate the characterization of microbial response to changes in specific environmental factors by providing constant environmental conditions for growth and product formation, as well as facilitating the determination of growth conditions that optimize biochemical processes such as pharmaceutical protein production. From such studies, it may be possible to reconstruct the general behavior of microorganisms in their native conditions. The well controlled growth conditions and ability to make in situ optical studies of self sustaining communities of a few thousand bacteria provided by the chemostats of the present invention are also useful for studies of genetic regulatory networks, microbial ecosystems, and artificial biological circuits, among other applications.

The chemostats of the present invention also make it possible to determine as well as maintain growth conditions that enhance the productivity or yield of biochemical processes including, for example, pharmaceutical proteins production, and biochemical biotransformation. The small footprint, parallel architecture, and low reagent consumption of the microfluidic chemostats can make them an efficient tool for high throughput screening applications ranging from chemical genetics to pharmaceutical discovery.

Small-scale inexpensive chemostats that control biofilm growth can facilitate selection-pressure-driven screening of cell populations. The uniform environment in the chemostats subject their microbial population to strong selection pressures, which, because of spontaneous mutations, may result in the appearance of mutants with qualities (e.g., improved growth-rate, nutrient uptake, ability to degrade toxic refractory compounds, etc.) superior to those of their ancestors. The chemostats may also be used for industrial microbial studies to understand the toxicity, carcinogenicity and degradability of complex substrates such as crude hydro-carbons, pesticides and sewage. Kinetic data obtained from such devices would also be scalable to that of large-scale bioreactor experiments, where wall-growth effects are not significant. Additional details of embodiments of chemostats according to the invention will now be described.

Exemplary Chemostat

Referring now to FIG. 1, a chemostat according to an embodiment of the invention is shown. The chemostat includes a growth chamber 102 that includes 16 compartments 104, each of which may be fluidically isolated from rest of the growth chamber 102 by actuatable valves 106. Growth medium may be circulated through the growth chamber 102 with the help of peristaltic pump 108 to keep the growth medium well mixed.

In this embodiment, the growth chamber 102 is a planar loop fluid channel having a total volume on the order of tens of nanoliters (e.g., about 16 nL). The nanoliter volume growth chamber 102 allows the bacterial culture to be monitored in situ by optical microscopy (not shown). This monitoring can provide an automated real time measurement of cell density and morphological properties of the bacterial culture with single cell resolution. The chemostat may be automated to operate autonomously for up to a week or longer, creating a stable steady state bacteria culture having about $10^5$ cells in a reactor volume millions of times smaller than conventional batch reactors, and media consumption of about 40 microliters/day or less. The automated device may include an automated microscope reader (not shown) that provides real-time, non-invasive sampling and documentation of microbial properties, such as the total cell count and cell morphology of the bacterial culture.

As the volume of the growth chamber of a chemostat shrinks, its surface area to volume ratio increases. Consequently, biofilm growth exerts a proportionately larger influence on the kinetics. In the present invention, biofilm growth may be prevented (or suppressed) by segmenting the chemostat into individually addressable compartments that can be periodically cleaned with a lysis buffer to thwart biofilm formation. Preventing biofilm formation (i.e., zero wall-growth) makes possible the basic reduction of chemostat growth equations to an ideal monotone system, simplifying the analysis of chemostat-like behavior.

In the chemostat embodiment shown in FIG. 1, the growth-chamber 102 is composed 16 individually addressable, equal volume compartments 104. One of the compartments 104 may be isolated from the rest of chamber 102 by closing actuatable valves 106. Lysis buffer may be supplied to the compartment 104 through a supply channel 110 that is fluidly coupled to a lysis buffer source inlet 109. Growth medium may also be provided to the compartment 104 from a growth medium inlet 107. Waste materials may be removed from the growth chamber 102 through one of the waste outlets 114a-c.

Embodiments include a periodic, sequential cleaning and rinsing adjacent compartments to prevent biofilm growth on the inner wall of the growth chamber 102. When the compartment 104 rejoins the growth chamber, the bacterial culture in chamber 102 will be diluted by 1/16th (i.e., the ratio of the compartment 104 volume to the total volume of growth chamber 102).

Figure 2:
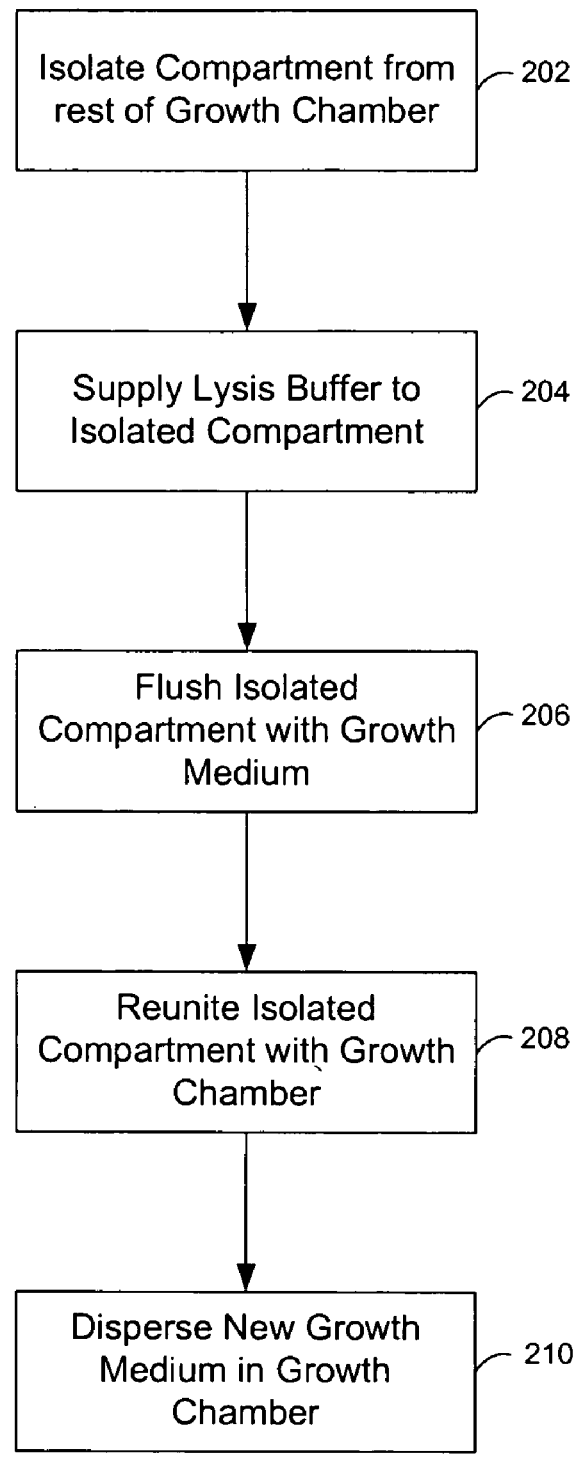
FIG. 2 shows a flowchart including steps for a chemostat cleaning method according to embodiments of the invention.

FIG. 2 shows a flowchart that includes steps for a chemostat cleaning method according to embodiments of the invention. The method includes the discrete lysing of individual compartments of the growth chamber of the chemostat. The discrete lysing includes fluidly isolating an individual compartment from the rest of the growth chamber at step 202 by closing valves at opposite ends of the compartment. The fluidly isolated compartment may be connected to a supply channel and an output channel, where the supply valve is opened to introduce lysis buffer to the compartment at step 204. The lysis buffer may include a lethal bacteria protein extraction reagent (e.g., a commercially available lysis agent from PIERCE in Rockford, Ill.) that flows through the compartment for a period of time (e.g., 60 seconds) to flush out the cell suspension and dissolve (lyses) away any cells that might be adhering to the wall. The lysis buffer may then be removed along with the remains of the cells, by flushing the compartment with fresh sterile growth medium for a period of time (e.g., about 60 seconds) at step 206. Once the compartment is rinsed and filled with fresh growth medium, supply channel and an output port may be closed and actuatable valves reopened to reunite the compartment with the rest of the growth-chamber in step 208. Rotary mixing may be resumed to disperse the influent quickly and uniformly throughout the growth-chamber in step 210.

The discrete flow/sequential lysis cleaning method may be repeated periodically during the experiment, using successive compartments as dilution premises. Sequential lysis of the growth chamber compartments can provide a periodic chemical cleaning of the growth-chamber over a period of time (e.g., about once every three hours) which can suppress or prevent biofilm formation on the surfaces of the chamber. Individual addressability of the growth chambers coupled with effective fluidic isolation allows for the removal of incipient wall growth in a given compartment without substantially harming bacteria growth in the rest of the growth chamber.

Examplary Chemostat Chip

Figure 3:
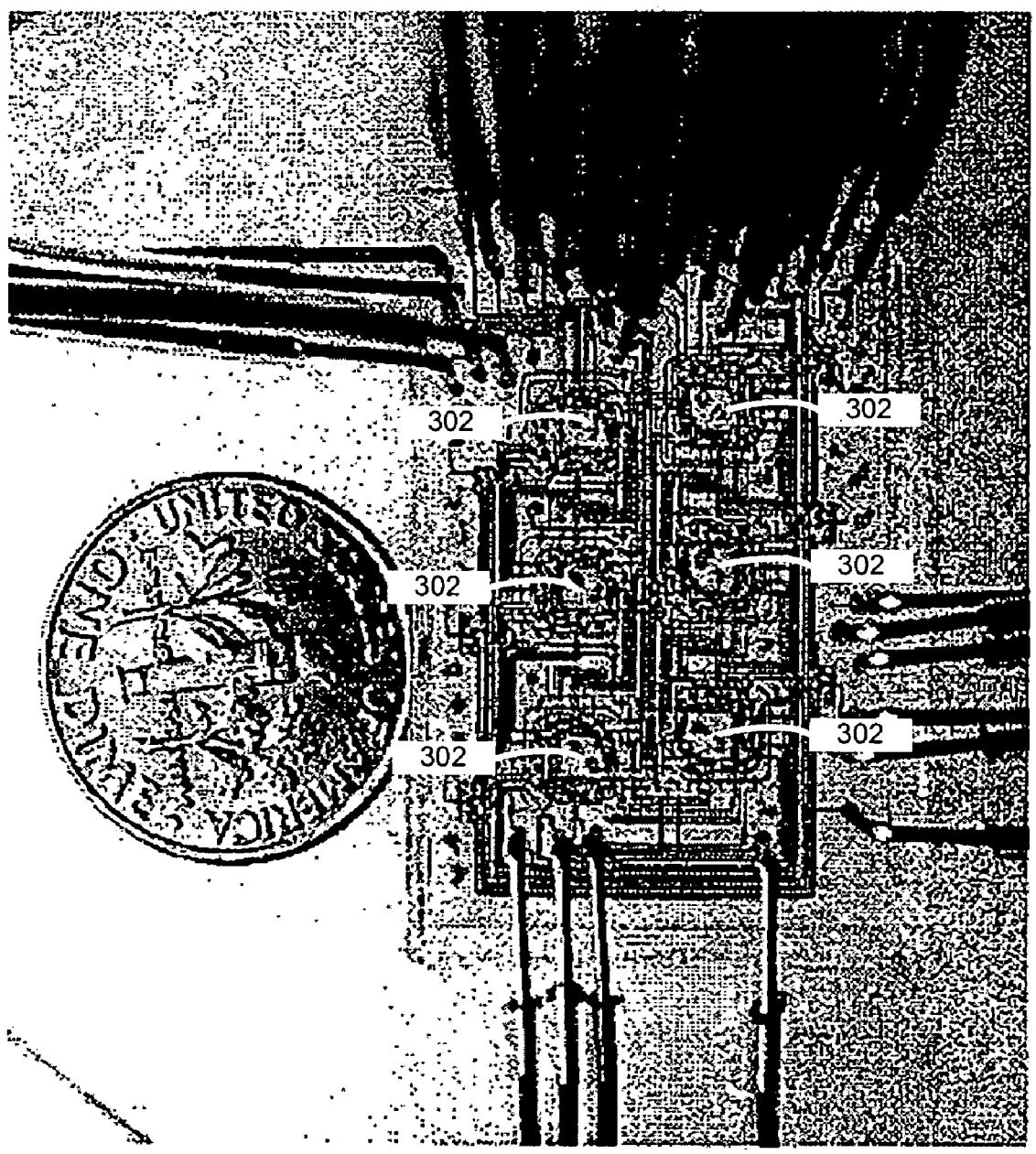
FIG. 3 shows a chemostat chip according to an embodiment of the invention.

The present invention includes arrays of two or more chemostats incorporated into a chemostat chip 300. FIG. 3 shows 6 chemostats 302 organized into a 2×3 array on a microfluidic chemostat chip 300. During operation, multiple chemostat experiments may be run in parallel (i.e., overlapping in time) on the chemostat chip 300, and an automated microscope reader (not shown) may perform real-time sampling and documentation of the microbial properties (e.g., total cell count) for each experiment. This kind of automated data acquisition reduces the chances of data artifacts caused by human error, and increases the data collection rate and the temporal resolution of the data recorded during the experiment.

The 2×3 array on chemostat chip 300 may have dimensions on the order of millimeters (e.g., 20 mm×35 mm×5 mm) and may be fabricated from a silicone elastomer. The chip 300 has six parallelly operable fluidic loop chemostats 302. Each chemostat 302 includes a growth chamber, encircled by a nutrient supply-line that connects to four input ports and an output port. Each of the growth chambers include a hollow round-cornered square strip (11.5 mm perimeter), with rectangular cross-sectional interior geometry (10 µm×140 µm). Situated along the growth chamber is a 3-valve peristaltic pump for the rotary mixing of the growth chamber contents. The growth chamber loops may have a rounded cross-sectional geometry in the areas that contain valves for fluidic isolation and peristaltic pumping. Umbilical fluidic links may connect the growth chamber to the supply line at eight strategic locations. Within the perimeter of each of the growth chambers are two ports. These ports may be 625 µm-diameter holes incorporated into the chip.

The small footprint and parallel architecture of the microfluidic-based chemostat allows for large-scale screening investigations in two dimensional chemostat arrays. The zero wall-growth aspect of the chip 300 makes possible the basic reduction of the chemostat equations to an ideal monotone system, simplifying the analysis of chemostat-like behavior. In the embodiment shown, each chemostat 302 holds an active volume of about 11 nL, so small quantities of reagents (e.g., growth medium) are required for the experiments. This significantly reduces the operational costs for experiments run on the chip 300.

Exemplary Fabrication of Chemostat Chip

Figure 4:
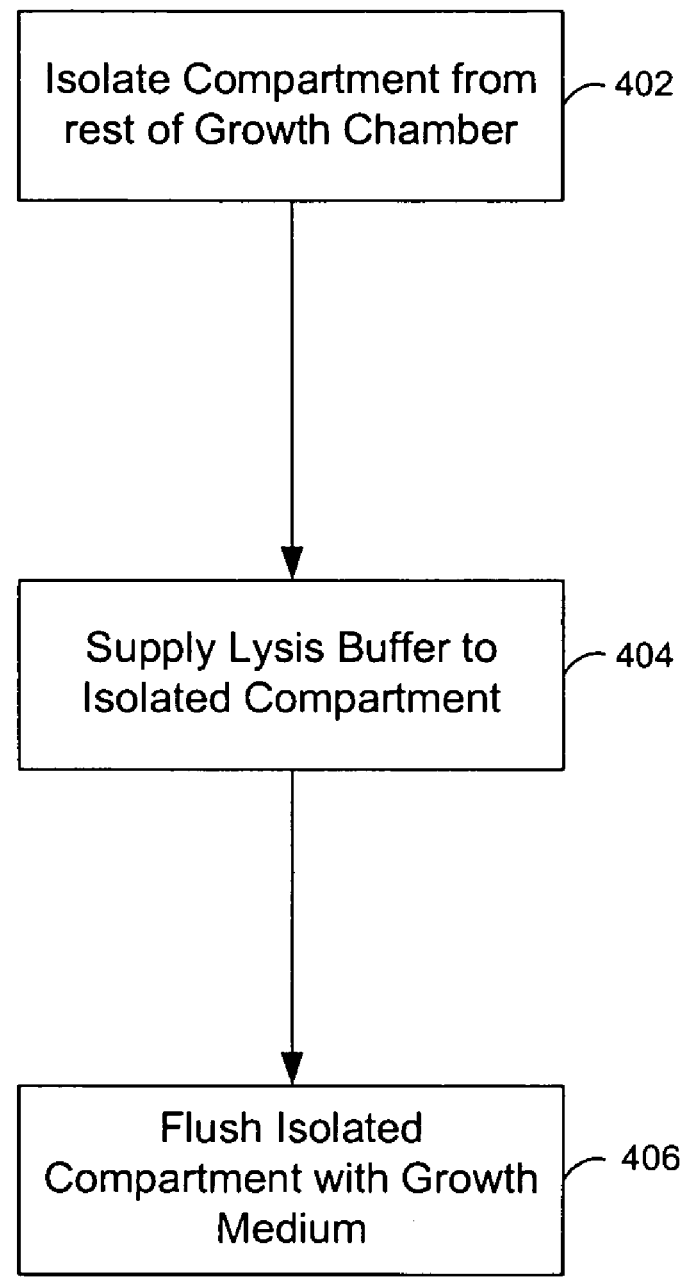
FIG. 4 shows a flowchart of a method of making a chemostat chip according to an embodiment of the invention.

Referring now to FIG. 4, a flowchart that includes steps in the method of making a chemostat chip is shown. The method includes forming a flow layer in step 402. The flow layer may be fabricated out of the silicone elastomer polydimethylsiloxane (PDMS) (General Electric RTV 615) using standard "multi-layer soft lithography". The layer may be formed with both rectangular channel geometry, as well as rounded geometry for valve actuation.

Negative molds for the flow layer may be cast by sequentially by applying two different types of photoresist. The rectangular channel features may be molded out of a first photoresist material that does not round when annealed (e.g., SU8 2010 from MicroChem Corporation of Newton, Mass.), while other features of the flow layer may be made from a second photoresist material (e.g., SRJ 5740 from MEMS Exchange in Reston, Va.). The first photoresist material may be spun onto a silicon wafer (e.g., a wafer spinning at 3,000 rpm for 60 sec) to create a 10 µm thick layer and patterned using negative high-resolution transparency masks. The second photoresist material may be spun onto the same silicon wafer (e.g., spinning the wafer at 2,200 rpm for 60 sec) to create a 10 µm thick layer and patterned using positive high-resolution transparency masks, aligned to fit the patterns formed in the first photoresist material. The two-photoresist hybrid mold may then be annealed at 120° C. for 20 minutes to achieve rounded channel geometry for the features in the channels of the second photoresist material while preserving the rectangular geometry of the features in the first photoresist material.

The fabrication method also includes forming a first and second control layer in step 404, and then coupling the flow layer between the control layers in step 406. The control layers have distinct functionalities at different regions of each fluidic module for controlling flow, rotary mixing, and fluidic isolation within the growth chamber of each chemstat in the array. At each junction between a control and fluid line, there exists a thin membrane, which can be deflected by hydraulic actuation of the control channel to close the flow channel, creating a valve. Three valves in a row may be used to form a peristaltic pump for circulating fluids in the growth chambers.

The control and fluid layers of the chip may be cast from separate molds that are patterned on silicon wafers with photolithography. Negative molds for features of the control layers may be fabricated from a photoresist (e.g., AZ PLP 100 XT photoresist from Clariant Corporation, Somerville, N.J.). The photoresist may be spun onto silicon wafers at 1,200 rpm for 60 sec to create a 30 μm thick layer and patterned using positive high-resolution transparency masks.

Additional details on the formation of microfabricated fluidic devices utilizing elastomer materials will be described following a discussion of some experiments that were conducted using chemostat systems according to embodiments of the invention.

EXPERIMENTAL

Experiments were conducted using chemostats according to embodiments of the invention to characterize the behavior of *Escherichia Coli* bacteria at different dilution rates and influent compositions.

Steady-state behavior of *E. Coli* cultures were investigated with the chemostats, including the measurement and modeling of growth rate modulation by nutrient availability, taking into account the effects of toxic metabolite accumulation. Studies have shown that nutrient depletion and toxic metabolite accumulation are not the only factors responsible for the transition from the exponential to the stationary phase in *Escherichia Coli* cultures. Quorum-sensing mechanisms (cell-associated sensing) have also been found to be important regulators of cell division and density, even under non-limiting (albeit declining) nutrient concentrations. In other words, in the presence of non-limiting albeit declining nutrient concentrations, *E. Coli* bacteria adjust their own growth rate in response to their cell density through a cell-associated sensing mechanism capable of steering a bacterial culture from the exponential to the stationary growth phase. This may be how the bacteria population economizes nutrient consumption to preserve metabolic energy and maximize the period of culturability after retirement into the stationery phase.

Chemostat experiments were performed using *E. coli* bacteria growing on complex (LB) medium. A model that was consistent with our experimental measurements suggested that steady-state nutrient concentrations were not in the limiting regime. This would attribute the establishment of steady-state in the chemostats to a cell-density dependent mechanism other than toxic metabolite accumulation. This provides evidence of growth limitation by the aforementioned cell-associated sensing mechanism. The experiments with the chemostats suggest a reliance on cell-associated sensing instead of nutrient limitation to establish steady-state growth. Details about the chemostat system will now be described.

Chemostat System: The microfluidic chemostat system used for the experiments is equipped with a non-invasive automatic online cell density analyzer, which allows for simultaneous monitoring of six micro-chemostats (about 10 nL each) on a single chip, and provides high temporal resolution. The chemostat is refined to operate with zero microbial wall growth. The microfluidic chips are fabricated from a silicone elastomer according to standard soft-lithography techniques. We attribute the ability of bacteria to thrive in these devices to the high gaseous permeability of the silicone elastomer as well as an about 100 fold increase in the growth chamber surface area to volume ratio.

Bacterial Strain: Experiments included the use of *E. Coli* strain MG1655, and the Dh5α strain that expresses lacI. These strains were received from Dr. Uri Alon.

Preculture: Luria-Bertani (LB) medium contained Bacto Yeast Extract (5 $gL^{-1}$; Beckton, Dickinson and company, Sparks, Md.), Bacto Tryptone (10 $gL^{-1}$; Becton, Dickinson and Company, Sparks, Md.), NaCl (10 $gL^{-1}$; Mallinckrodt Laboratory Chemicals, Phillipsburg, N.J.), Bovine Serum Albumin (5 $gL^{-1}$; Sigma Aldrich, St. Louis, Mo.) as an anti-adhesion adjuvant and kanamycin (30 μg/ml), as an antibiotic. Cultures (1 ml) inoculated from frozen stock were grown for six hours at 37° C. with shaking at 280 rpm. In additional experiments, a MOPS EZ rich medium was used that included 10% (v/v) MOPS mixture, 1% (v/v) 0.132M $K_2HPO_4$, 10% (v/v) ACGU supplement, 20% (v/v) supplement EZ and 11 mM glucose (TekNova Inc., Half Moon Bay, Calif.).

Chemostat Culture: Chemostat cultures (standard volume 11 nL, temperature 21° C., pH 7) were inoculated with the preculture to about 5 bactria $\mu L^{-1}$. The LB medium was used with the concentration of bacto tryptone adjusted to 3 $gL^{-1}$, 0.5 $gL^{-1}$, and 0.1 $gL^{-1}$. In additional experiments, chemostat cultures with standard volumes of 16 nL, temperatures of 21° C. or 37° C., and pH 7 were inoculated with the preculture to about 20 bactria $\mu L^{-1}$. The same LB medium was used.

The Microfluidic Chemostat Reader: A microfluidic chemostat reader was assembled to facilitate the automated experiment control, data acquisition and data processing. It was a multi-component system consisting of a Nikon TE 2000 (A. G. Heinze Inc., Lake Forest, Calif.) inverted microscope furnished with a PRIOR Scientific XYZ motorized stage system (A. G. Heinze Inc., Lake Forest, Calif.). Imaging was done using a 40× dry Nikon objective or a Plan Fluor 40×0.75 NA ph2 DLL objective. The images were taken by a charge-coupled device (CCD) camera and recorded by a PXC200 color frame grabber (Cyberoptics Semiconductor, Beaverton, Oreg.). We developed algorithms that were implemented in Labview software to control the synchronized operation of these ingredient components (as well as other chip operation functions).

Microscopic counting: The chemostat architecture was such that all the bacterial cells were confined in a growth chamber 10 μm high, which is the equivalent of a single focal plane. As such, the total number of cells in each chemostat was determined through automated microscopy by counting the number of cells present in a growth chamber section of known volume. A set of 9 still images was taken at a given location of the chemostat, rotary-mixing the growth-chamber contents in-between consecutive snapshots. We developed image-processing algorithms (implemented in Matlab) to determine the average number of cells in the set of pictures taken, from which the total cell count could be extrapolated. The motorized stage system allowed for the simultaneous documentation of multiple chemostat experiments running in parallel on the chip.

40 experimental runs were performed in 5 different chips using a variety of growth media (MOPS EZ RICH and LB broth with various concentrations of glucose and bacto-trptone respectively) at 21° C. or 37° C. Table 1 summarizes the experiment conditions for the experiments.

TABLE 1

Growth Plots Over Time for Various Growth Media and Dilution Rates

| Plot No. | Growth Medium | Dilution Rate | Temperature |
|---|---|---|---|
| 1 | MOPS, 0.11 nM glucose | 0.35 hr$^{-1}$ | 37° C. |
| 2 | MOPS, 0.11 nM glucose | 0.31 hr$^{-1}$ | 37° C. |
| 3 | LB, 0.5 g/L bacto-tryptone | 0.25 hr$^{-1}$ | Room Temperature |
| 4 | LB, 0.5 g/L bacto-tryptone | 0.31 hr$^{-1}$ | Room Temperature |
| 5 | LB, 3 g/L bacto-tryptone | 0.38 hr$^{-1}$ | Room Temperature |
| 6 | LB, 0.5 g/L bacto-tryptone | 0.38 hr$^{-1}$ | Room Temperature |

Figure 5A:
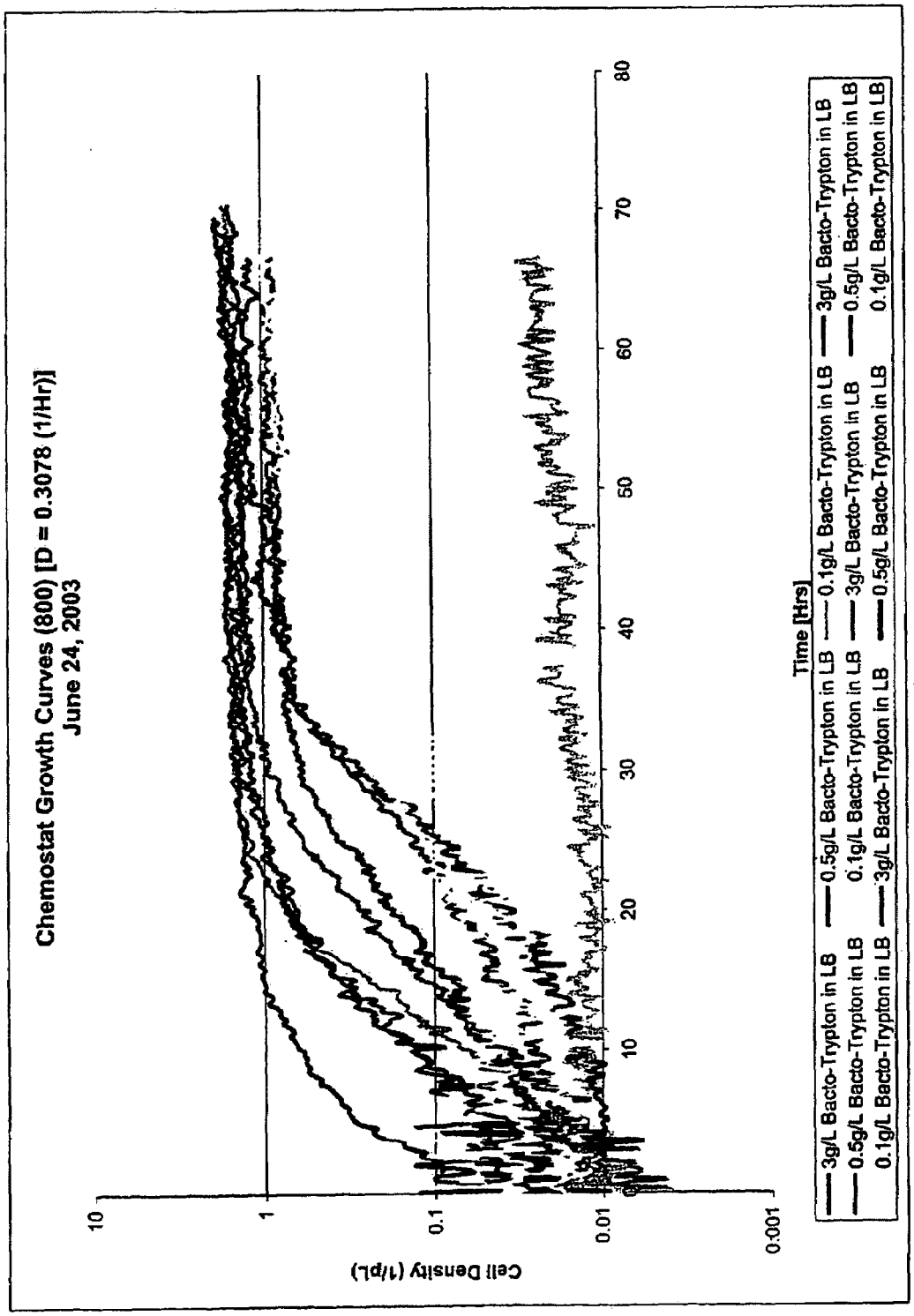
FIGS. 5A-B show bacterial culture growth curves taken during experiments using a chemostat system according to the invention.
Figure 5B:
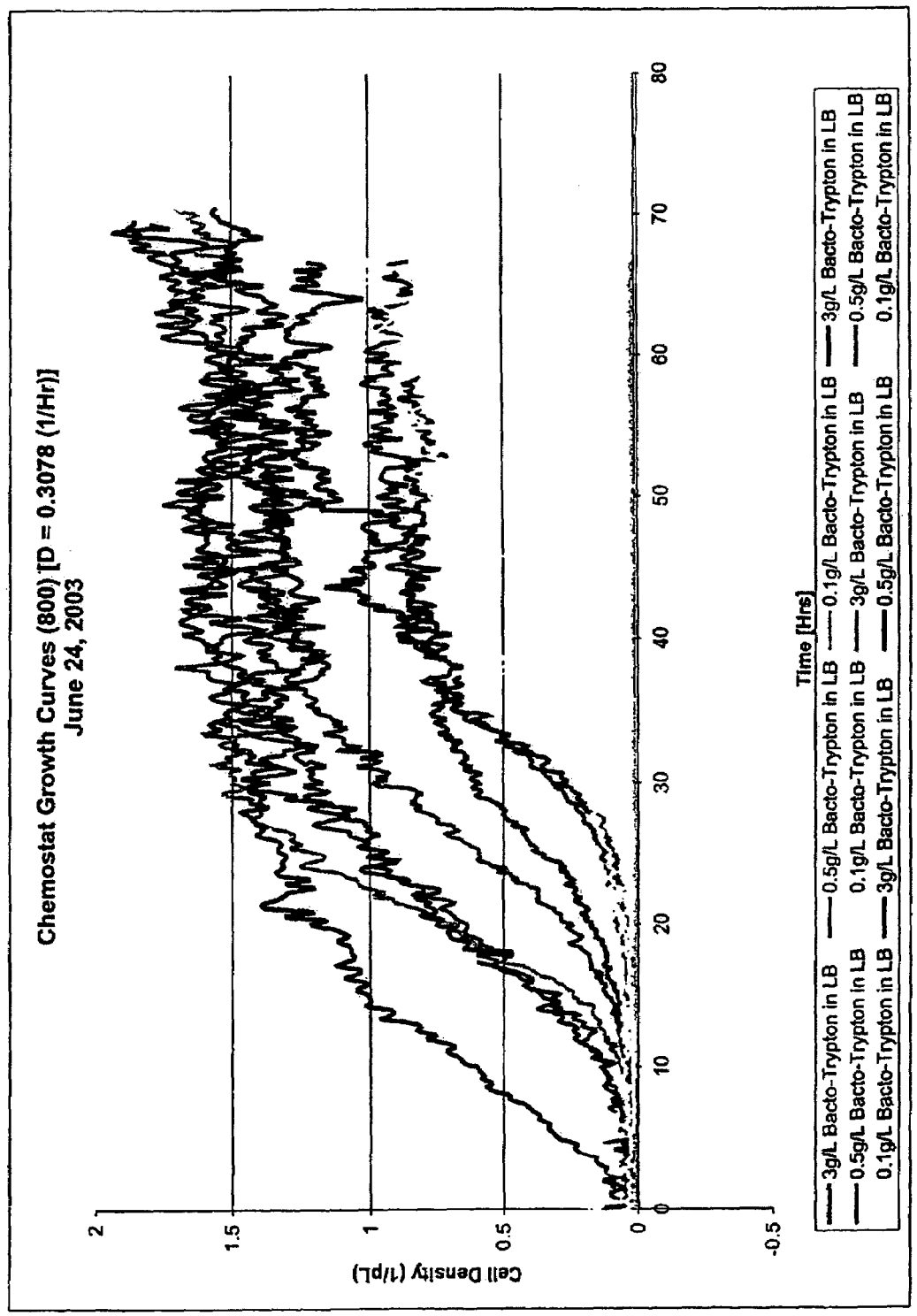
Figure 6:
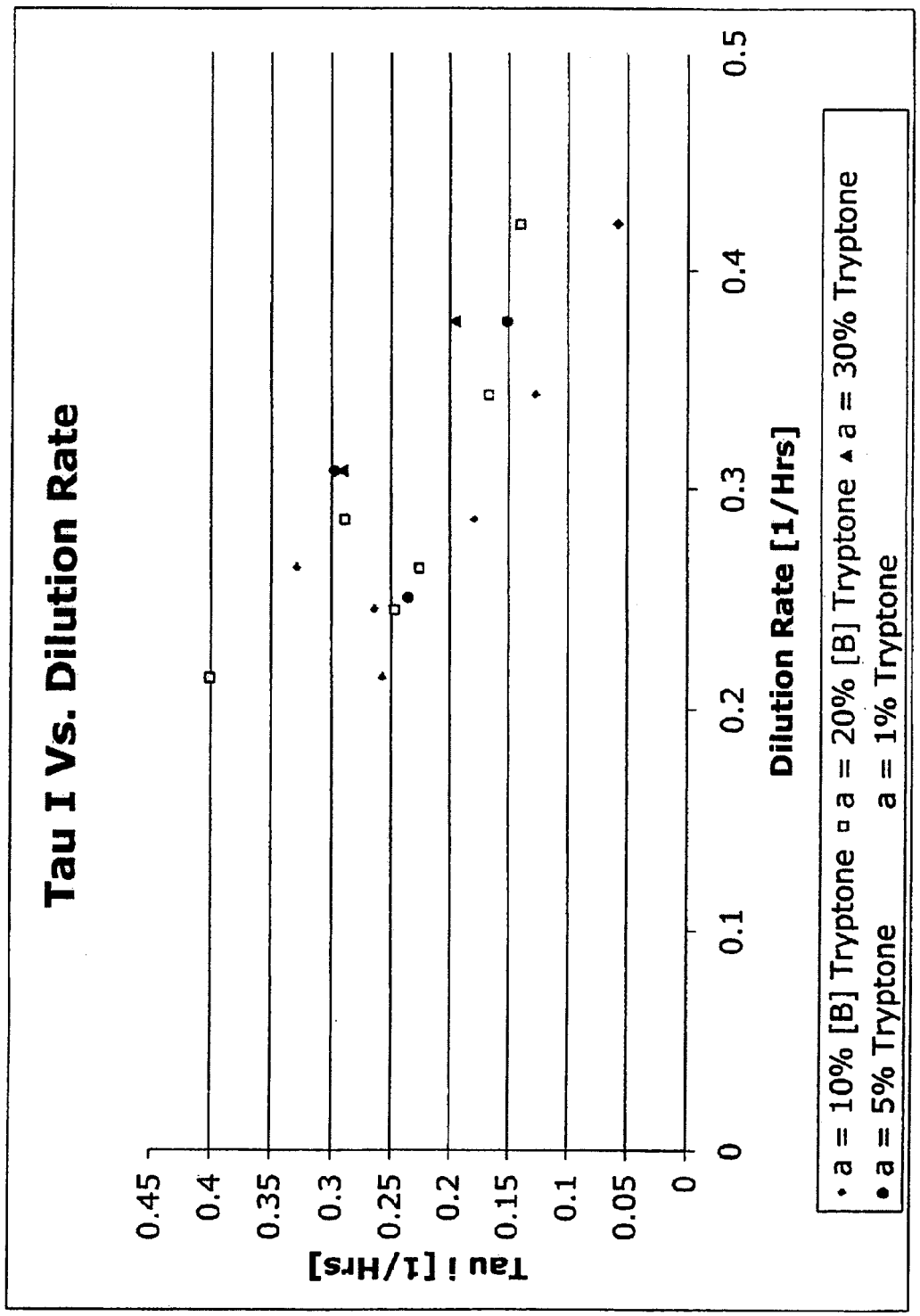
FIG. 6 shows a plot of Tau I versus the dilution rate from experiments run using a chemostat system according to the invention.

FIGS. 4A-B show growth curves as a function of time in various growth media. The red data (5,6,7) represent different concentrations of bacto-tryptone in LB at a fixed dilution rate whereas the empty circles (3,4,6) depict constant influent nutrient composition at various dilution rates. FIG. 5 shows Tau I and a function of dilution rates. FIG. 6 shows steady state cell concentrations as a function of dilution rates in various growth media. Upon inoculation, each chemostat culture began with a variable lag period, which depended on the age and size of the inoculum. This was replaced by an exponential phase that gave way to a steady-state regime. Steady-state operation was ascertained to be possible over a range of dilution rates (0.072-0.352 hr$^{-1}$). Over this range, the culture was self-adjusting in that on setting the flow rate to a give value, the concentration of organisms achieved a steady-state. On changing the flow-rate, new steady-states were automatically attained.

From observations and measurements made in the experiments, two models were constructed of the dynamics in the microfluidic chemostat. The models use a small number of parameters to represent the factors involved in controlling cell growth. These models were consistent with the observations and measurements done in the investigation. The models indicate that steady-state nutrient concentration is not in the limiting regime. As such, the steady state observed may be due to something other than nutrient depletion. The steady state may therefore be attributed to toxic metabolite accumulation, or a quorum sensing dependent mechanism.

First Model for Bacterial Growth

To probe the dynamics of bacterial growth in the chemostat system used in the experiments, we modified the conventional chemostat model to account for previous observation that the growth rate of *E. coli* cultures is also regulated by the detection and quantitative analysis of the cell concentration. We kept the Monod model, which defines the relationship between the specific growth rate and substrate concentration. We included a term representing cell density-dependent regulation of the growth rate (toxic metabolite or quorum-sensing molecule accumulation). Thus, microbial growth in the microfluidic chemostat is represented in this model as:

$$\dot{x}_1 = \mu_{max}\frac{x_1 x_2}{k_s + x_2} - Dx_1 - \gamma x_1 x_3 \quad \text{Eq. 1}$$

$$\dot{x}_2 = D(aA' - x_2) - \Lambda\frac{x_1 x_2}{k_s + x_2} \quad \text{Eq. 2}$$

$$\dot{x}_3 = \xi x_1 - Dx_3 \quad \text{Eq. 3}$$

Here, $x_1$ is the bacterial population, $x_2$ the nutrient concentration and $x_3$ the cell density dependent (CDD) growth inhibitory factor (concentration of toxic metabolites or QS molecules). The first equation expresses, respectively, bacterial growth by nutrient consumption, dilution at a rate D, and growth-inhibition due to the CDD factor. The second equation describes nutrient injection, dilution, and consumption. The third equation conveys CDD factor production and dilution. $\mu_{max}$ is the maximum growth rate that occurs at saturation levels of the growth-limiting substrate. D is the dilution rate and $k_s$ is the substrate concentration, at which growth occurs at half its maximum value, $½ \mu_{max}$. a is the concentration of the growth-limiting substrate in the influent. $\gamma$ and $\xi$ represent the growth-inhibitory effect of the CDD factor on the microbes and its rate of production by the microbes. $\Lambda$ is the ratio of the growth constant to the yield coefficient.

We simplify this model by assuming that the CDD factor concentration is quasi-steady. Including CDD factor dynamics allows for cell concentration 'overshoot' and oscillate. We ignore that here, and assume simply:

$$x_3 = \frac{\xi}{D}x_1 \quad \text{Eq. 4}$$

We also rescale the two concentration and time variables to reduce the six-dimensional parameter space by three dimensions. With the following scalings: $t=T/\mu_{max}$, $x_1=y_1/\Lambda$, and $x_2=k_s y_2$, the equation set (Eqs. 1, 2 and 3) reduces to:

$$\dot{y}_1 = \frac{y_1 y_2}{1 + y_2} - \overline{D}y_1 - \frac{\Psi}{\overline{D}}y_1^2 \quad \text{Eq. 5}$$

$$\dot{y}_2 = \overline{D}(aA - y_2) - \frac{y_1 y_2}{1 + y_2} \quad \text{Eq. 6}$$

where, $$\overline{D} = \frac{D}{\mu_{max}}, A = \frac{A'}{k_s}, \text{ and } \Psi = \frac{\gamma \xi}{\mu_{max}\Lambda}$$

are the independent parameters governing the dynamics of the system. Here, $\overline{D}$ is the dilution rate scaled by $\mu_{max}$, A is the percentage concentration of bacto-Tryptone in the influent with respect to the optimum concentration of 10 gL$^{-1}$, and $\Psi$ is the ratio of the CDD factor to the initial growth rate. These scalings are chosen because a and D are the 'knobs' that can be turned experimentally. This model allows bacteria to adjust their growth rate to declining albeit non-limiting nutrient amounts.

Discretized Dilutions: Dilution in the microfluidic chemostat is performed in discrete steps to accommodate a sequential lysis scheme. Even with about a 1/15th dilution fraction, the microfluidic discretized-flow culture will reach steady state. This is observed by analyzing the recursive counterparts of Eqs. 1, 2 and 3, which govern microbial growth in a discretized-flow system.

$$\dot{x}_{1_{n\Delta t}} = \mu_{max}\frac{x_{1_{n\Delta t}}x_{2_{n\Delta t}}}{k_s + x_{2_{n\Delta t}}}x_{1_{n\Delta t}} - H_{n\Delta t}\frac{T}{\Delta t}Dx_1 - \gamma x_{1_{n\Delta t}}x_{3_{n\Delta t}} \quad \text{Eq. 8}$$

-continued $$\dot{x}_{2_{n\Delta t}} = H_{n\Delta t}\frac{T}{\Delta t}D(aA' - x_{2_{n\Delta t}}) - \Lambda\frac{x_{1_{n\Delta t}}x_{2_{n\Delta t}}}{k_s + x_{2_{n\Delta t}}} \quad \text{Eq. 9}$$

$$\dot{x}_{3_{n\Delta t}} = \gamma x_{1_{n\Delta t}} + H_{n\Delta t}\frac{T}{\Delta t}Dx_{3_{n\Delta t}} \quad \text{Eq. 10}$$

with initial conditions, $$x_{1(n=1)\Delta t}=x_1^0, x_{2(n=1)\Delta t}=a, x_{3(n=1)\Delta t}=0, n=1,2,3$$

Here, $\Delta t$ is the discretized time increment of the simulation and T is the period between consecutive dilutions. TD is the fraction of the chemostat growth chamber replaced during each dilution. $H_{n\Delta t}$ represents a Heaviside unit step function defined such that $H_{n\Delta t}=1$ if n is step during which a dilution occurs (the first time unit during the dilution period T) and zero otherwise. At a fixed dilution rate, as the dilution fraction approaches zero, the dilution period T approaches the time increment $\Delta t$. Evidently, the flow becomes continuous and the equation set (Eqs. 8, 9 and 10) becomes identical to set (Eqs. 1, 2 and 3).

E. Coli Growth in the microfluidic chemostat: In standard chemostat operation, the influent composition is such that all the ingredients are in optimal amounts, except for the growth-limiting factor, whose concentration is kept sufficiently low. As such, the growth-limiting factor determines the growth rate and steady-state chemostat concentration. In the microfluidic chemostat experiments, undefined Luria-Bertani (LB) medium was used with various concentrations of the bacto-tryptone ingredient. In such complex substrate medium, growth at the expense of the substrate utilized at the highest efficiency leads to the establishment of steady-state, accompanied by an incomplete utilization of the other substrates present. For this reason, a specific albeit unknown bacto-tryptone component in the influent played the role of growth-limiting factor.

A series of experiments were performed at room temperature (21° C.) with different influent bacto-tryptone concentrations (3 gL$^{-1}$, 0.5 gL$^{-1}$, and 0.1 gL$^{-1}$) in micro-chemostats inoculated with about 5 bacteria per μL. In tandem with theory, each of the chemostat cultures began with a variable lag period, which depended on the age and size of the inoculum. This was replaced by an exponential phase that gave way to an indefinite steady-state regime (see FIGS. 4A-B). Steady-state operation was ascertained to be possible over a range of dilution rates (0.072-0.352 hr$^{-1}$). Over this range, the culture was self-adjusting in that on setting the flow rate to a given value the concentration of organisms would move towards and settle down at steady-state levels, which are maintained indefinitely as long as the flow rate is unaltered. On changing the flow-rate, new steady-state levels were automatically attained.

During the early stage of the exponential growth phase, where the population size is small and the nutrients are non-limiting, the specific growth rate $\mu_{max}$ is given by the equation $$\mu_{max} \approx \frac{d(\log_e x_1)}{dt} + D \quad \text{Eq. 11}$$

The value $d(\log_e x_1)/dt$ was determined experimentally by fitting the cell population density $x_1(t)$ to an exponential function of the form $y=ae^{bt}+c$. The results are displayed in FIGS. 5A-B.

Solving the scaled model for steady-state concentrations gives four fixed points. One is the trivial fixed point with no bacteria ($y_1^a=0$). Of the other three non-trivial fixed points, only one had non-negative cell and nutrient concentrations. The measured initial growth rate, $\mu_{max}\approx 0.52$ hr$^{-1}$ is constant irrespective of the influent nutrient composition, which is in agreement with the Monod model.

The Steady-State cell concentration: $y_1$ was scaled with $1/\Lambda$, a parameter which we can not measure. Therefore, all measured cell concentrations were normalized by the value at (a=30% and $\overline{D}$=0.47), and $y_1$ values by $y_1$(a=30, $\overline{D}$=0.47). Reasonable fits are obtained for A=5 and $\Psi$>0.5 (see FIG. 6). Scaling of $y_1$ was scaled with $1/\Lambda$, a parameter which we can not measure denies us a tight fit for $\Psi$. Nevertheless, cell density dependent growth inhibition is necessary to explain the data. To demonstrate this, we carried out a similar analysis for a system without cell density dependent growth regulation ($\Psi$=0). This yields steady-state cell and nutrient concentrations:

$$y_1^{ss} = Aa - \frac{\overline{D}}{1-\overline{D}} \text{ and } y_2^{ss} = \frac{\overline{D}}{1-\overline{D}} \quad \text{Eq. 12}$$

implying that at all dilution rates, steady-state populations will be separated by a constant proportional to the nutrient concentration, which is not observed experimentally (see FIGS. 4A-B) This shows that $\Psi$ is 'sufficiently large', which is strong evidence for cell density dependent growth limitation.

Figure 7:
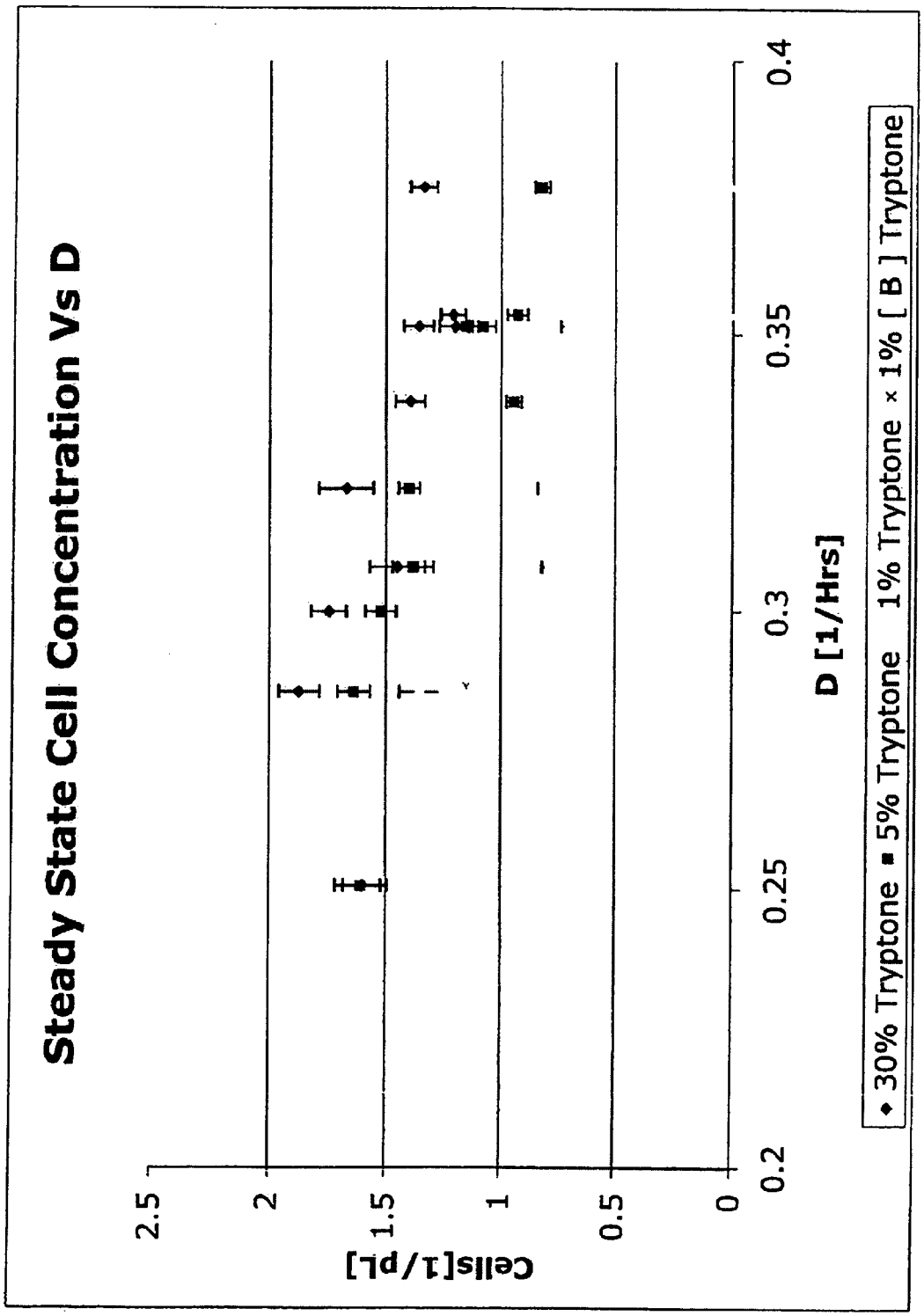
FIG. 7 shows a plot of steady state cell concentrations versus the dilution rate from experiments run using a chemostat system according to the invention.

Time constant for approaching steady-state: Experimental values for the time constant for approaching steady-state were determined from the chemostat growth curves. Reasonable fits are obtained for A=5 and $\Psi$>0.5 (see FIG. 7). As such, cell density dependent growth limitation is necessary to explain the data. We analyzed this parameter for a system with $\Psi$=0. With this condition, time constants to approach steady state vary like ($\overline{D}$, aA$-\overline{D}-2$aA$\overline{D}+\overline{D}^2$+aA$\overline{D}^2$), which results in unconvincing fits. This yields time constants.

The model was consistent with the experimental observations and measurements. It provided estimates of non-measurable variables such as the nutrient concentration. Using the fixed-point values for cell density, the model predicted the steady-state nutrient concentrations. The steady-state nutrient concentrations were found to be in the non-limiting regime (see FIG. 7). The simple model described above proved to be consistent with the experimental measurement (the steady-state nutrient concentration and time constant for arrival to steady state).

Second Model for Bacterial Growth

A second model was also used to describe microbial growth in the chemostat. This second model combines the Monod model defining the relationship between the specific growth rate and substrate concentration for substrate-limited growth and a model developed by C. C. Spicer to describe the rate nutrient consumption and growth limitation by toxic metabolites. In the second model, the differential equations used to describe microbial growth in the chemostat at a dilution rate D are:

$$\frac{1}{x_1}\frac{dx_1}{dt} = \frac{\mu_{max}x_2}{k_s+x_2} - D - \zeta x_3 \quad \text{Eq. 13}$$

-continued $$\frac{dx_2}{dt} = D(a - x_2) - \frac{1}{Y_{x_1/x_2}}\left(\frac{\mu_{max}x_2}{x_2 + k_s}\right)x_1 \qquad \text{Eq. 14}$$

$$\frac{dx_3}{dt} = \gamma x_1 - Dx_3 \qquad \text{Eq. 15}$$

Here, $x_1$, $x_2$ and $x_3$ represent the microbial population size, growth-limiting nutrient concentration and toxic metabolite concentration, respectively. $\mu_{max}$ is the growth rate constant (i.e. the maximum growth rate that occur at saturation levels of the growth-limiting factor) and $k_s$ is the substrate concentration at which growth occurs at half its maximum value, ½ $\mu_{max}$. a is the concentration of the growth-limiting substrate in the influent. The constants $\zeta$ and $\gamma$ represent the lethal effect of the toxic metabolite on the microbes and its rate of production by them. $Y_{x_1/x_2}$ is the yield coefficient, representing the weight of bacteria formed per amount of growth-limiting substrate consumed.

During the initial stage of the exponential growth phase when the cell density is low, the toxic metabolite concentration $x_3$ is negligibly small. Under these conditions, the growth-limiting substrate concentration is high compared to $k_s$. As such, Eq. 13 reduces to:

$$\frac{1}{x_1}\frac{dx_1}{dt} = \frac{d(\log_e x_1)}{dt} \sim \mu_{max} - D \qquad \text{Eq. 16}$$

During steady-state, the concentration of the growth-limiting substrate is quite small. Under such conditions, the microbial growth rate is linearly proportional to the concentration of the growth-limiting factor. As such the growth governing differential equations at steady state reduce to:

$$\frac{1}{x_1}\frac{dx_1}{dt} = \lambda x_2 - D - \zeta x_3 = 0 \qquad \text{Eq. 17}$$

$$\frac{dx_2}{dt} = D(a - x_2) - \kappa x_1 x_2 = 0 \qquad \text{Eq. 18}$$

$$\frac{dx_3}{dt} = \gamma x_1 - Dx_3 = 0 \qquad \text{Eq. 19}$$

where $\lambda$ is the constant of proportionality relating the growth rate to the growth-limiting nutrient concentration and $\kappa$ is the rate of consumption of growth-limiting nutrient per bacteria. As such, $\lambda/\kappa$ is the amount of growth factor required to create a single organism.

At high dilution rates, the cell density the steady-state cell density is suppressed. For this reason, we can estimate the value of $\kappa$ by neglecting the concentration as well as effect of the toxic metabolites. The steady-state nutrient concentration ($\tilde{x}_2$), and the constant $\kappa$ can be determined from Eq. 17 and Eq. 18, respectively, as:

$$\kappa = \frac{1}{x_1}(\lambda a - D_{high}) \qquad \text{Eq. 20}$$

When the dilution rate is lowered, the steady-state cell density increases, and the toxic metabolite concentration becomes significant. From Eq. 18 and 19 we determine $\tilde{x}_2$ and $\tilde{x}_3$ (in terms of $\gamma$):

$$\tilde{x}_2 = \frac{D_{low}a}{D_{low} + \kappa \tilde{x}_1} \qquad \text{Eq. 21}$$

$$\tilde{x}_3 = \frac{\gamma}{D_{low}}\tilde{x}_1 \qquad \text{Eq. 22}$$

For mathematical convenience $\gamma$ is reserved as a bookkeeping parameter for unit conversion purposes in Eq. 13 and its value is confined to unity. The constant $\mu$ thus becomes:

$$\mu = \frac{1}{\gamma}\left[\frac{D_{low}}{\lambda}(\lambda \tilde{x}_2 - D_{low})\right] \qquad \text{Eq. 23}$$

Discretized Dilutions: The chemostat system used in the experiments are operated a discrete mode (i.e., non-continuous). Dilutions are performed in discrete steps to prohibit the exposure of all the cells in the growth chamber to the lysis buffer. The model is also premised on each discrete dilution step decreasing the microbial population by a sixteenth. Even with such a dilution fraction, a microfluidic microbial discretized-flow system will reach steady state. The discretized and continuous modes of operation can be reconciled by analyzing the set of recursive equations that govern microbial growth in a discretized-flow system.

$$x_{1_{n\Delta t}} = x_{1_{(n-1)\Delta t}} + \left[\frac{dx_1}{dt}\right]_{(n-1)\Delta t}\Delta t \qquad \text{Eq. 24}$$

$$x_{2_{n\Delta t}} = x_{2_{(n-1)\Delta t}} + \left[\frac{dx_2}{dt}\right]_{(n-1)\Delta t}\Delta t \qquad \text{Eq. 25}$$

$$x_{3_{n\Delta t}} = x_{3_{1(n-1)\Delta t}} + \left[\frac{dx_{31}}{dt}\right]_{(n-1)\Delta t}\Delta t \qquad \text{Eq. 26}$$

$$\left[\frac{dx_1}{dt}\right]_{n\Delta t} = x_{1_{n\Delta t}}[\lambda x_{2_{n\Delta t}} - \mu x_{3_{n\Delta t}}] - \frac{1}{\Delta t}H(t)Fx_{1_{n\Delta t}} \qquad \text{Eq. 27}$$

$$\left[\frac{dx_2}{dt}\right]_{n\Delta t} = \kappa x_{1_{n\Delta t}}x_{2_{n\Delta t}} + \frac{1}{\Delta t}H(t)F[a - x_{2_{n\Delta t}}] \qquad \text{Eq. 28}$$

$$\left[\frac{dx_3}{dt}\right]_{n\Delta t} = \gamma x_{1_{n\Delta t}} + \frac{1}{\Delta t}H(t)x_{3_{n\Delta t}} \qquad \text{Eq. 29}$$

$$x_{1_{(n=0)\Delta t}} = x_{1_0} \qquad \text{Eq. 30}$$

$$x_{2_{(n=0)\Delta t}} = a \qquad \text{Eq. 31}$$

$$x_{3_{(n=0)\Delta t}} = x_{3_0} \qquad \text{Eq. 32}$$

Where $\Delta t$ is the discretized time increment of the simulation, F is the fraction of the chemostat replaced during each dilution, H(t) is a Heaviside unit step function defined such that H(t)=1 at the beginning of a dilution and H(t)=0 otherwise. The dilution rate D is replaced by the fact that dilutions are performed periodically according to a time period T=F/D. At a fixed dilution rate, as the dilution fraction approaches zero, the dilution period shrinks, and the flow becomes continuous.

Growth in continuous culture: In standard chemostat operation, the influent contains optimum concentrations of all growth factors required by the bacterium, with the exception of one, the growth-limiting factor. The growth-limiting factor, whose concentration is kept relatively low, determines the cell density in the resident culture during steady-state. In the microfluidic chemostat experiments, undefined Luria-Bertani (LB) medium was used with various concentrations of the bacto-tryptone ingredient. In such complex substrate medium, growth at the expense of the substrate utilized at the highest efficiency leads to the establishment of steady-state, accompanied by and incomplete utilization of the other substrates present. For this reason, a specific albeit unknown bacto-tryptone component in the influent served as the growth-limiting factor.

During the early stage of the exponential growth phase, when the cell density is low, the toxic metabolite concentration is negligibly small. Under these conditions, the organisms are growing in substrate concentrations, which are high compared to $\kappa_s$, implying that the specific growth rate is approximately equal to $\mu_{max}$. As such, the specific growth rate of the E. Coli strain was determined at various dilution rates using the microfluidic apparatus under the experimental conditions according to the equation:

$$\mu_{max} \approx \frac{d(\log_e x)}{dt} + D \qquad \text{Eq. 33}$$

The value $d(\log_e x)/dt$ was determined from the constant, b, obtained by fitting $x_1(t)$ to an exponential function of the form $y=ae^{bt}+c$. Typical experimental results are shown in FIG. 4.

Experiments were performed at room temperature (21° C.) with different initial bacto-tryptone concentrations in chemostats inoculated with about 5 bacteria per 1 μL. In tandem with theory, each of the chemostat cultures began with a variable lag period, which depended on the age and size of the inoculum. This was replaced by an exponential phase that gave way to an indefinite steady-state regime. Steady-state operation was ascertained to be possible over a range of dilution rates (0.2. to 0.4). Over this rate of dilution rates, the culture was self-adjusting in that on setting the flow rate to a given value, the concentration of organisms would move towards and settle-down at steady-state levels which are maintained indefinitely as long as the flow rate is unaltered; on changing the flow-rate, new steady-state levels were automatically attained.

Effect of influent substrate concentration: At high dilution rates, the steady-state concentration is proportional to the bacto-tryptone concentration in the influent. However, this proportionality fades away as the dilution rate is lowered. This phenomenon could be attributed to growth limitation by the microbial toxic metabolites. At high dilution rates, which favor low steady-state cell densities, the concentration as well as the effect of the toxic metabolites is restrained. As the dilution rate is lowered, the cell culture self-adjusts in an attempt to arrive and settle at a higher steady-state cell concentration. In tandem with the cell density, the toxic metabolite concentration increases to growth-limiting levels. As such, at a fixed dilution rate, different bacto-tryptone concentrations in the influent result in the same cell density.

In FIG. X the three graphs show the E. coli cell density in the micro fluidic chemostat as a function of time at different influent bacto-tryptone concentrations at room temperature and a fixed dilution rate $D=0.377$ hr$^{-1}$. We were also able to control the growth rate of the bacteria by adjusting the dilution rates.

LB is a complex medium with several carbon sources that might be expected to engender complex chemostat dynamics. In such a medium, growth fueled by the substrate utilized at the highest initial efficiency can lead to the establishment of a transient steady-state, accompanied by conversion of bacterial metabolism to utilization of other substrates. Surprisingly, the chemostat was observed to achieve simple steady state growth with a population whose absolute value varied with the concentration of bacto-tryptone. As expected from the Monod model, the initial growth constants immediately after inoculation were independent of nutrient concentration and dilution rate, and represent the intrinsic growth rates of the bacteria. Approaching steady state, the bacteria appear to "lock on" to the dilution rate while becoming nutrient limited, and their growth rates were observed to slow down. The steady state concentrations in the reactor scale with dilution rate and growth-limiting factor in a manner consistent with the simple Monod model.

Discussion of Formation of Microfabricated Fluidic Devices

I. Microfabircation Overview

The following discussion relates to formation of microfabricated fluidic devices utilizing elastomer materials, as described generally in commonly assigned U.S. patent application Ser. No. 09/826,585 filed Apr. 6, 2001, Ser, No. 09/724,784 filed Nov. 28, 2000, and Ser. No. 09/605,520, filed Jun. 27, 2000. These patent applications are hereby incorporated by reference in their entirety for all purposes. Additional details may also be found in U.S. Pat. No. 6,408,878 to Unger et al, issued Jun. 25, 2002, the entire contents of which is also hereby incorporated by reference in its entirety for all purposes.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 7 to 14B illustrate sequential steps of a first preferred method of fabricating the present microstructure, (which may be used as a pump or valve). FIGS. 15 to 25 illustrate sequential steps of a second preferred method of fabricating the present microstructure, (which also may be used as a pump or valve).

As will be explained, the preferred method of FIGS. 8 to 15B involves using pre-cured elastomer layers which are assembled and bonded. In an alternative method, each layer of elastomer may be cured "in place". In the following description "channel" refers to a recess in the elastomeric structure which can contain a flow of fluid or gas.

Referring to FIG. 8, a first micro-machined mold 10 is provided. Micromachined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

As can be seen in FIG. 9, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 21:
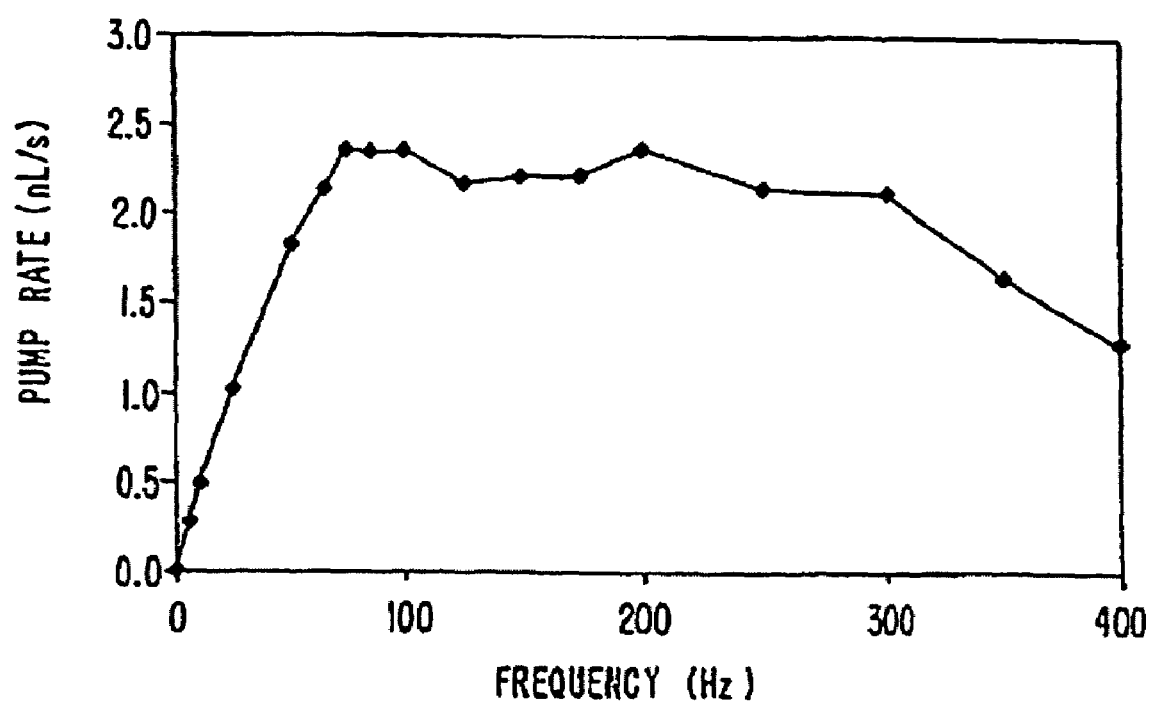
FIG. 21 is a graph showing experimentally achieved pumping rates vs. frequency for an embodiment of the peristaltic pumping system of FIG. 20.

As can be seen in the sequential steps illustrated in FIGS. 10 and 21, second elastomeric layer 22 is then removed from mold 12 and placed on top of first elastomeric layer 20. As can be seen, recess 23 extending along the bottom surface of second elastomeric layer 22 will form a flow channel 32.

Figure 12:
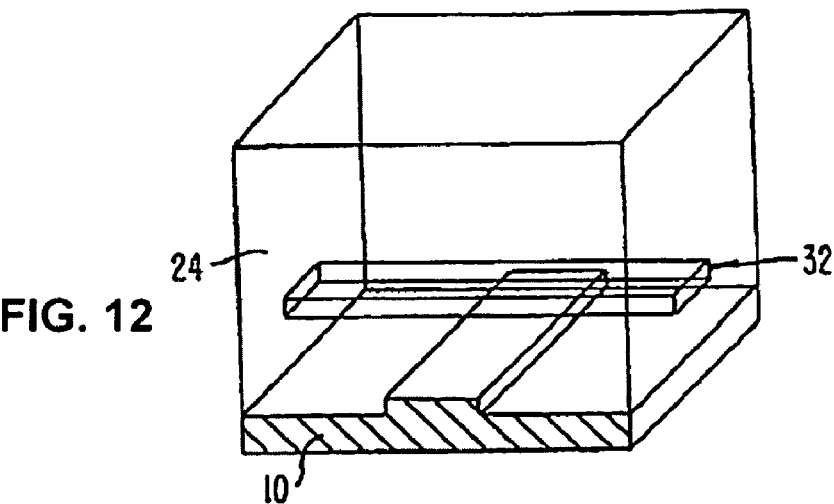
FIG. 12 is an illustration corresponding to FIG. 11, but showing the first and second elastomeric layers bonded together.

Referring to FIG. 12, the separate first and second elastomeric layers 20 and 22 (FIG. 4) are then bonded together to form an integrated (i.e.: monolithic) elastomeric structure 24.

Figure 13:
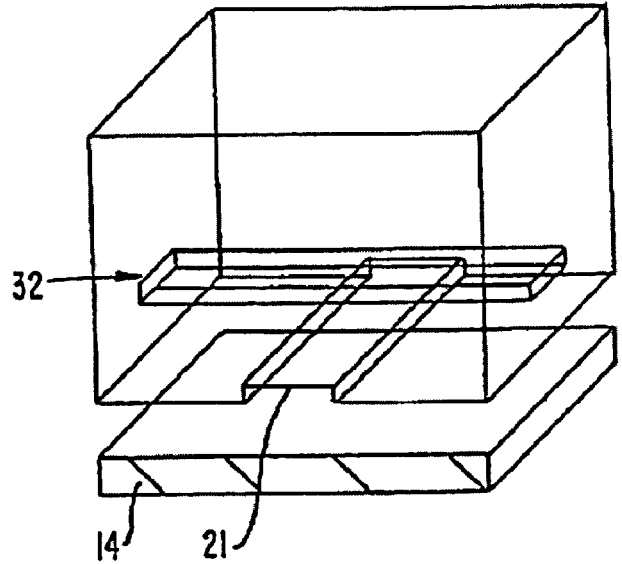
FIG. 13 is an illustration corresponding to FIG. 12, but showing the first micromachined mold removed and a planar substrate positioned in its place.
Figure 14A:
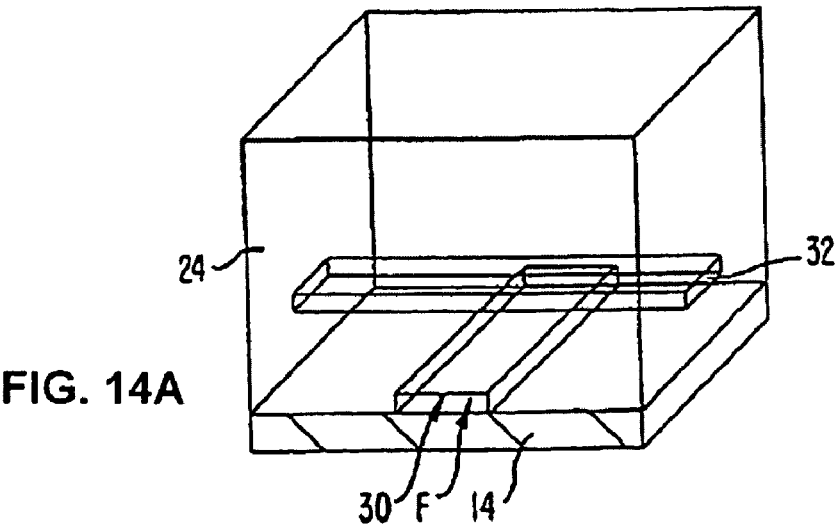
FIG. 14A is an illustration corresponding to FIG. 13, but showing the elastomeric structure sealed onto the planar substrate.
Figure 14B:
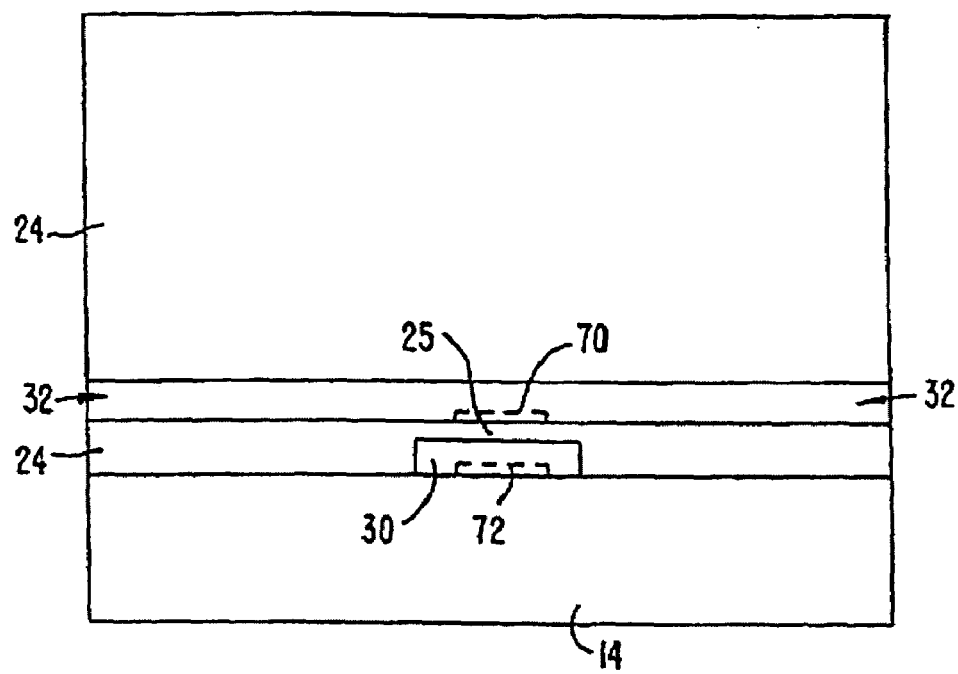
FIG. 14B is a front sectional view corresponding to FIG. 14A, showing an open flow channel.

As can been seen in the sequential step of FIGS. 13 and 14A, elastomeric structure 24 is then removed from mold 10 and positioned on top of a planar substrate 14. As can be seen in FIGS. 14A and 14B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 14A and 14B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 14C-14G.

Figure 14H:
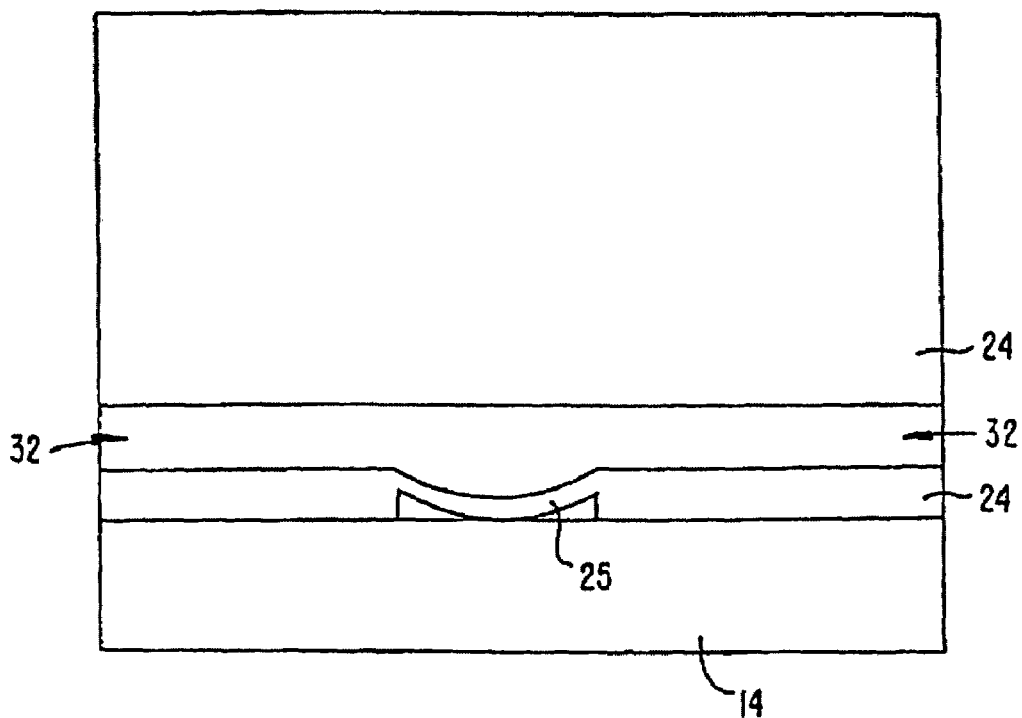
FIGS. 14C-14H are illustrations showing steps of a method for forming an elastomeric structure having a membrane formed from a separate elastomeric layer.
Figure 14C:
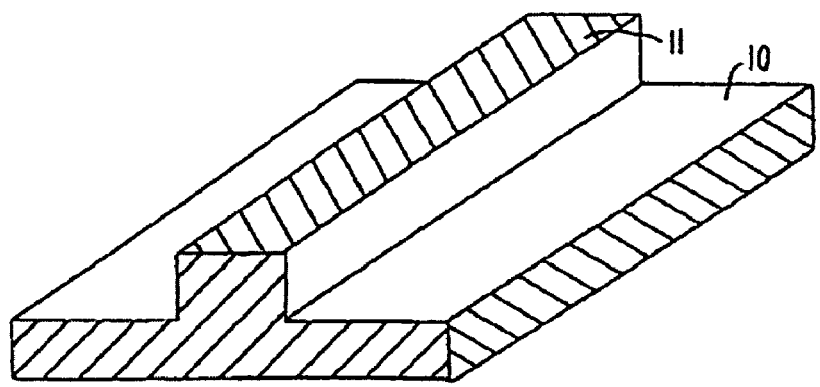
Figure 14D:
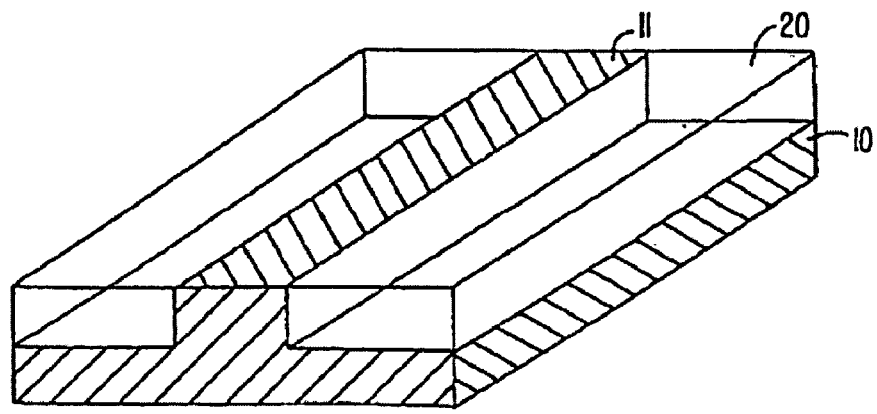

Referring to FIG. 14C, a first micro-machined mold 10 is provided. Micromachined mold 10 has a raised line or protrusion 11 extending therealong. In FIG. 14D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 14E:
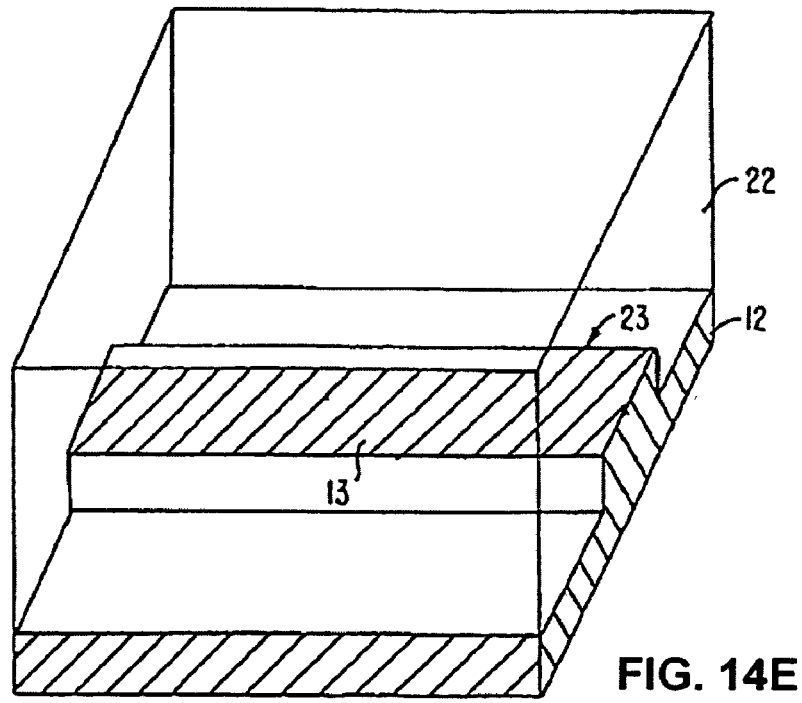

In FIG. 14E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 14F:
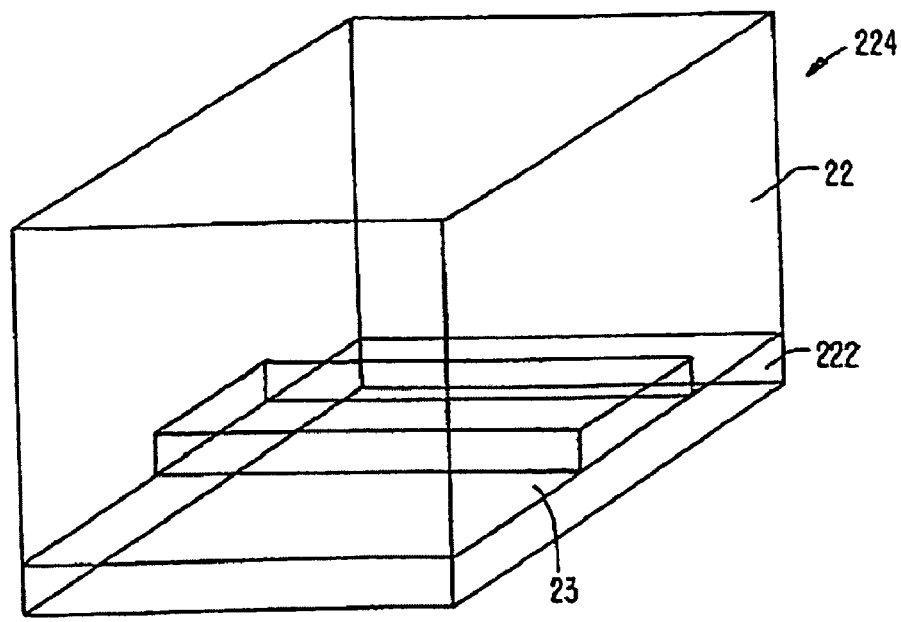

In FIG. 14F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 14G:
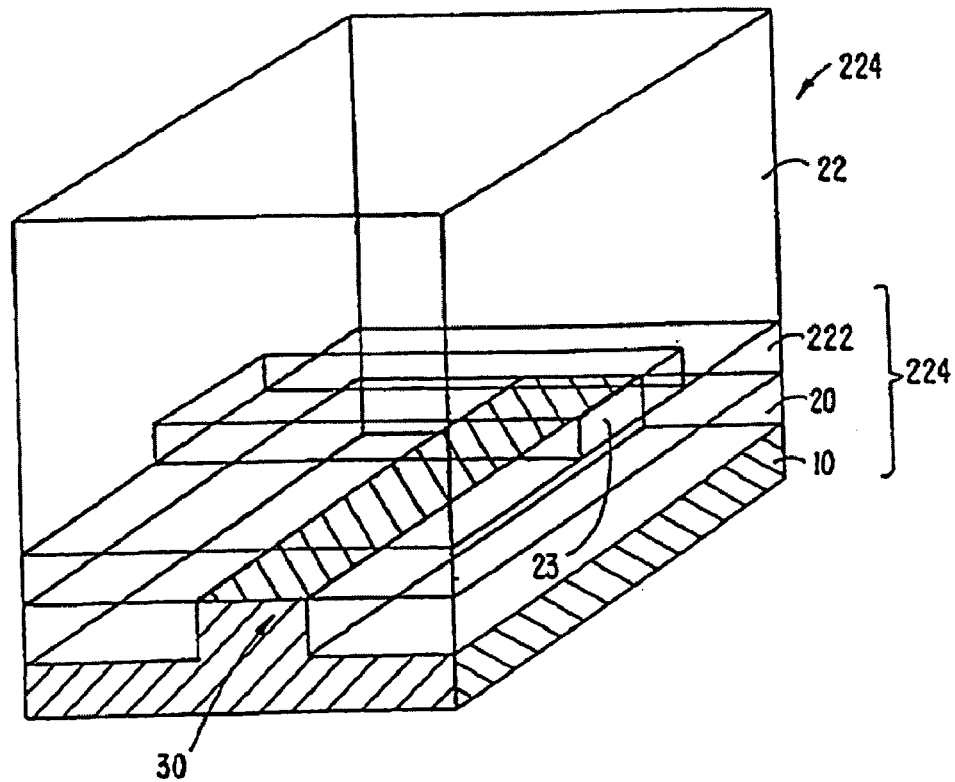

In FIG. 14G, elastomeric block 224 is placed on top of first micro-machined mold 10 and first elastomeric layer 20. Elastomeric block and first elastomeric layer 20 are then bonded together to form an integrated (i.e., monolithic) elastomeric structure 24 having a membrane composed of a separate elastomeric layer 222.

When elastomeric structure 24 has been sealed at its bottom surface to a planar substrate in the manner described above in connection with FIG. 14A, the recess formerly occupied by raised line 11 will form flow channel 30.

The variant fabrication method illustrated above in conjunction with FIGS. 14C-14G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 µm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 µm, 1 µm, 2 µm, 5 µm, 10 µm, 20 µm, 30 µm, 40 µm, 50 µm, 60 µm, 70 µm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, and 250 μm.

The flow channels are not limited to these specific dimension ranges and examples given above, and may vary in width in order to affect the magnitude of force required to deflect the membrane as discussed at length below in conjunction with FIG. 34. For example, extremely narrow flow channels having a width on the order of 0.01 m may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The Elastomeric layers may be cast thick for mechanical stability. In an exemplary embodiment, elastomeric layer 22 of FIG. 8 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 14B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 μm, 300 μm, 400 μm, 500 μm, 750 μm, and 1000 μm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e., excess vinyl groups) and the other with 3A:1B (i.e., excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly(dimethylsiloxane)", Analytical Chemistry (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 8 to 15B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, Contemporary Polymer Chemistry, 2nd Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinylsilane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, polybutadiene, polychloroprene: Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene: Pure polyisobutylene has no double bonds, but is crosslinked to use as an elastomer by including a small amount (.about 0.1%) of isoprene in the polymerization. The isoprene monomers give pendant double bonds on the polyisobutylene backbone, which may then be vulcanized as above.

Poly(styrene-butadiene-styrene): Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes: Polyurethanes are produced from di-isocyanates (A-A) and di-alcohols or diamines (B-B); since there are a large variety of di-isocyanates and dialcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones: Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 14B and 14H together show the closing of a first flow channel by pressurizing a second flow channel, with FIG. 14B (a front sectional view cutting through flow channel 32 in corresponding FIG. 14A), showing an open first flow channel 30; with FIG. 14H showing first flow channel 30 closed by pressurization of the second flow channel 32.

Referring to FIG. 14B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 14H, pressurization of flow channel 32 (either by gas or liquid introduced therein) causes membrane 25 to deflect downward, thereby pinching off flow F passing through channel 30. Accordingly, by varying the pressure in channel 32, a linearly actuable valving system is provided such that flow channel 30 can be opened or closed by moving membrane 25 as desired. (For illustration purposes only, channel 30 in FIG. 14G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 μm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 μL, 100 aL to 100 nL, 1 fl to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 μl. The smallest known volumes capable of being metered by automated systems is about ten-times larger (1 μl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$w=(BPb^4)/(Eh^3)$, where w=deflection of plate;
B=shape coefficient (dependent upon length vs. width and support of edges of plate);
P=applied pressure;
b=plate width
E=Young's modulus; and
h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticities, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 15A:
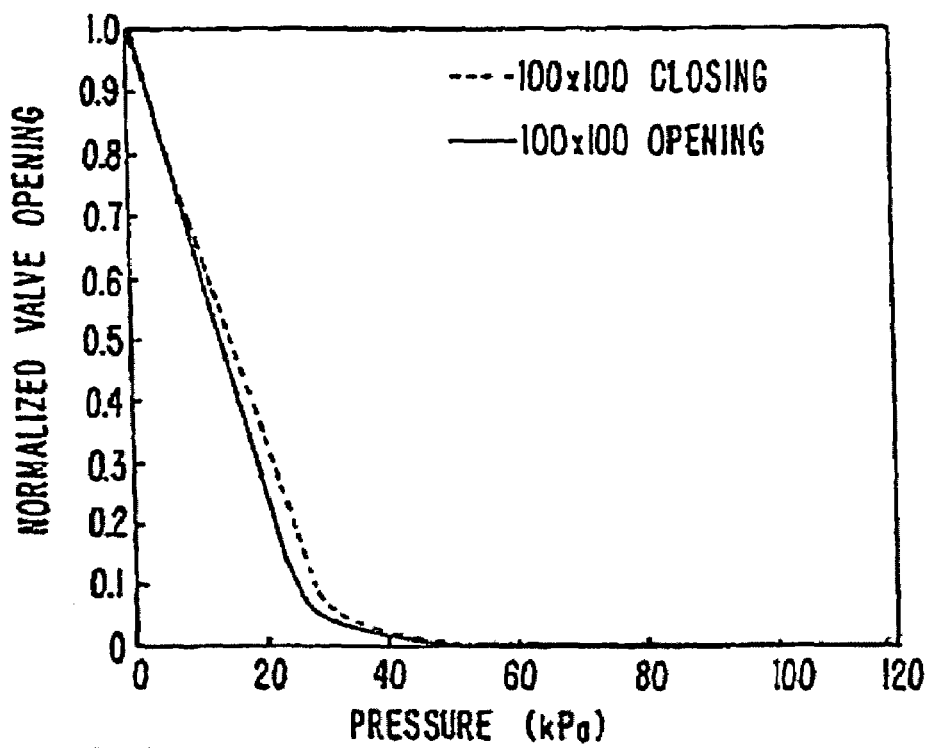
FIGS. 15A and 15B illustrates valve opening vs. applied pressure for various flow channels.
Figure 15B:
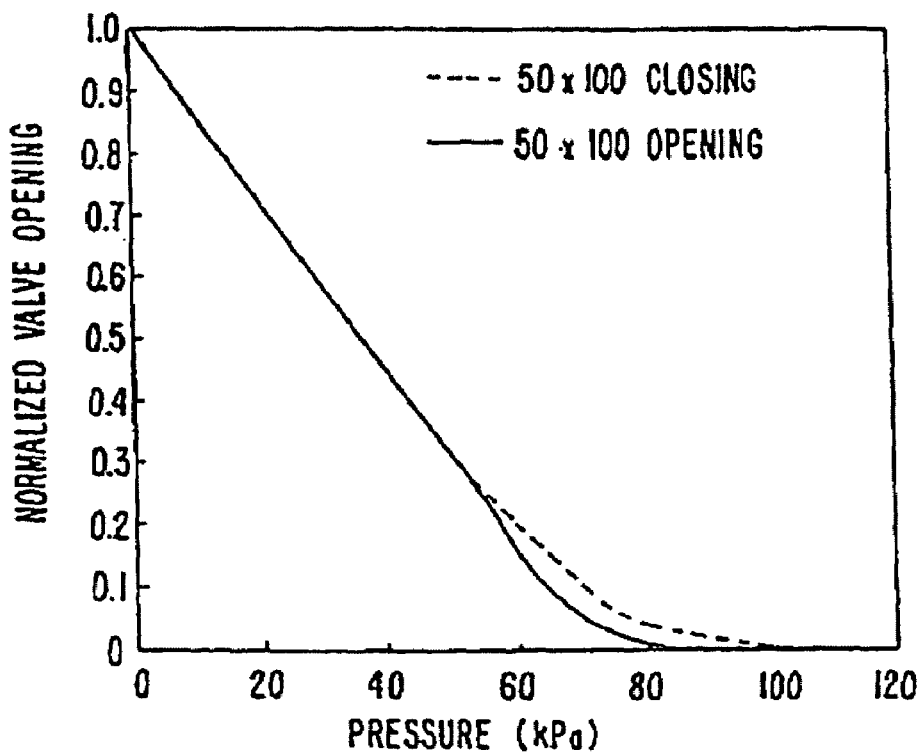

FIGS. 15A and 15B illustrate valve opening vs. applied pressure for a 100 μm wide first flow channel 30 and a 50 μm wide second flow channel 32. The membrane of this device was formed by a layer of General Electric Silicones RTV 615 having a thickness of approximately 30 μm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a non-compressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebro-spinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and nonlinearly actuable valves are contemplated in the present invention, and the pressure ranges over which a valve is linearly actuable will vary with the specific embodiment.

Figure 16:
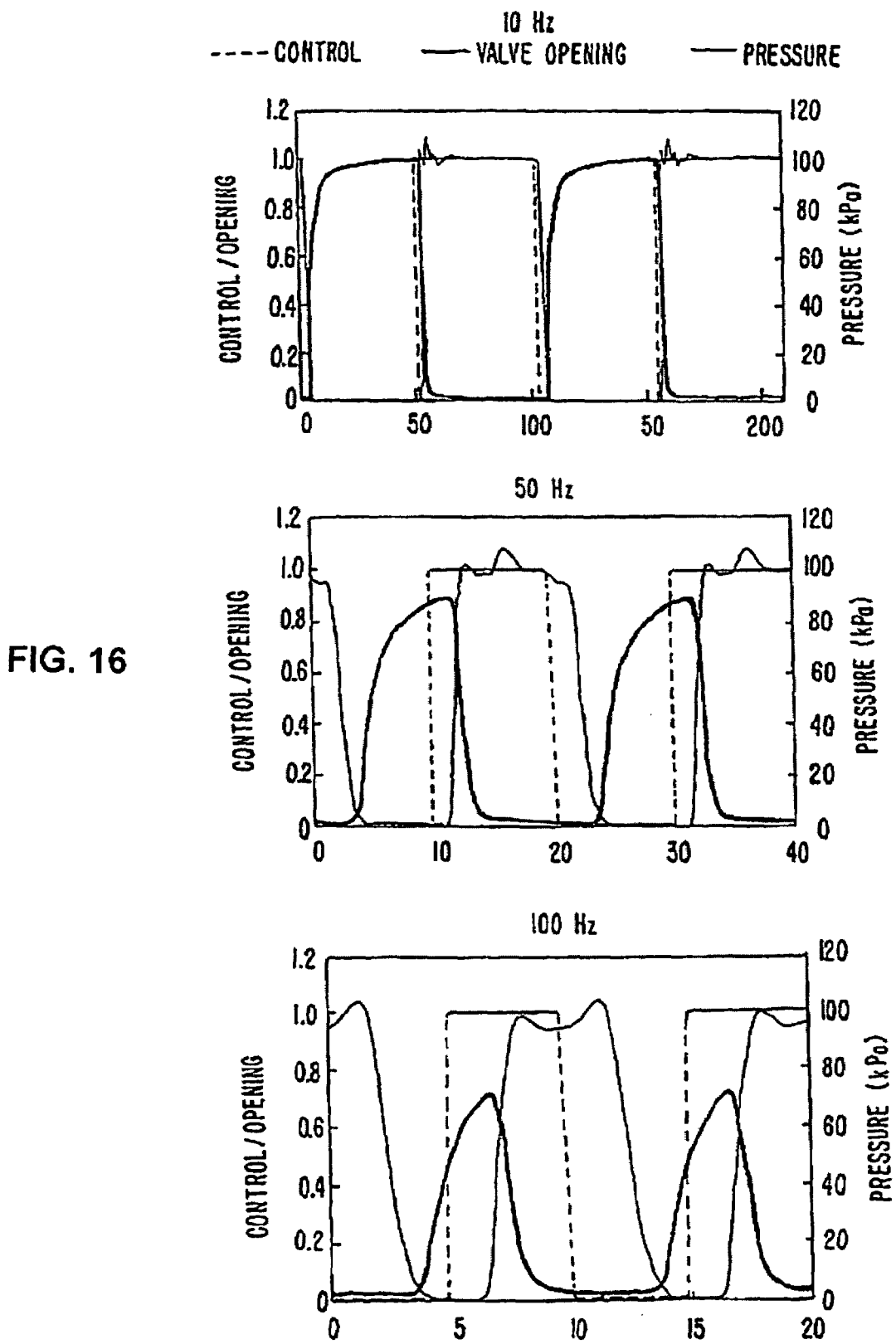
FIG. 16 illustrates time response of a 100 μm×100 μm×100 μm RTV microvalve.

FIG. 16 illustrates time response (i.e.: closure of valve as a function of time in response to a change in applied pressure) of a 100 μm×100 μm×100 μm RTV microvalve with 10-cm-long air tubing connected from the chip to a pneumatic valve as described above.

Two periods of digital control signal, actual air pressure at the end of the tubing and valve opening are shown in FIG. 16. The pressure applied on the control line is 100 kPa, which is substantially higher than the 40 kPa required to close the valve. Thus, when closing, the valve is pushed closed with a pressure 60 kPa greater than required. When opening, however, the valve is driven back to its rest position only by its own spring force (.ltoreq.40 kPa). Thus, $\tau_{close}$ is expected to be smaller than $\tau_{open}$. There is also a lag between the control signal and control pressure response, due to the limitations of the miniature valve used to control the pressure. Calling such lags t and the 1/e time constants τ, the values are: $\tau_{open}$=3.63 ms, $\tau_{open}$=1.88 ms, $\tau_{close}$=2.15 ms, $\tau_{close}$=0.51 ms. If 3τ each are allowed for opening and closing, the valve runs comfortably at 75 Hz when filled with aqueous solution.

If one used another actuation method which did not suffer from opening and closing lag, this valve would run at about 375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 14C-14H.).

When experimentally measuring the valve properties as illustrated in FIG. 16 the valve opening was measured by fluorescence. In these experiments, the flow channel was filled with a solution of fluorescein isothiocyanate (FITC) in buffer (pH 8) and the fluorescence of a square area occupying the center .about.{fraction (⅓)}rd of the channel is monitored on an epi-fluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Figure 17:
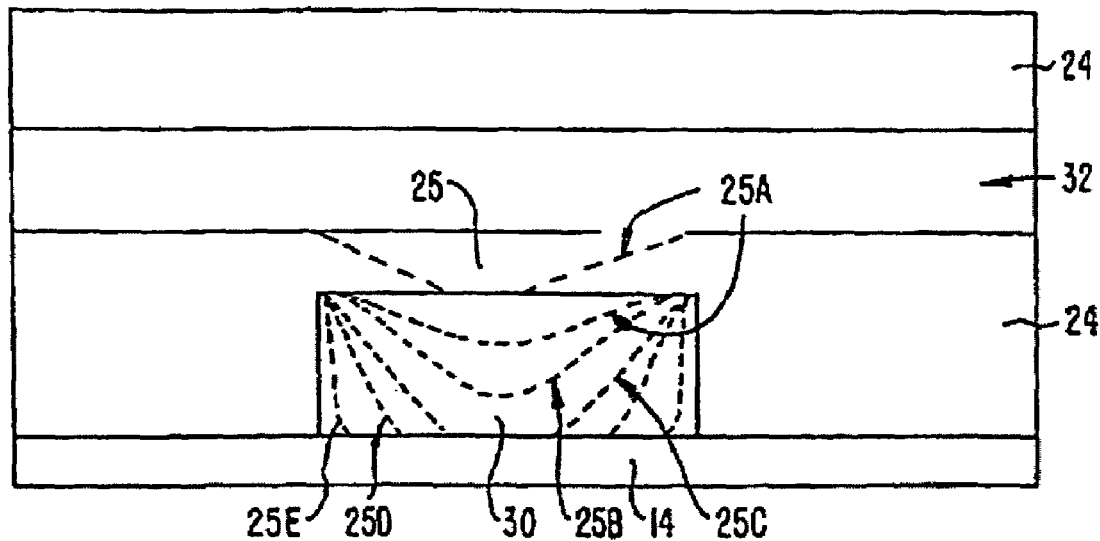
FIG. 17 illustrates a cross-sectional view of a flow-channel through a pair of flow channels.

Referring to FIG. 17, a cross sectional view (similar to that of FIG. 14B) through flow channels 30 and 32 is shown. As can be seen, flow channel 30 is rectangular in cross sectional shape. In an alternate preferred aspect of the invention, as shown in FIG. 27, the cross-section of a flow channel 30 instead has an upper curved surface.

Referring first to FIG. 17, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

Figure 18:
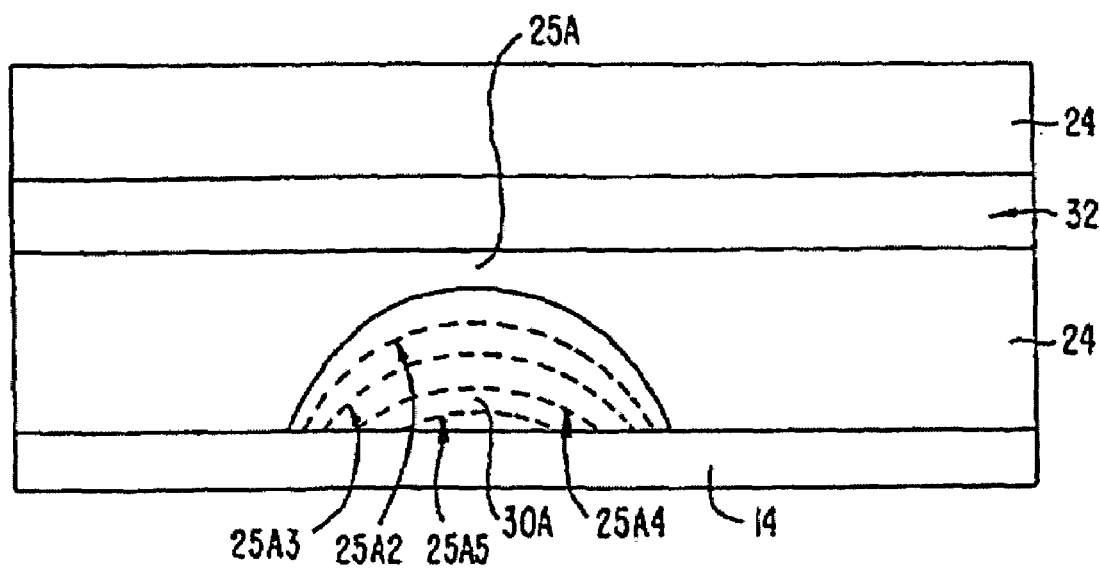
FIG. 18 illustrates a cross-sectional view of a flow channel with a curved upper wall.

In the alternate preferred embodiment of FIG. 18, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 17.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel.

In an alternate aspect, (not illustrated), the bottom of flow channel 30 is rounded such that its curved surface mates with the curved upper wall 25A as seen in FIG. 27 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Alternate Valve Actuation Techniques

In addition to pressure based actuation systems described above, optional electrostatic and magnetic actuation systems are also contemplated, as follows.

Electrostatic actuation can be accomplished by forming oppositely charged electrodes (which will tend to attract one another when a voltage differential is applied to them) directly into the monolithic elastomeric structure. For example, referring to FIG. 14B, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e.: closing flow channel 30).

For the membrane electrode to be sufficiently conductive to support electrostatic actuation, but not so mechanically stiff so as to impede the valve's motion, a sufficiently flexible electrode must be provided in or over membrane 25. Such an electrode may be provided by a thin metallization layer, doping the polymer with conductive material, or making the surface layer out of a conductive material.

In an exemplary aspect, the electrode present at the deflecting membrane can be provided by a thin metallization layer which can be provided, for example, by sputtering a thin layer of metal such as 20 nm of gold. In addition to the formation of a metallized membrane by sputtering, other metallization approaches such as chemical epitaxy, evaporation, electroplating, and electroless plating are also available. Physical transfer of a metal layer to the surface of the elastomer is also available, for example by evaporating a metal onto a flat substrate to which it adheres poorly, and then placing the elastomer onto the metal and peeling the metal off of the substrate.

A conductive electrode 70 may also be formed by depositing carbon black (i.e. Cabot Vulcan XC72R) on the elastomer surface, either by wiping on the dry powder or by exposing the elastomer to a suspension of carbon black in a solvent which causes swelling of the elastomer, (such as a chlorinated solvent in the case of PDMS). Alternatively, the electrode 70 may be formed by constructing the entire layer 20 out of elastomer doped with conductive material (i.e. carbon black or finely divided metal particles). Yet further alternatively, the electrode may be formed by electrostatic deposition, or by a chemical reaction that produces carbon. In experiments conducted by the present inventors, conductivity was shown to increase with carbon black concentration from $5.6 \times 10^{-16}$ to about $5 \times 10^{-3}$ $(\Omega\text{-cm})^{-1}$. The lower electrode 72, which is not required to move, may be either a compliant electrode as described above, or a conventional electrode such as evaporated gold, a metal plate, or a doped semiconductor electrode.

Magnetic actuation of the flow channels can be achieved by fabricating the membrane separating the flow channels with a magnetically polarizable material such as iron, or a permanently magnetized material such as polarized NdFeB. In experiments conducted by the present inventors, magnetic silicone was created by the addition of iron powder (about 1 um particle size), up to 20% iron by weight.

Where the membrane is fabricated with a magnetically polarizable material, the membrane can be actuated by attraction in response to an applied magnetic field Where the membrane is fabricated with a material capable of maintaining permanent magnetization, the material can first be magnetized by exposure to a sufficiently high magnetic field, and then actuated either by attraction or repulsion in response to the polarity of an applied inhomogenous magnetic field.

The magnetic field causing actuation of the membrane can be generated in a variety of ways. In one embodiment, the magnetic field is generated by an extremely small inductive coil formed in or proximate to the elastomer membrane. The actuation effect of such a magnetic coil would be localized, allowing actuation of individual pump and/or valve structures. Alternatively, the magnetic field could be generated by a larger, more powerful source, in which case actuation would be global and would actuate multiple pump and/or valve structures at one time.

It is also possible to actuate the device by causing a fluid flow in the control channel based upon the application of thermal energy, either by thermal expansion or by production of gas from liquid. For example, in one alternative embodiment in accordance with the present invention, a pocket of fluid (e.g. in a fluid-filled control channel) is positioned over the flow channel. Fluid in the pocket can be in communication with a temperature variation system, for example a heater. Thermal expansion of the fluid, or conversion of material from the liquid to the gas phase, could result in an increase in pressure, closing the adjacent flow channel. Subsequent cooling of the fluid would relieve pressure and permit the flow channel to open.

8. Networked Systems

Figure 19A:
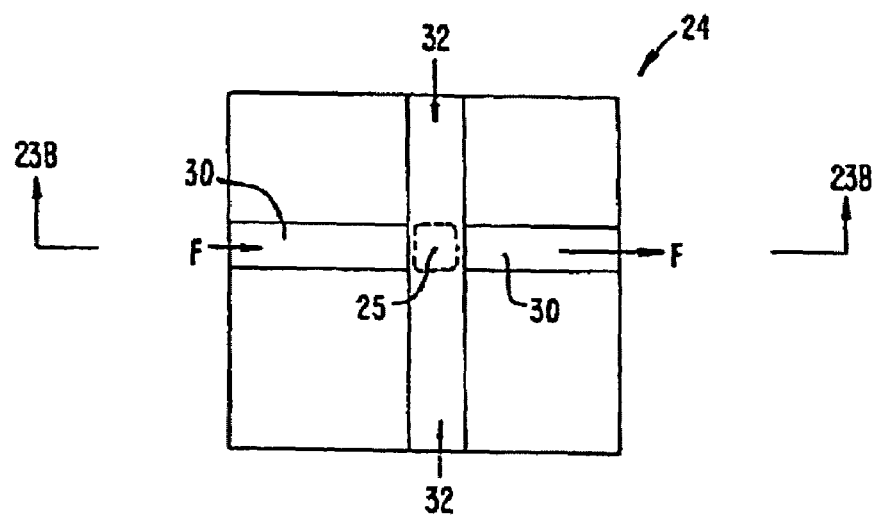
FIG. 19A is a top schematic view of an on/off valve.
Figure 20A:
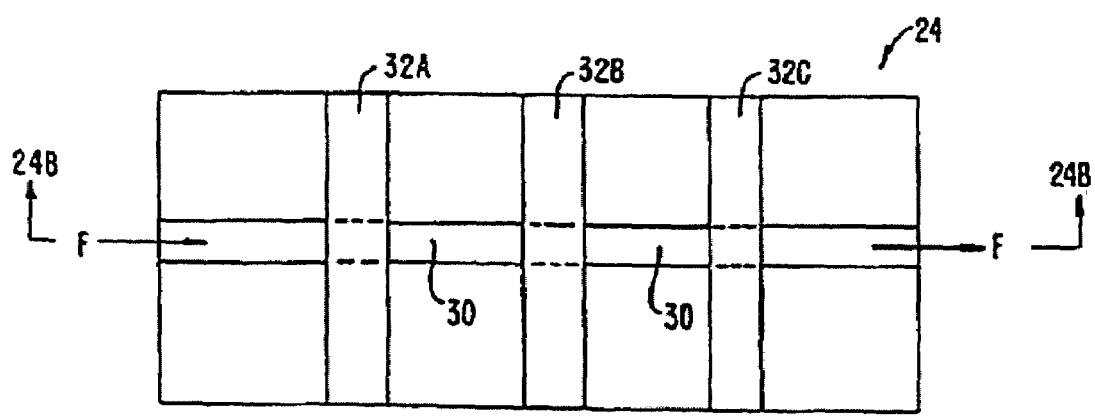
FIG. 20A is a top schematic view of a peristaltic pumping system.
Figure 19B:
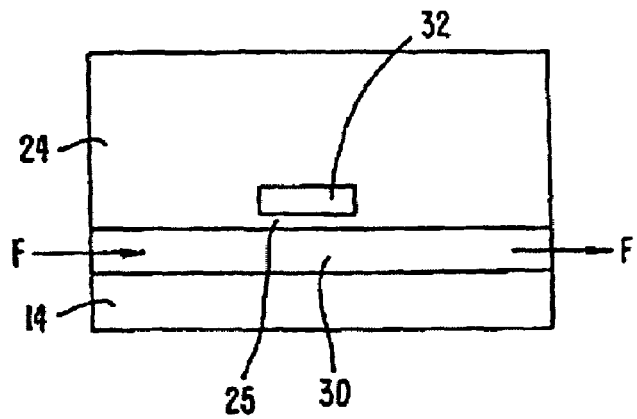
FIG. 19B is a sectional elevation view along line 30B-30B in FIG. 19A.
Figure 20B:
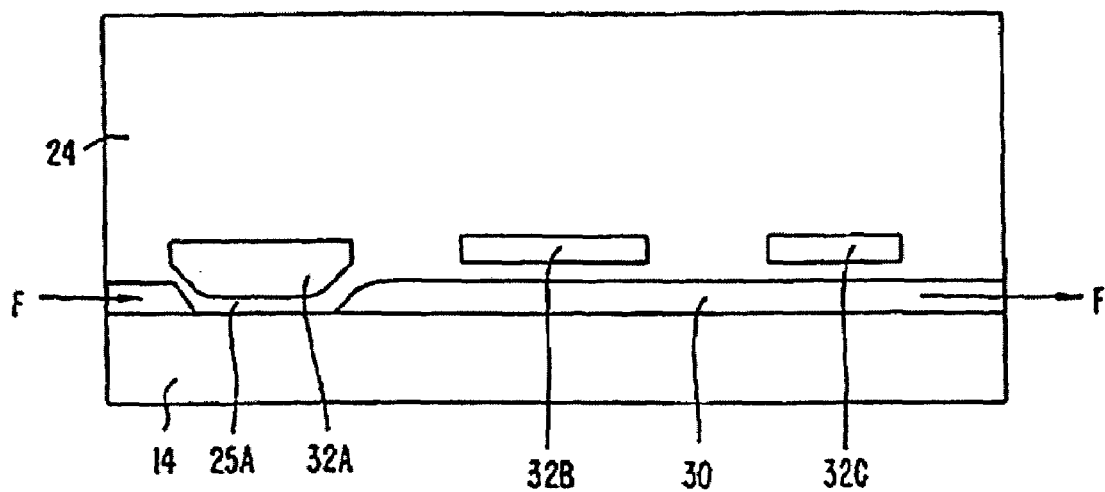
FIG. 20B is a sectional elevation view along line 31B-31B in FIG. 20A
Figure 22A:
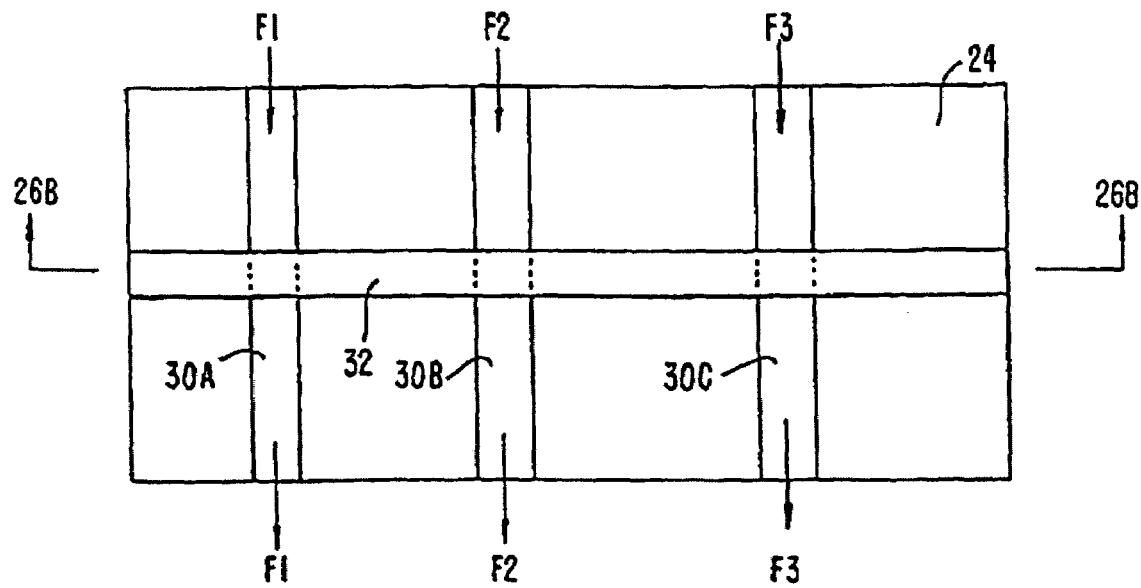
FIG. 22A is a top schematic view of one control line actuating multiple flow lines simultaneously.
Figure 23:
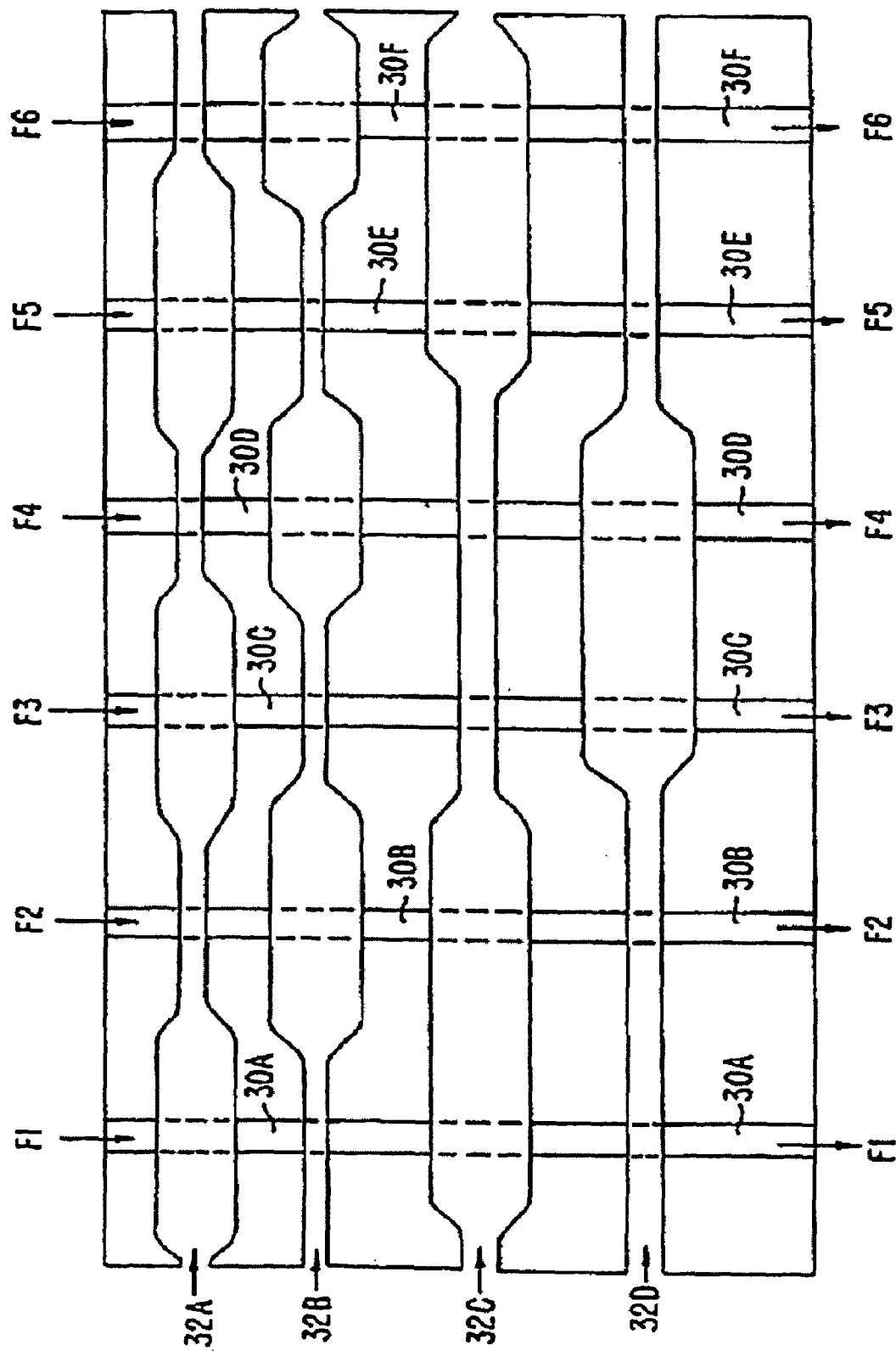
FIG. 23 is a schematic illustration of a multiplexed system adapted to permit flow through various channels.
Figure 24A:
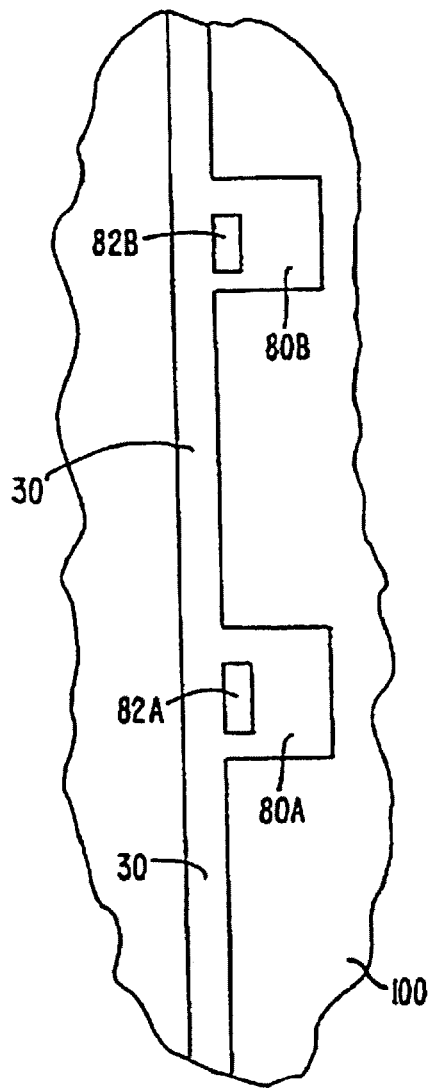
FIG. 24A is a plan view of a flow layer of an addressable reaction chamber structure.
Figure 24B:
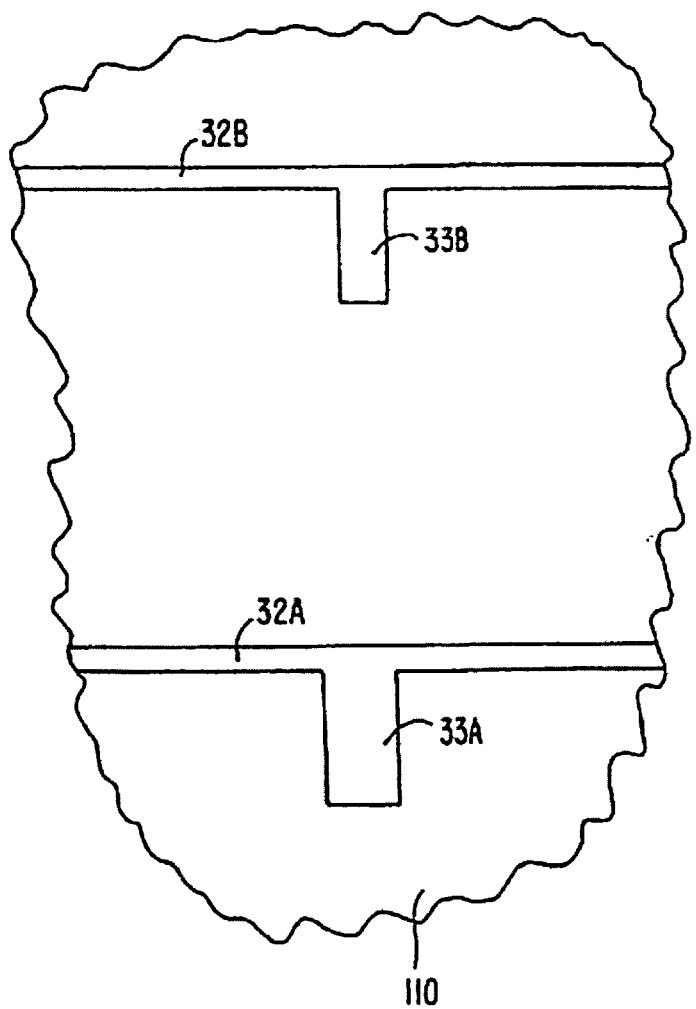
FIG. 24B is a bottom plan view of a control channel layer of an addressable reaction chamber structure.
Figure 24C:
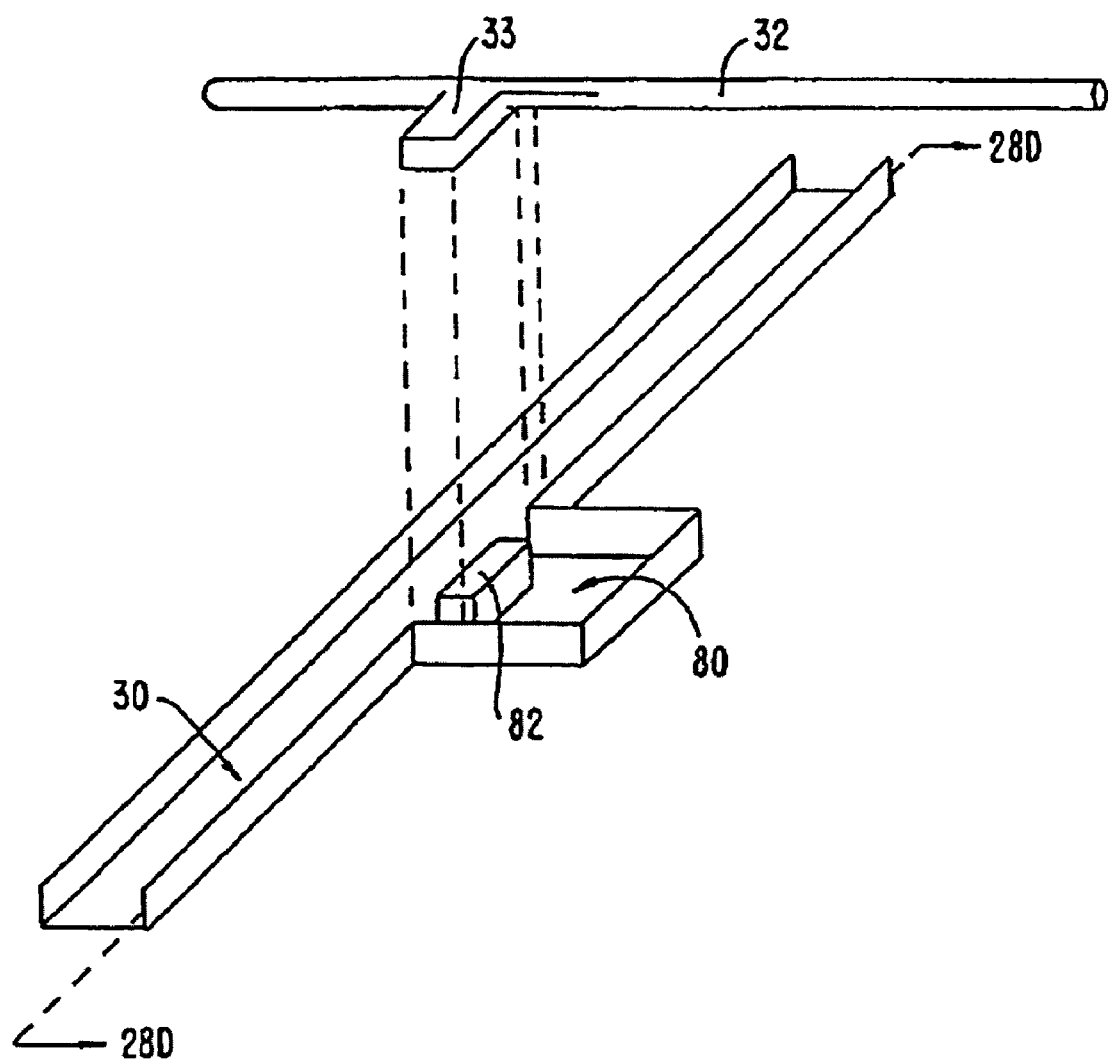
FIG. 24C is an exploded perspective view of the addressable reaction chamber structure formed by bonding the control channel layer of FIG. 24B to the top of the flow layer of FIG. 24A.
Figure 24D:
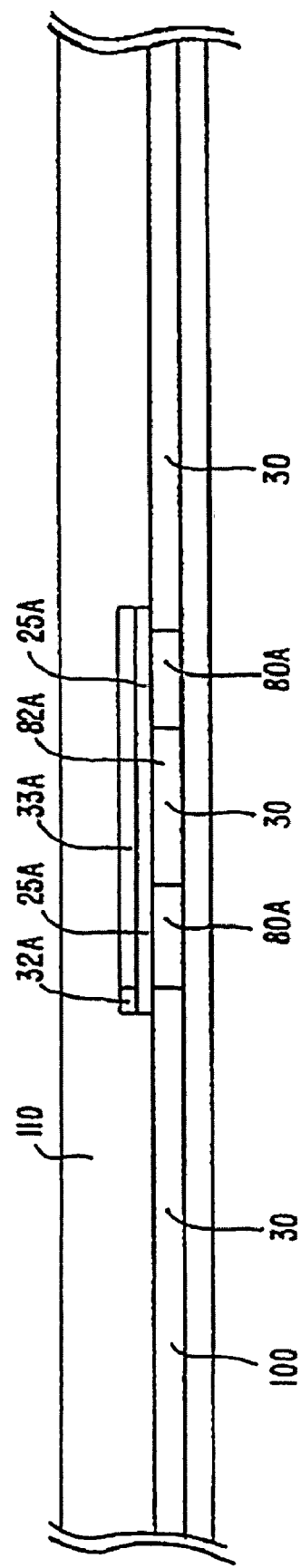
FIG. 24D is a sectional elevation view corresponding to FIG. 24C, taken along line 25D-25D in FIG. 24C.
Figure 25:
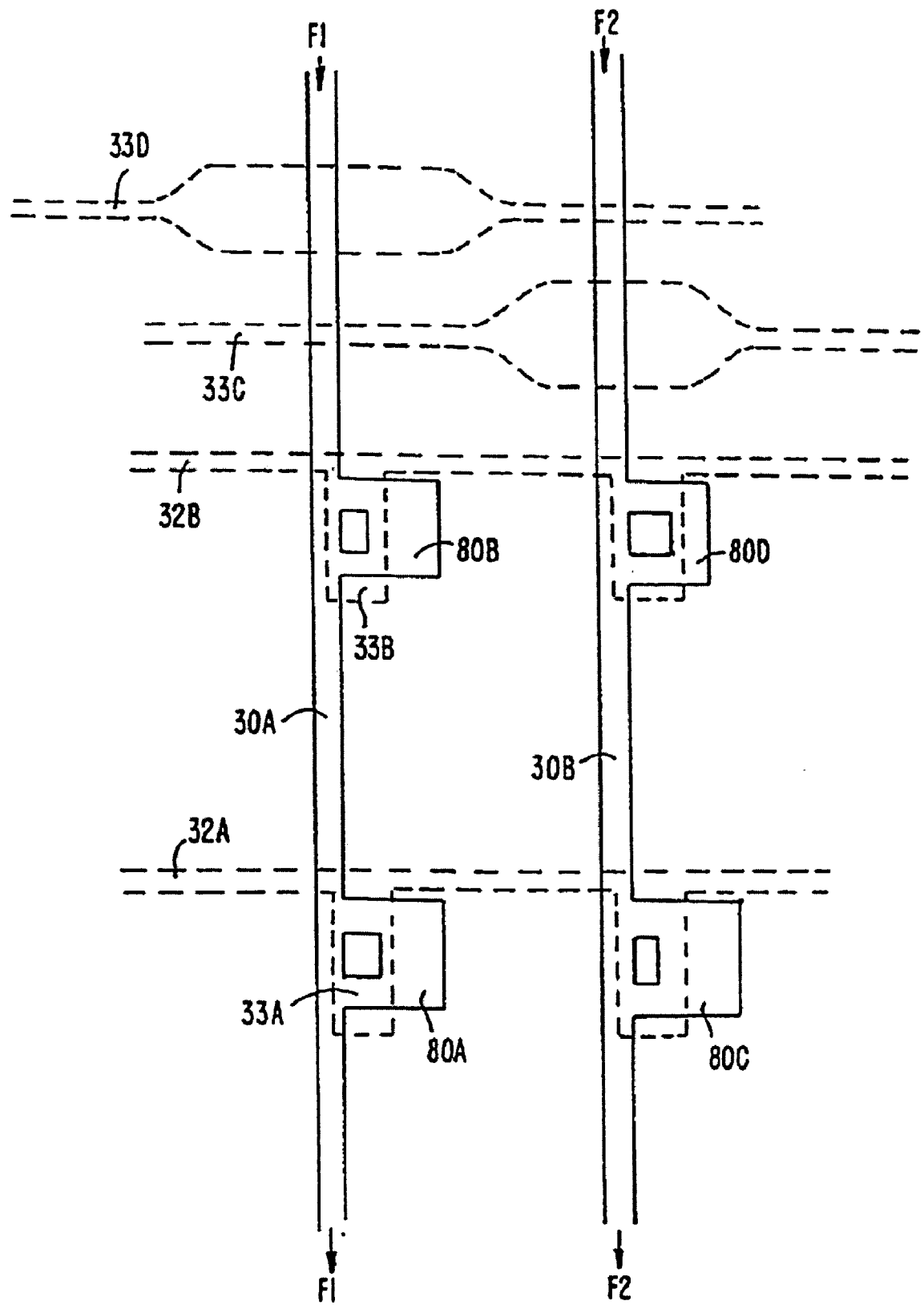
FIG. 25 is a schematic of a system adapted to selectively direct fluid flow into any of an array of reaction wells.

FIGS. 19A and 19B show a views of a single on/off valve, identical to the systems set forth above, (for example in FIG. 14A). FIGS. 20A and 20B shows a peristaltic pumping system comprised of a plurality of the single addressable on/off valves as seen in FIG. 19, but networked together. FIG. 21 is a graph showing experimentally achieved pumping rates vs. frequency for the peristaltic pumping system of FIG. 20. FIGS. 22A and 1 SB show a schematic view of a plurality of flow channels which are controllable by a single control line. This system is also comprised of a plurality of the single addressable on/off valves of FIG. 19, multiplexed together, but in a different arrangement than that of FIG. 19. FIG. 23 is a schematic illustration of a multiplexing system adapted to permit fluid flow through selected channels, comprised of a plurality of the single on/off valves of FIG. 19, joined or networked together.

Referring first to FIGS. 19A and 19B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 19 to 22, a plurality of such addressable valves are joined or networked together in various arrangements to produce pumps, capable of peristaltic pumping, and other fluidic logic applications.

Referring to FIGS. 20A and 20B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×1100×10 μm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of E. coli pumped through a channel and tested for viability showed a 94% survival rate.

FIG. 21 is a graph showing experimentally achieved pumping rates vs. frequency for the peristaltic pumping system of FIG. 20.

Figure 22B:
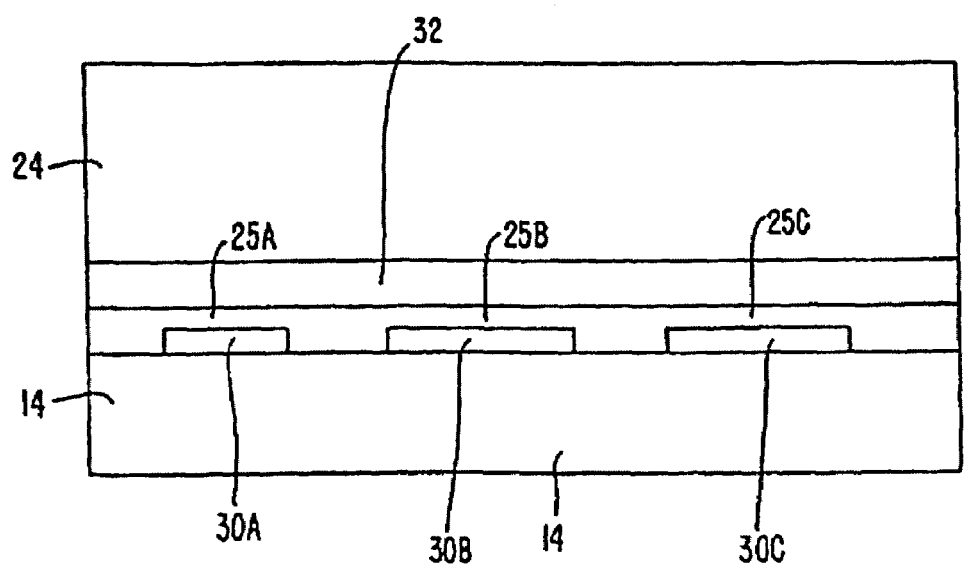
FIG. 22B is a sectional elevation view along line 33B-33B in FIG. 21A

FIGS. 22A and 22B illustrates another way of assembling a plurality of the addressable valves of FIG. 19. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 23 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 22A and 22B) depends strongly upon the membrane dimensions. Accordingly, by varying the widths of flow channel control line 32 in FIGS. 22A and 22B, it is possible to have a control line pass over multiple flow channels, yet only actuate (i.e.: seal) desired flow channels. FIG. 23 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only $2(\log_2 n)$ control lines.

9. Selectively Addressable Reaction Chambers Along Flow Lines

In a further embodiment of the invention, illustrated in FIGS. 26A, 26B, 26C and 26D, a system for selectively directing fluid flow into one more of a plurality of reaction chambers disposed along a flow line is provided.

FIG. 26A shows a top view of a flow channel 30 having a plurality of reaction chambers 80A and 80B disposed therealong. Preferably flow channel 30 and reaction chambers 80A and 80B are formed together as recesses into the bottom surface of a first layer 100 of elastomer.

FIG. 26B shows a bottom plan view of another elastomeric layer 110 with two control lines 32A and 32B each being generally narrow, but having wide extending portions 33A and 33B formed as recesses therein.

As seen in the exploded view of FIG. 26C, and assembled view of FIG. 26D, elastomeric layer 110 is placed over elastomeric layer 100. Layers 100 and 110 are then bonded together, and the integrated system operates to selectively direct fluid flow F (through flow channel 30) into either or both of reaction chambers 80A and 80B, as follows. Pressurization of control line 32A will cause the membrane 25 (i.e.: the thin portion of elastomer layer 100 located below extending portion 33A and over regions 82A of reaction chamber 80A) to become depressed, thereby shutting off fluid flow passage in regions 82A, effectively sealing reaction chamber 80 from flow channel 30. As can also be seen, extending portion 33A is wider than the remainder of control line 32A. As such, pressurization of control line 32A will not result in control line 32A sealing flow channel 30.

As can be appreciated, either or both of control lines 32A and 32B can be actuated at once. When both control lines 32A and 32B are pressurized together, sample flow in flow channel 30 will enter neither of reaction chambers 80A or 80B.

The concept of selectably controlling fluid introduction into various addressable reaction chambers disposed along a flow line (FIGS. 24A-D) can be combined with concept of selectably controlling fluid flow through one or more of a plurality of parallel flow lines (FIG. 23) to yield a system in which a fluid sample or samples can be can be sent to any particular reaction chamber in an array of reaction chambers. An example of such a system is provided in FIG. 25, in which parallel control channels 32A, 32B and 32C with extending portions 34 (all shown in phantom) selectively direct fluid flows F1 and F2 into any of the array of reaction wells 80A, 80B, 80C or 80D as explained above; while pressurization of control lines 32C and 32D selectively shuts off flows F2 and F1, respectively.

Figure 26:
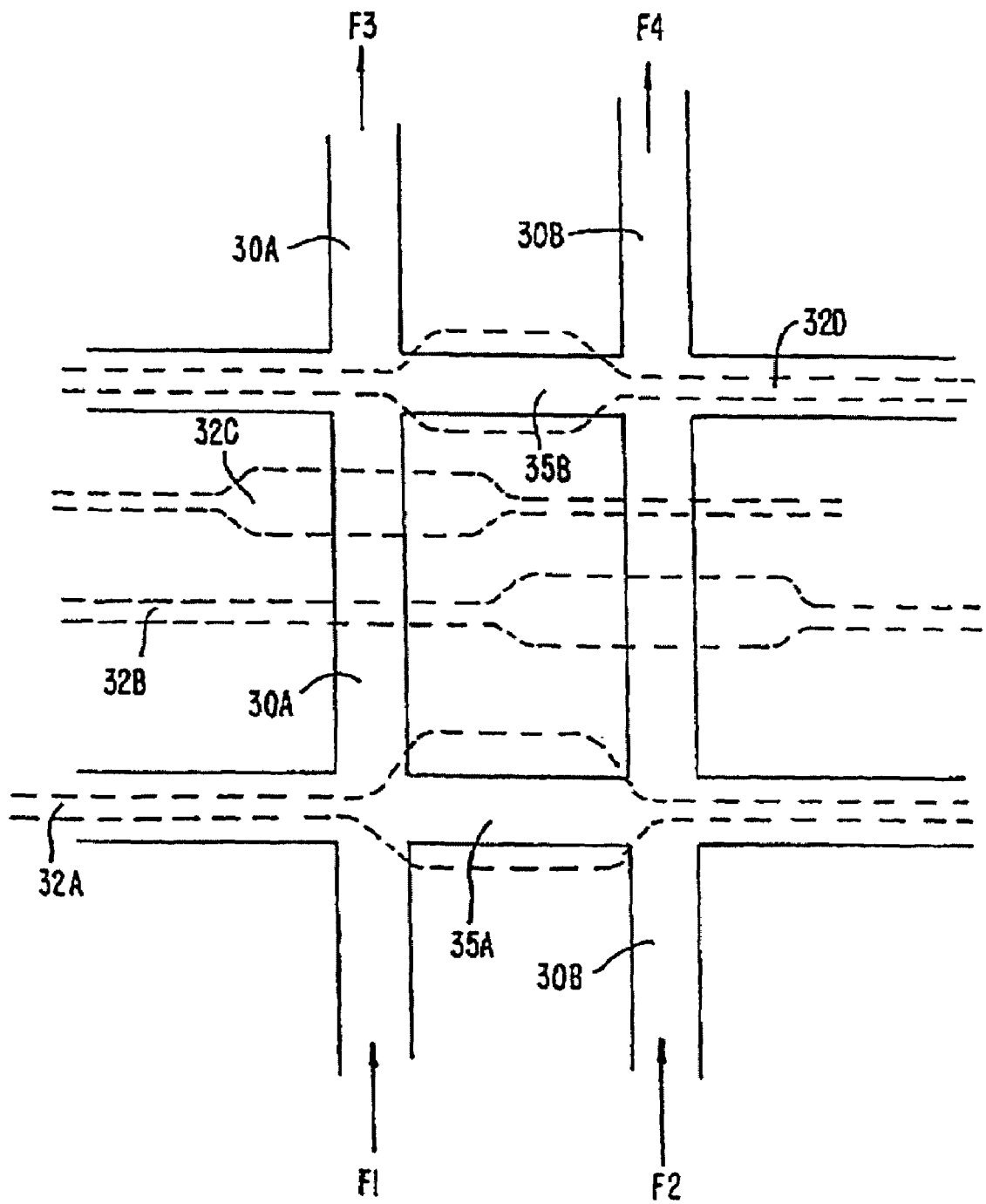
FIG. 26 is a schematic of a system adapted for selectable lateral flow between parallel flow channels.

In yet another novel embodiment, fluid passage between parallel flow channels is possible. Referring to FIG. 26, either or both of control lines 32A or 32D can be depressurized such that fluid flow through lateral passageways 35 (between parallel flow channels 30A and 30B) is permitted. In this aspect of the invention, pressurization of control lines 32C and 32D would shut flow channel 30A between 35A and 35B, and would also shut lateral passageways 35B. As such, flow entering as flow F1 would sequentially travel through 30A, 35A and leave 30B as flow F4.

10. Switchable Flow Arrays

Figure 27A:
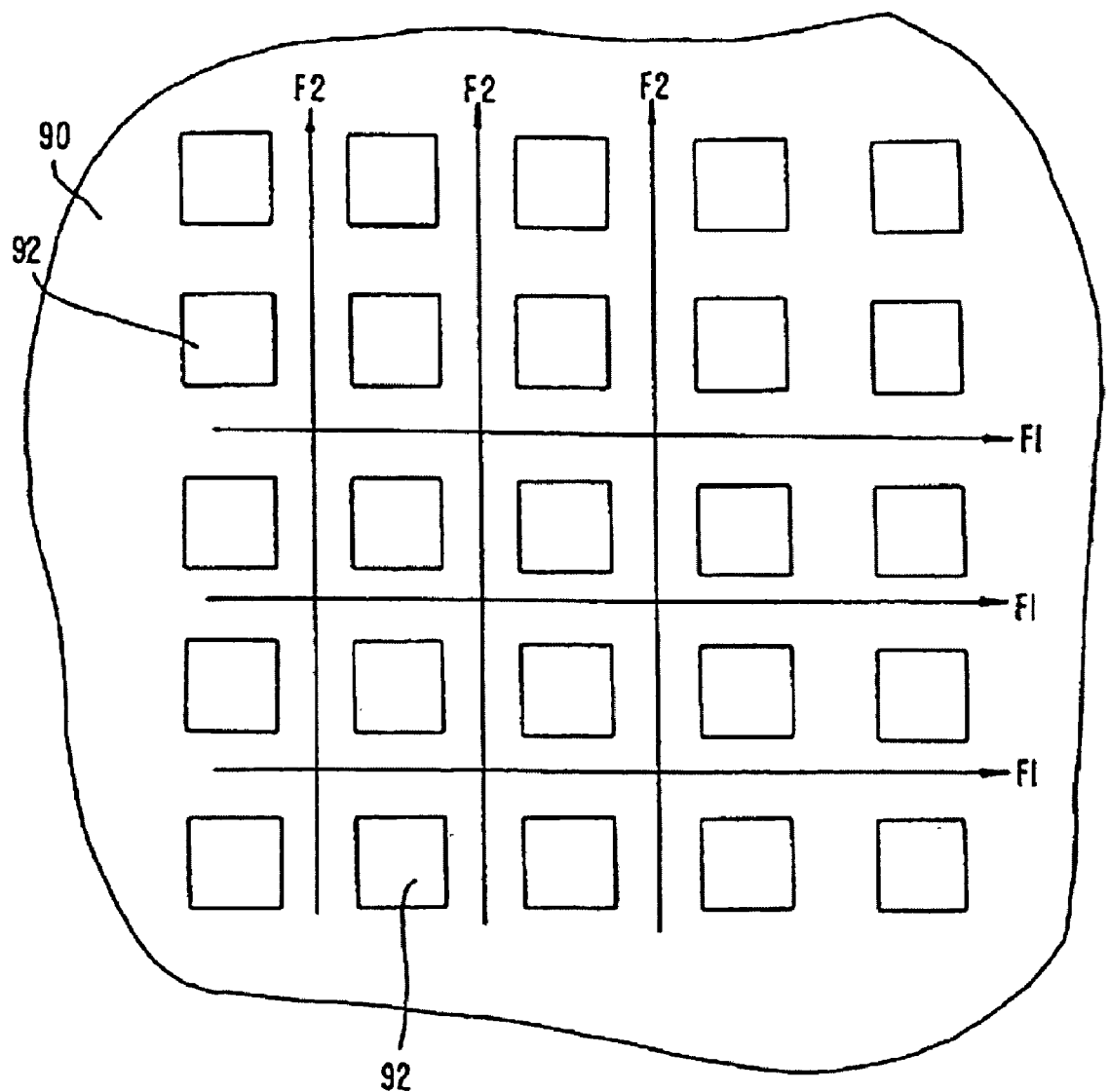
FIG. 27A is a bottom plan view of first layer (i.e.: the flow channel layer) of elastomer of a switchable flow array.
Figure 27B:
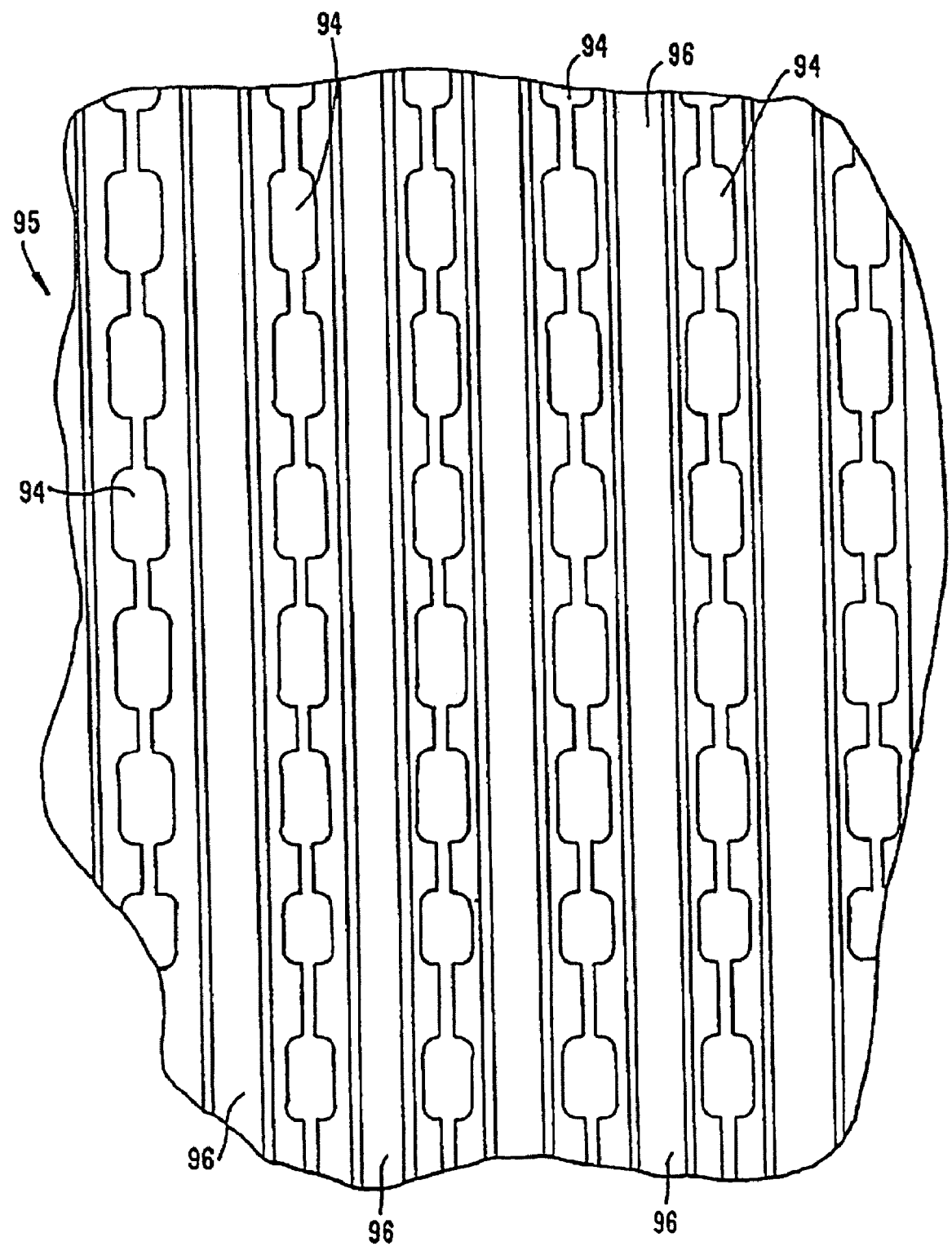
FIG. 27B is a bottom plan view of a control channel layer of a switchable flow array.

In yet another novel embodiment, fluid passage can be selectively directed to flow in either of two perpendicular directions. An example of such a "switchable flow array" system is provided in FIGS. 27A to 27D. FIG. 27A shows a bottom view of a first layer of elastomer 90, (or any other suitable substrate), having a bottom surface with a pattern of recesses forming a flow channel grid defined by an array of solid posts 92, each having flow channels passing therearound.

In preferred aspects, an additional layer of elastomer is bound to the top surface of layer 90 such that fluid flow can be selectively directed to move either in direction F1, or perpendicular direction F2. FIG. 27 is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 27C:
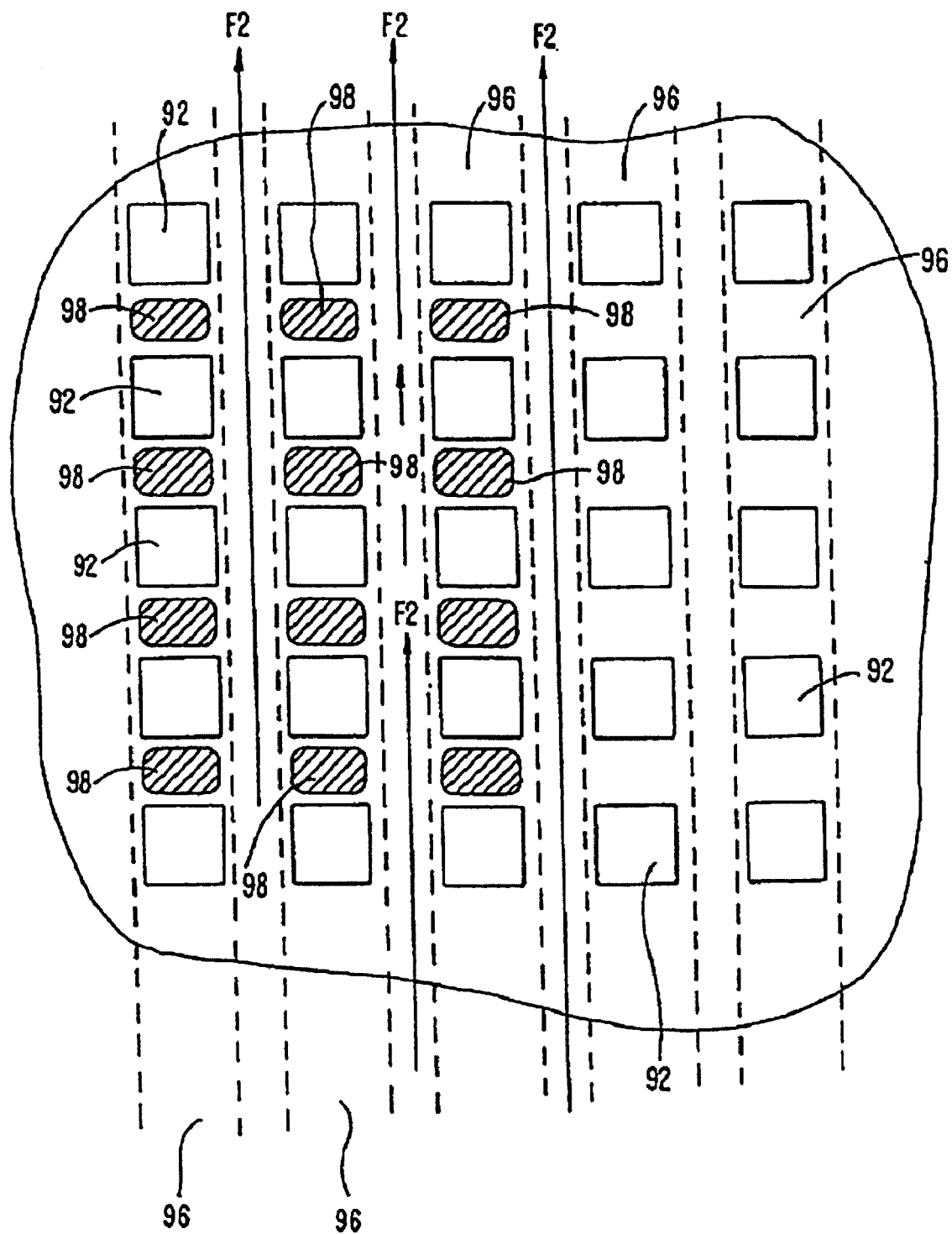
FIG. 27C shows the alignment of the first layer of elastomer of FIG. 27A with one set of control channels in the second layer of elastomer of FIG. 27B.
Figure 27D:
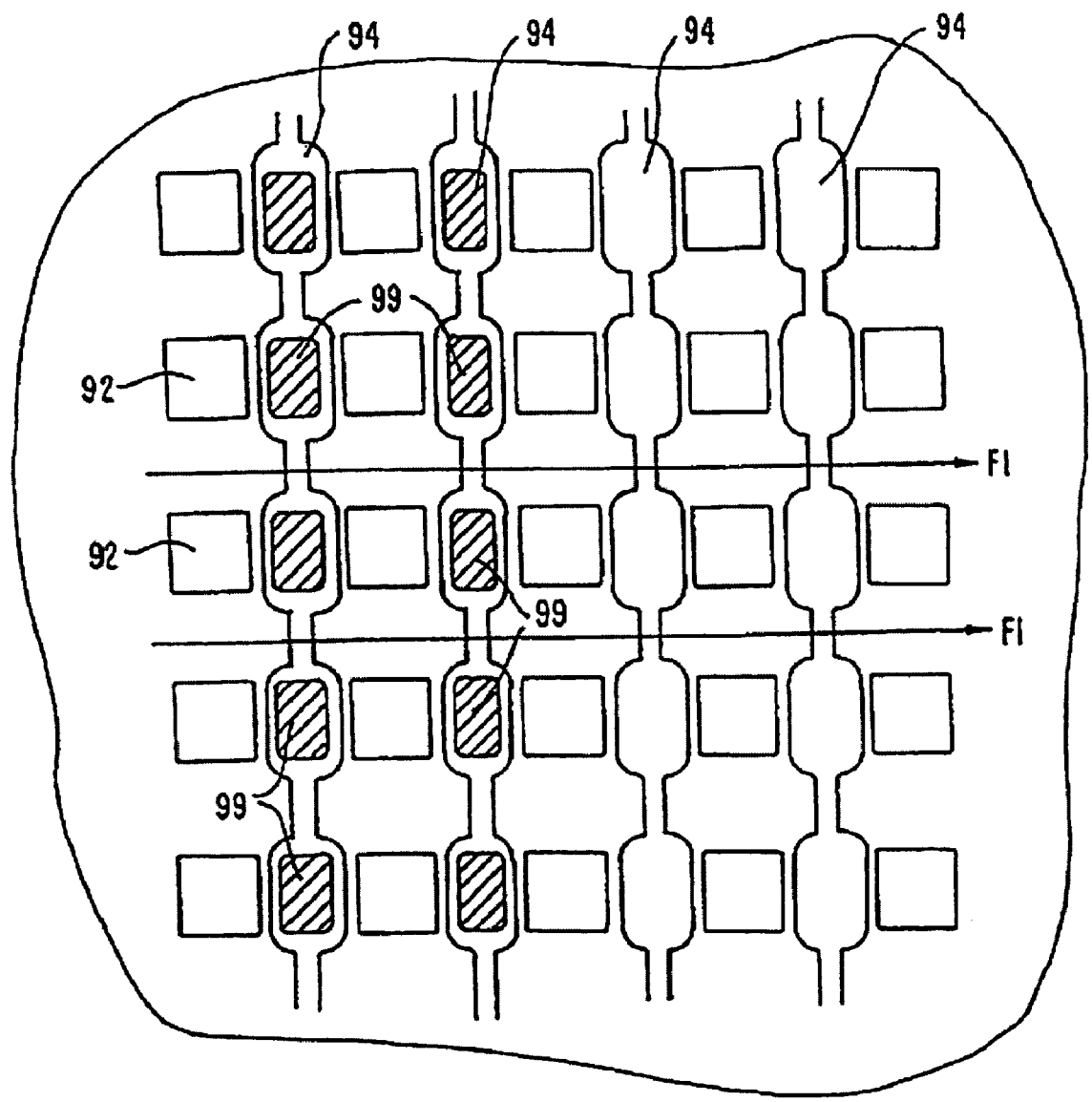
FIG. 27D also shows the alignment of the first layer of elastomer of FIG. 27A with the other set of control channels in the second layer of elastomer of FIG. 27B.

Elastomeric layer 95 is positioned over top of elastomeric layer 90 such that "vertical" control lines 96 are positioned over posts 92 as shown in FIG. 27C and "horizontal" control lines 94 are positioned with their wide portions between posts 92, as shown in FIG. 27D.

As can be seen in FIG. 27C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 27D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIG. 27 allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

11. Normally-Closed Valve Structure

FIGS. 14B and 14H above depict a valve structure in which the elastomeric membrane is moveable from a first relaxed position to a second actuated position in which the flow channel is blocked. However, the present invention is not limited to this particular valve configuration.

FIGS. 28A-28J show a variety of views of a normally-closed valve structure in which the elastomeric membrane is moveable from a first relaxed position blocking a flow channel, to a second actuated position in which the flow channel is open, utilizing a negative control pressure.

Figure 28A:
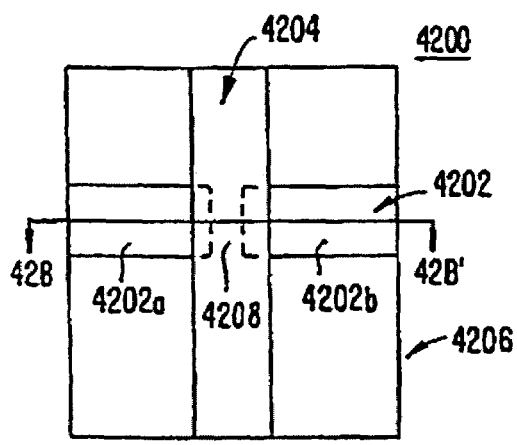
FIGS. 28A-28J show views of one embodiment of a normally-closed valve structure in accordance with the present invention.
Figure 28D:
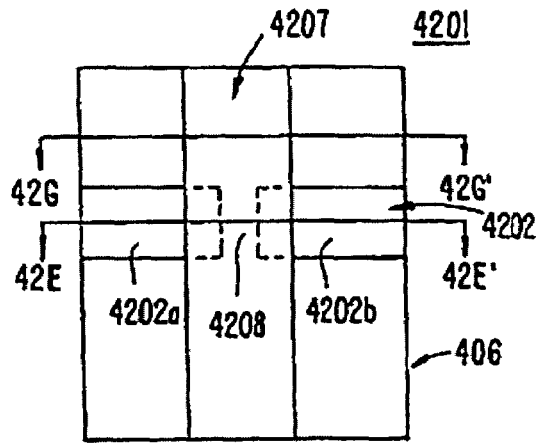
Figure 28B:
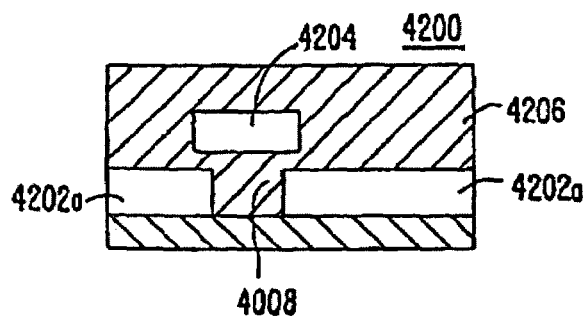
Figure 28E:
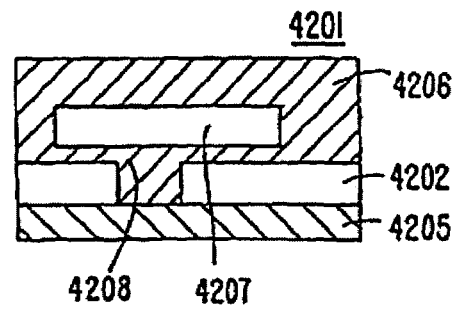

FIG. 28A shows a plan view, and FIG. 28B shows a cross sectional view along line 42B-42B', of normally-closed valve 4200 in an unactuated state. Flow channel 4202 and control channel 4204 are formed in elastomeric block 4206 overlying substrate 4205. Flow channel 4202 includes a first portion 4202a and a second portion 4202b separated by separating portion 4208. Control channel 4204 overlies separating portion 4208. As shown in FIG. 28B, in its relaxed, unactuated position, separating portion 4008 remains positioned between flow channel portions 4202a and 4202b, interrupting flow channel 4202.

Figure 28C:
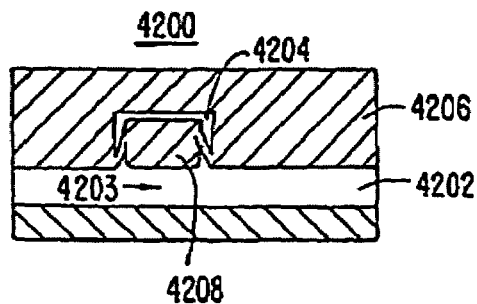
Figure 28F:
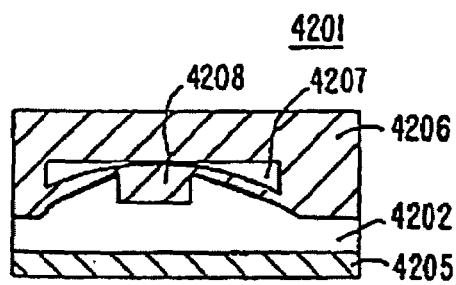

FIG. 28C shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force membrane 4208 projects into control channel 4204, thereby removing the obstacle to a flow of material through flow channel 4202 and creating a passageway 4203. Upon elevation of pressure within control channel 4204, separating portion 4208 will assume its natural position, relaxing back into and obstructing flow channel 4202.

The behavior of the membrane in response to an actuation force may be changed by varying the width of the overlying control channel. Accordingly, FIGS. 28D-28H show plan and cross-sectional views of an alternative embodiment of a normally-closed valve 4201 in which control channel 4207 is substantially wider than separating portion 4208. As shown in cross-sectional views FIG. 28E-F along line 42E-42E' of FIG. 28D, because a larger area of elastomeric material is required to be moved during actuation, the actuation force necessary to be applied is reduced.

Figure 28I:
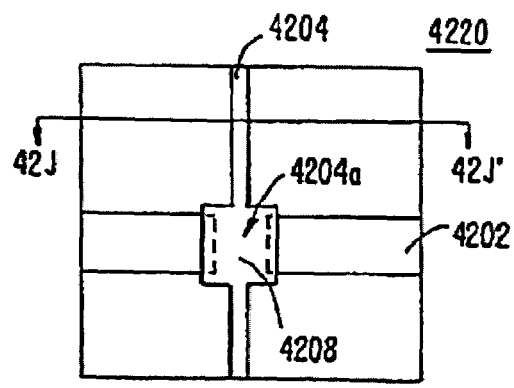
Figure 28G:
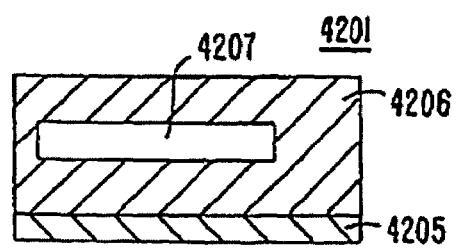

FIGS. 28G and H show a cross-sectional views along line 40G-40G' of FIG. 21D. In comparison with the unactuated valve configuration shown in FIG. 28G, FIG. 28H shows that reduced pressure within wider control channel 4207 may under certain circumstances have the unwanted effect of pulling underlying elastomer 4206 away from substrate 4205, thereby creating undesirable void 4212.

Figure 28J:
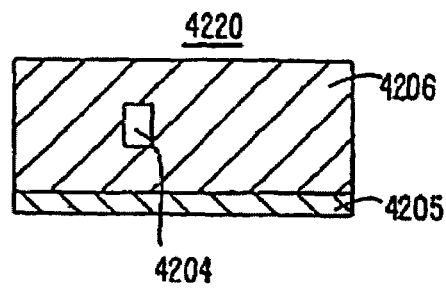
Figure 28H:
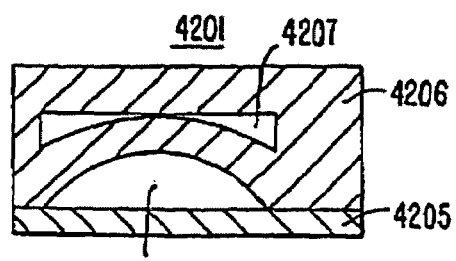

Accordingly, FIG. 28I shows a plan view, and FIG. 28J shows a cross-sectional view along line 21J-21J' of FIG. 28I, of valve structure 4220 which avoids this problem by featuring control line 4204 with a minimum width except in segment 4204a overlapping separating portion 4208. As shown in FIG. 28J, even under actuated conditions the narrower cross-section of control channel 4204 reduces the attractive force on the underlying elastomer material 4206, thereby preventing this elastomer material from being drawn away from substrate 4205 and creating an undesirable void.

While a normally-closed valve structure actuated in response to pressure is shown in FIGS. 28A-28J, a normally-closed valve in accordance with the present invention is not limited to this configuration. For example, the separating portion obstructing the flow channel could alternatively be manipulated by electric or magnetic fields, as described extensively above.

12. Side-Actuated Valve

Figure 29A:
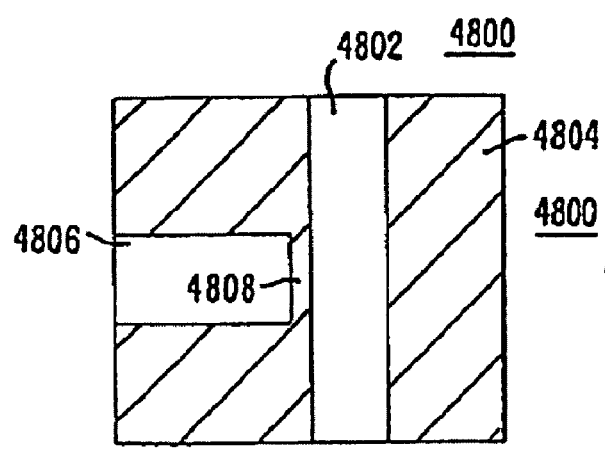
FIGS. 29A and 29B show plan views illustrating operation of one embodiment of a side-actuated valve structure in accordance with the present invention.
Figure 29B:
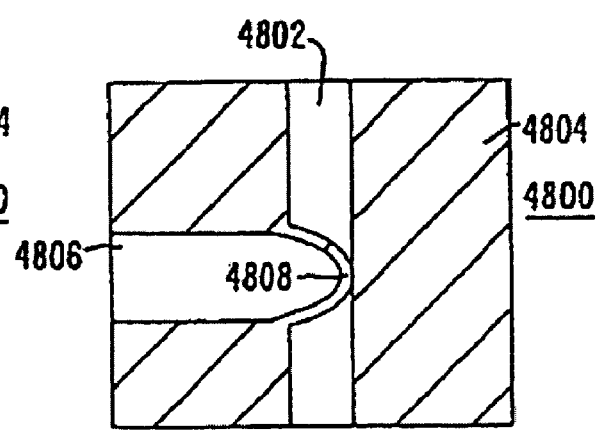

While the above description has focused upon microfabricated elastomeric valve structures in which a control channel is positioned above and separated by an intervening elastomeric membrane from an underlying flow channel, the present invention is not limited to this configuration. FIGS. 29A and 29B show plan views of one embodiment of a side-actuated valve structure in accordance with one embodiment of the present invention.

FIG. 29A shows side-actuated valve structure 4800 in an unactuated position. Flow channel 4802 is formed in elastomeric layer 4804. Control channel 4806 abutting flow channel 4802 is also formed in elastomeric layer 4804. Control channel 4806 is separated from flow channel 4802 by elastomeric membrane portion 4808. A second elastomeric layer (not shown) is bonded over bottom elastomeric layer 4804 to enclose flow channel 4802 and control channel 4806.

FIG. 29B shows side-actuated valve structure 4800 in an actuated position. In response to a build up of pressure within control channel 4806, membrane 4808 deforms into flow channel 4802, blocking flow channel 4802. Upon release of pressure within control channel 4806, membrane 4808 would relax back into control channel 4806 and open flow channel 4802.

While a side-actuated valve structure actuated in response to pressure is shown in FIGS. 29A and 29B, a side-actuated valve in accordance with the present invention is not limited to this configuration. For example, the elastomeric membrane portion located between the abutting flow and control channels could alternatively be manipulated by electric or magnetic fields, as described extensively above.

13. Composite Structures

Figure 30:
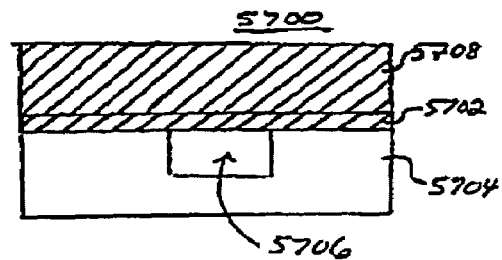
FIG. 30 shows a cross-sectional view of one embodiment of a composite structure in accordance with the present invention.

Microfabricated elastomeric structures of the present invention may be combined with non-elastomeric materials to create composite structures. FIG. 30 shows a cross-sectional view of one embodiment of a composite structure in accordance with the present invention. FIG. 30 shows composite valve structure 5700 including first, thin elastomer layer 5702 overlying semiconductor-type substrate 5704 having channel 5706 formed therein. Second, thicker elastomer layer 5708 overlies first elastomer layer 5702. Actuation of first elastomer layer 5702 to drive it into channel 5706, will cause composite structure 5700 to operate as a valve.

Figure 31:
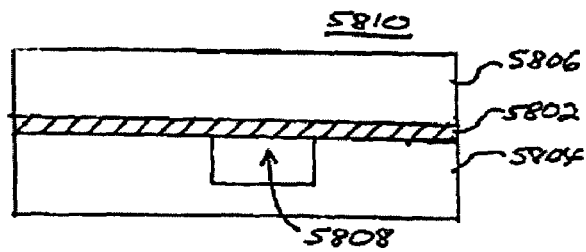
FIG. 31 shows a cross-sectional view of another embodiment of a composite structure in accordance with the present invention.

FIG. 31 shows a cross-sectional view of a variation on this theme, wherein thin elastomer layer 5802 is sandwiched between two hard, semiconductor substrates 5804 and 5806, with lower substrate 5804 featuring channel 5808. Again, actuation of thin elastomer layer 5802 to drive it into channel 5808 will cause composite structure 5810 to operate as a valve.

The structures shown in FIG. 30 or 31 may be fabricated utilizing either the multilayer soft lithography or encapsulation techniques described above. In the multilayer soft lithography method, the elastomer layer(s) would be formed and then placed over the semiconductor substrate bearing the channel. In the encapsulation method, the channel would be first formed in the semiconductor substrate, and then the channel would be filled with a sacrificial material such as photoresist. The elastomer would then be formed in place over the substrate, with removal of the sacrificial material producing the channel overlaid by the elastomer membrane. As is discussed in detail below in connection with bonding of elastomer to other types of materials, the encapsulation approach may result in a stronger seal between the elastomer membrane component and the underlying nonelastomer substrate component.

Figure 32:
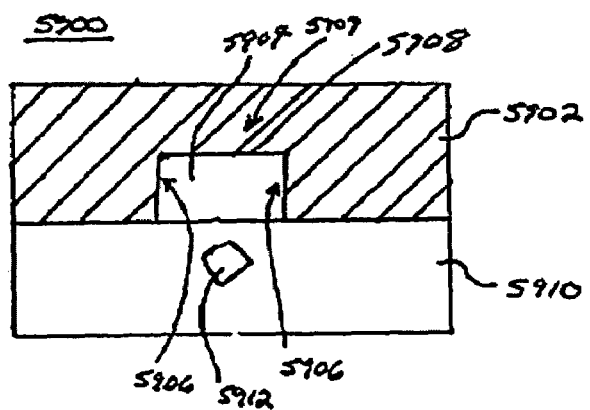
FIG. 32 shows a cross-sectional view of another embodiment of a composite structure in accordance with the present invention.

As shown in FIGS. 30 and 31, a composite structure in accordance with embodiments of the present invention may include a hard substrate that bears a passive feature such as a channels. However, the present invention is not limited to this approach, and the underlying hard substrate may bear active features that interact with an elastomer component bearing a recess. This is shown in FIG. 32, wherein composite structure 5900 includes elastomer component 5902 containing recess 5904 having walls 5906 and ceiling 5908. Ceiling 5908 forms flexible membrane portion 5909. Elastomer component 5902 is sealed against substantially planar nonelastomeric component 5910 that includes active device 5912. Active device 5912 may interact with material present in recess 5904 and/or flexible membrane portion 5909.

Many Types of active structures may be present in the nonelastomer substrate. Active structures that could be present in an underlying hard substrate include, but are not limited to, resistors, capacitors, photodiodes, transistors, chemical field effect transistors (chem FET's), amperometric/coulometric electrochemical sensors, fiber optics, fiber optic interconnects, light emitting diodes, laser diodes, vertical cavity surface emitting lasers (VCSEL's), micromirrors, accelerometers, pressure sensors, flow sensors, CMOS imaging arrays, CCD cameras, electronic logic, microprocessors, thermistors, Peltier coolers, waveguides, resistive heaters, chemical sensors, strain gauges, inductors, actuators (including electrostatic, magnetic, electromagnetic, bimetallic, piezoelectric, shape-memory-alloy based, and others), coils, magnets, electromagnets, magnetic sensors (such as those used in hard drives, superconducting quantum interference devices (SQUIDS) and other types), radio frequency sources and receivers, microwave frequency sources and receivers, sources and receivers for other regions of the electromagnetic spectrum, radioactive particle counters, and electrometers.

As is well known in the art, a vast variety of technologies can be utilized to fabricate active features in semiconductor and other types of hard substrates, including but not limited printed circuit board (PCB) technology, CMOS, surface micromachining, bulk micromachining, printable polymer electronics, and TFT and other amorphous/polycrystalline techniques as are employed to fabricate laptop and flat screen displays.

A variety of approaches can be employed to seal the elastomeric structure against the nonelastomeric substrate, ranging from the creation of a Van der Waals bond between the elastomeric and nonelastomeric components, to creation of covalent or ionic bonds between the elastomeric and nonelastomeric components of the composite structure. Example approaches to sealing the components together are discussed below, approximately in order of increasing strength.

A first approach is to rely upon the simple hermetic seal resulting from Van der Waals bonds formed when a substantially planar elastomer layer is placed into contact with a substantially planar layer of a harder, non-elastomer material. In one embodiment, bonding of RTV elastomer to a glass substrate created a composite structure capable of withstanding up to about 3-4 psi of pressure. This may be sufficient for many potential applications.

A second approach is to utilize a liquid layer to assist in bonding. One example of this involves bonding elastomer to a hard glass substrate, wherein a weakly acidic solution (5 µl HCl in $H_2O$, pH 2) was applied to a glass substrate. The elastomer component was then placed into contact with the glass substrate, and the composite structure baked at 37° C. to remove the water. This resulted in a bond between elastomer and non-elastomer able to withstand a pressure of about 20 psi. In this case, the acid may neutralize silanol groups present on the glass surface, permitting the elastomer and nonelastomer to enter into good Van der Waals contact with each other.

Exposure to ethanol can also cause device components to adhere together. In one embodiment, an RTV elastomer material and a glass substrate were washed with ethanol and then dried under Nitrogen. The RTV elastomer was then placed into contact with the glass and the combination baked for 3 hours at 80° C. Optionally, the RTV may also be exposed to a vacuum to remove any air bubbles trapped between the slide and the RTV. The strength of the adhesion between elastomer and glass using this method has withstood pressures in excess of 35 psi. The adhesion created using this method is not permanent, and the elastomer may be peeled off of the glass, washed, and resealed against the glass. This ethanol washing approach can also be employed used to cause successive layers of elastomer to bond together with sufficient strength to resist a pressure of 30 psi. In alternative embodiments, chemicals such as other alcohols or diols could be used to promote adhesion between layers.

An embodiment of a method of promoting adhesion between layers of a microfabricated structure in accordance with the present invention comprises exposing a surface of a first component layer to a chemical, exposing a surface of a second component layer to the chemical, and placing the surface of the first component layer into contact with the surface of the second elastomer layer.

A third approach is to create a covalent chemical bond between the elastomer component and functional groups introduced onto the surface of a nonelastomer component. Examples of derivitization of a nonelastomer substrate surface to produce such functional groups include exposing a glass substrate to agents such as vinyl silane or aminopropyltriethoxy silane (APTES), which may be useful to allow bonding of the glass to silicone elastomer and polyurethane elastomer materials, respectively.

A fourth approach is to create a covalent chemical bond between the elastomer component and a functional group native to the surface of the nonelastomer component. For example, RTV elastomer can be created with an excess of vinyl groups on its surface. These vinyl groups can be caused to react with corresponding functional groups present on the exterior of a hard substrate material, for example the Si—H bonds prevalent on the surface of a single crystal silicon substrate after removal of native oxide by etching. In this example, the strength of the bond created between the elastomer component and the nonelastomer component has been observed to exceed the materials strength of the elastomer components.

14. Cell Pen/Cell Cage

In yet a further application of the present invention, an elastomeric structure can be utilized to manipulate organisms or other biological material. FIGS. 33A-33D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 33C:
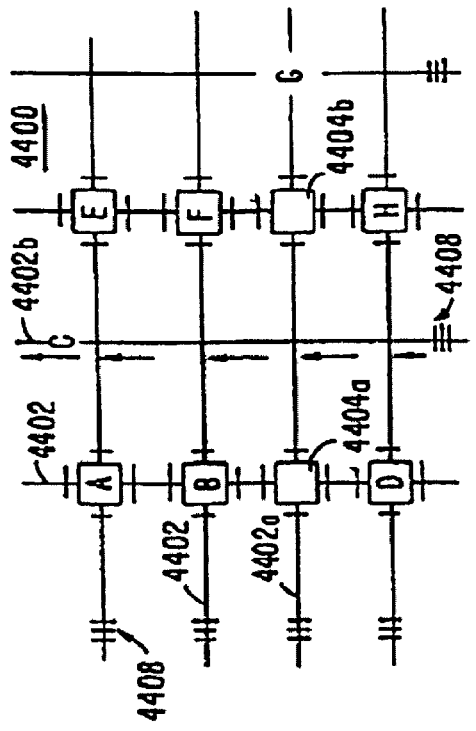
FIGS. 33A-33D show plan views illustrating operation of one embodiment of a cell pen structure in accordance with the present invention.
Figure 33D:
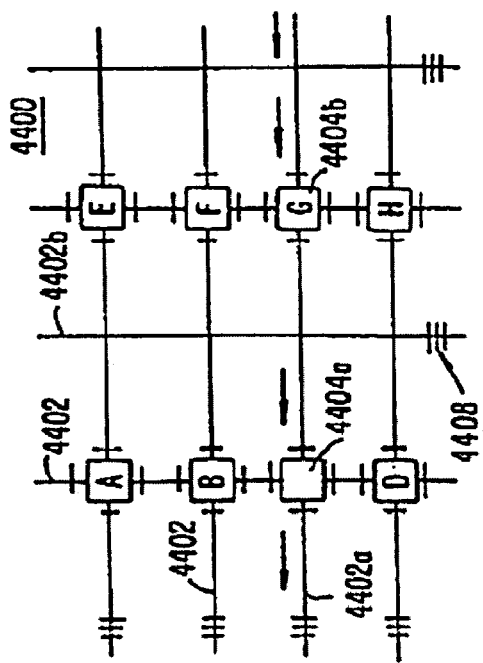
Figure 33A:
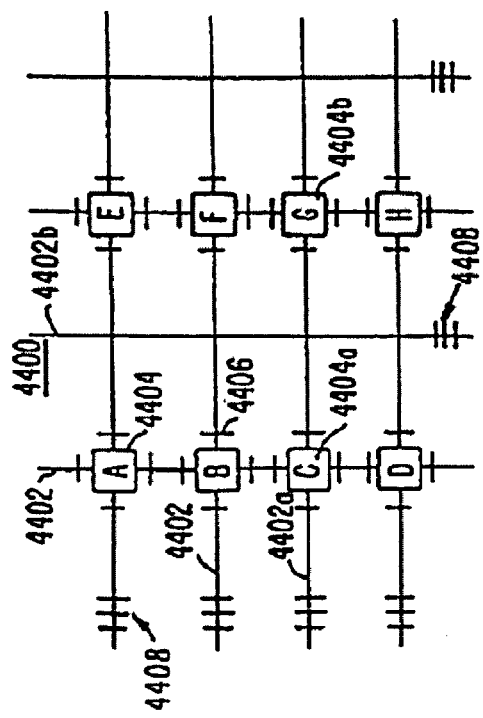
Figure 33B:
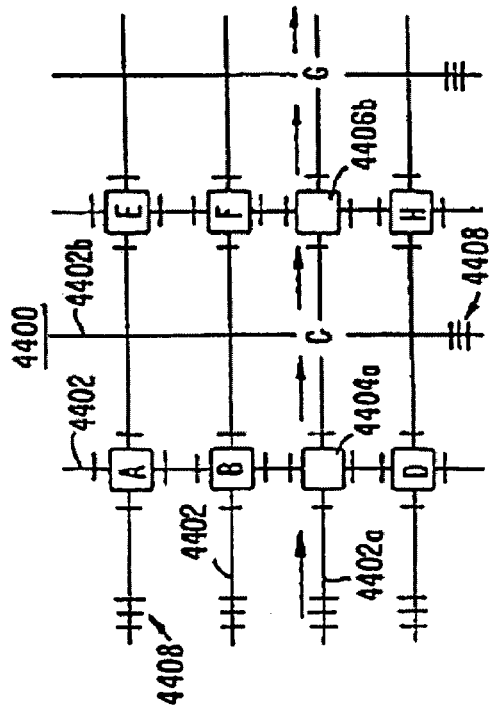

Cell pen array 4400 of FIG. 33A has been loaded with cells A-H that have been previously sorted. FIGS. 33B-33C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 33D shows that second cell G is moved back into its prior position in cell pen array 4400 by reversing the direction of liquid flow through horizontal flow channel 4402a.

Figure 34A:
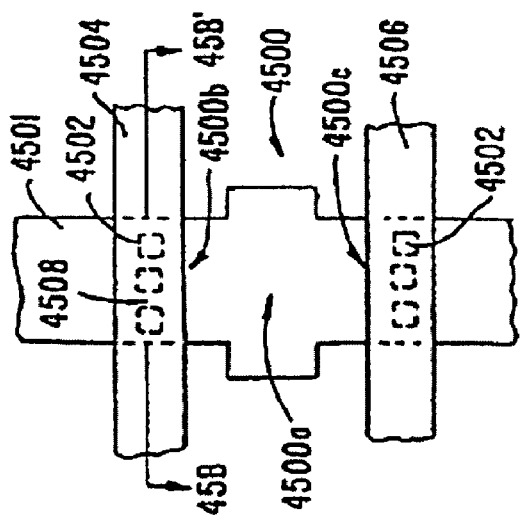
FIGS. 34A-34B show plan and cross-sectional views illustrating operation of one embodiment of a cell cage structure in accordance with the present invention.
Figure 34B:
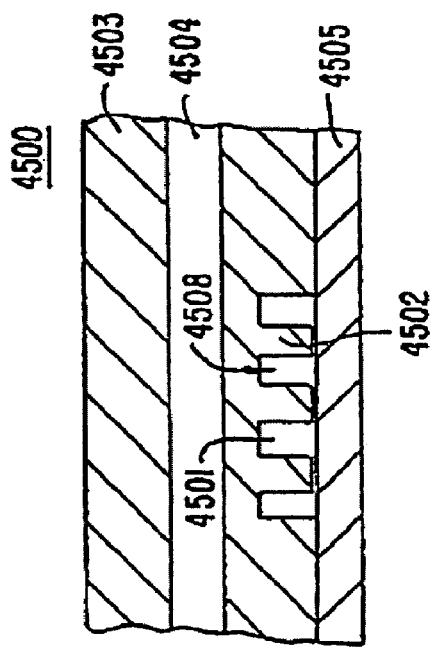

The cell pen array 4404 described above is capable of storing materials within a selected, addressable position for ready access. However, living organisms such as cells may require a continuous intake of foods and expulsion of wastes in order to remain viable. Accordingly, FIGS. 34A and 34B show plan and cross-sectional views (along line 45B-45B') respectively, of one embodiment of a cell cage structure in accordance with the present invention.

Cell cage 4500 is formed as an enlarged portion 4500a of a flow channel 4501 in an elastomeric block 4503 in contact with substrate 4505. Cell cage 4500 is similar to an individual cell pen as described above in FIGS. 33A-33D, except that ends 4500b and 4500c of cell cage 4500 do not completely enclose interior region 4500a. Rather, ends 4500a and 4500b of cage 4500 are formed by a plurality of retractable pillars 4502. Pillars 4502 may be part of a membrane structure of a nornally-closed valve structure as described extensively above in connection with FIGS. 28A-28J.

Specifically, control channel 4504 overlies pillars 4502. When the pressure in control channel 4504 is reduced, elastomeric pillars 4502 are drawn upward into control channel 4504, thereby opening end 4500b of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500a in order to sustain cell(s) stored therein. Pillars 4502 on opposite end 4500c are similarly configured beneath second control channel 4506 to permit opening of the cage and removal of the cell as desired.

The cross-flow channel architecture illustrated shown in FIGS. 33A-33D can be used to perform functions other than the cell pen just described. For example, the cross-flow channel architecture can be utilized in mixing applications.

Figure 35A:
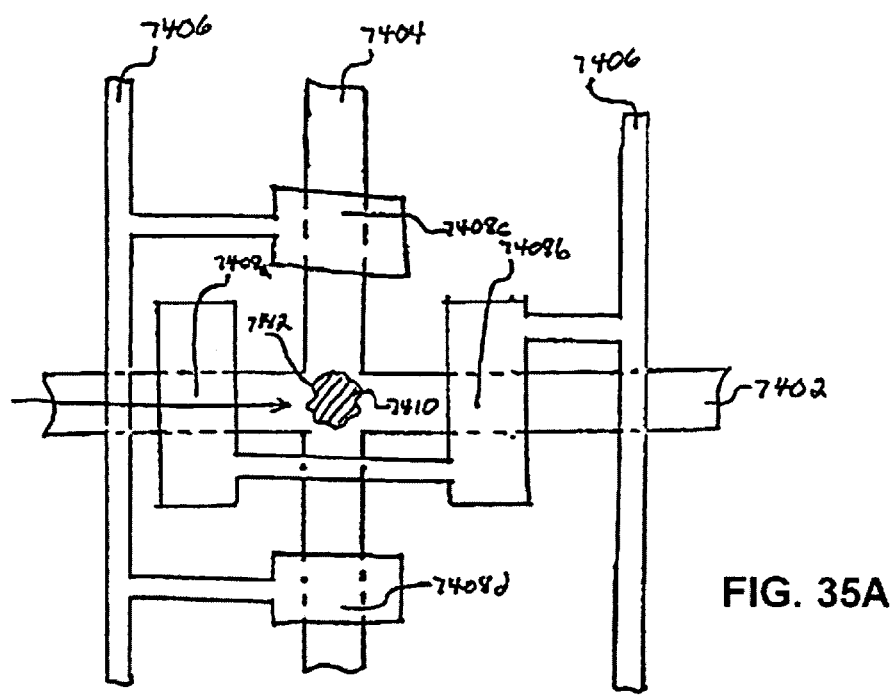
FIGS. 35A-35B show plan views of operation of a wiring structure utilizing cross-channel injection in accordance with the embodiment of the present invention.
Figure 35B:
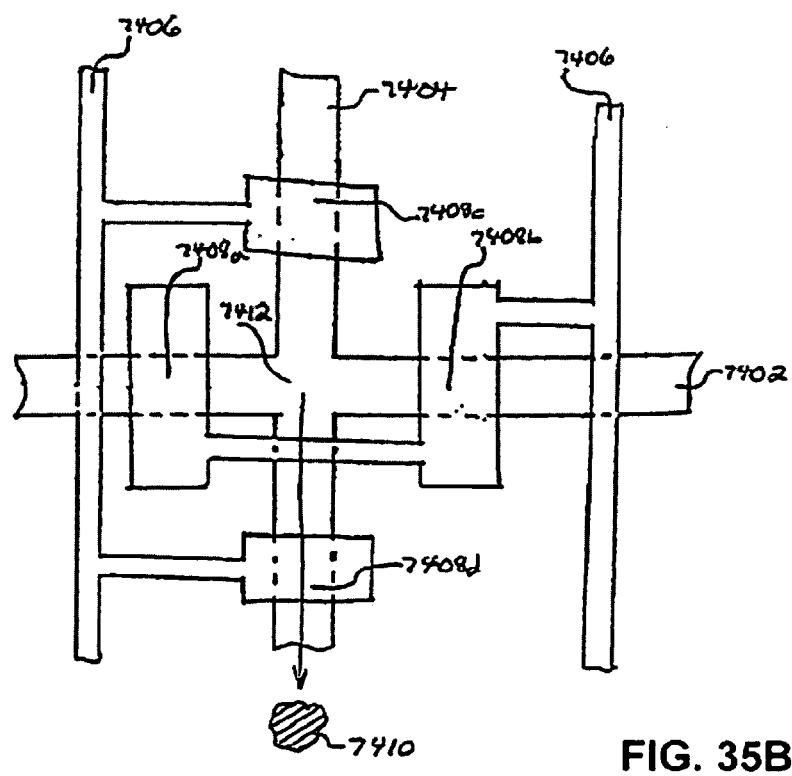

This is shown in FIGS. 35A-B, which illustrate a plan view of mixing steps performed by a microfabricated structure in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

As shown in FIG. 35A, valve pair 7408a-b is initially opened while valve pair 7408c-d is closed, and fluid sample 7410 is flowed to intersection 7412 through flow channel 7402. Valve pair 7408c-d is then actuated, trapping fluid sample 7410 at intersection 7412.

Next, as shown in FIG. 35B, valve pairs 7408a-b and 7408c-d are opened, such that fluid sample 7410 is injected from intersection 7412 into flow channel 7404 bearing a cross-flow of fluid. The process shown in FIGS. 35A-B can be repeated to accurately dispense any number of fluid samples down cross-flow channel 7404.

While the embodiment shown and described above in connection with FIGS. 35A-35B utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

15. Metering by Volume Exclusion

Many high throughput screening and diagnostic applications call for accurate combination and of different reagents in a reaction chamber. Given that it is frequently necessary to prime the channels of a microfluidic device in order to ensure fluid flow, it may be difficult to ensure mixed solutions do not become diluted or contaminated by the contents of the reaction chamber prior to sample introduction.

Volume exclusion is one technique enabling precise metering of the introduction of fluids into a reaction chamber. In this approach, a reaction chamber may be completely or partially emptied prior to sample injection. This method reduces contamination from residual contents of the chamber contents, and may be used to accurately meter the introduction of solutions in a reaction chamber.

Figure 36A:
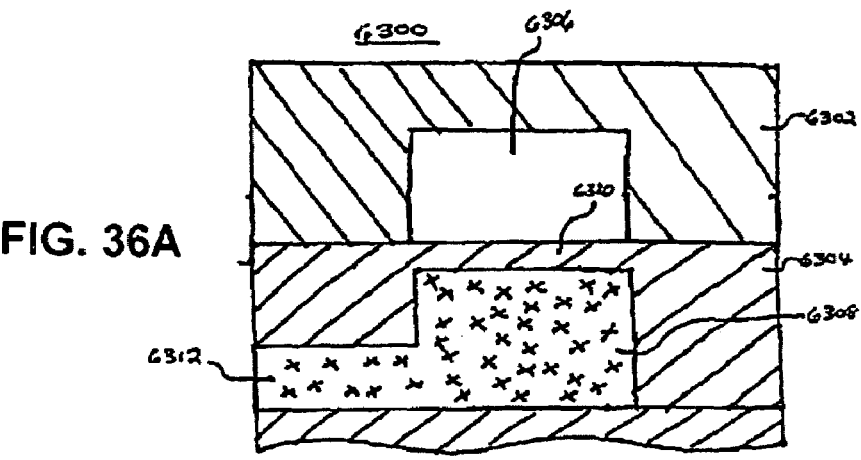
FIGS. 36A-36D illustrate cross-sectional views of metering by volume exclusion in accordance with an embodiment of the present invention.

Specifically, FIGS. 36A-36D show cross-sectional views of a reaction chamber in which volume exclusion is employed to meter reactants. FIG. 36A shows a cross-sectional view of portion 6300 of a microfluidic device comprising first elastomer layer 6302 overlying second elastomer layer 6304. First elastomer layer 6302 includes control chamber 6306 in fluid communication with a control channel (not shown). Control chamber 6306 overlies and is separated from dead-end reaction chamber 6308 of second elastomer layer 6304 by membrane 6310. Second elastomer layer 6304 further comprises flow channel 6312 leading to dead-end reaction chamber 6308.

Figure 36B:
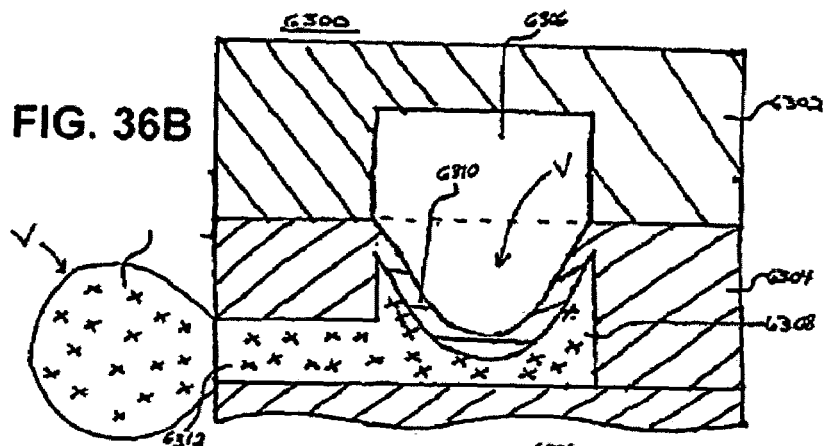

FIG. 36B shows the result of a pressure increase within control chamber 6306. Specifically, increased control chamber pressure causes membrane 6310 to flex downward into reaction chamber 6308, reducing by volume V the effective volume of reaction chamber 6308. This in turn excludes an equivalent volume V of reactant from reaction chamber 6308, such that volume V of first reactant X is output from flow channel 6312. The exact correlation between a pressure increase in control chamber 6306 and the volume of material output from flow channel 6312 can be precisely calibrated.

Figure 36C:
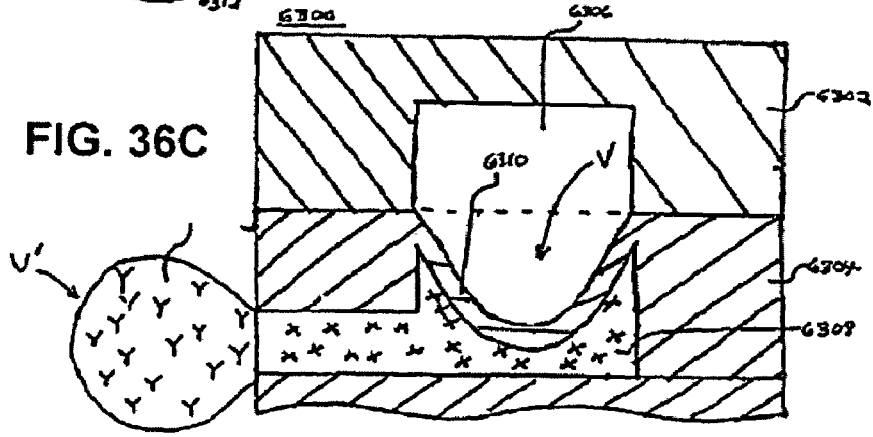

As shown in FIG. 36C, while elevated pressure is maintained within control chamber 6306, volume V' of second reactant Y is placed into contact with flow channel 6312 and reaction chamber 6308.

Figure 36D:
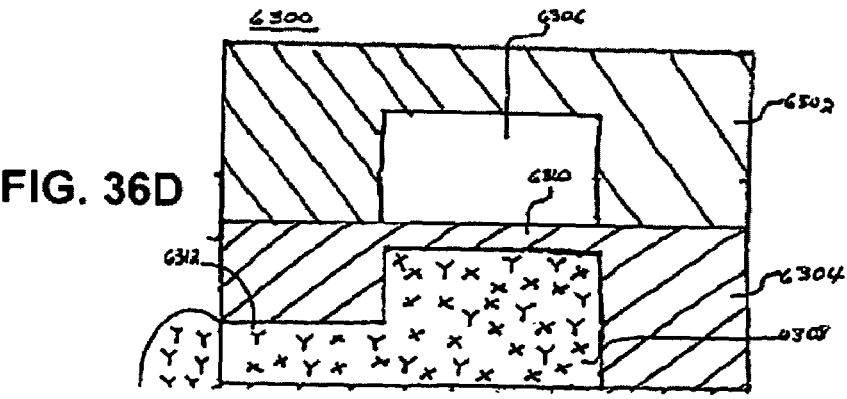

In the next step shown in FIG. 36D, pressure within control chamber 6306 is reduced to original levels. As a result, membrane 6310 relaxes and the effective volume of reaction chamber 6308 increases. Volume V of second reactant Y is sucked into the device. By varying the relative size of the reaction and control chambers, it is possible to accurately mix solutions at a specified relative concentration. It is worth noting that the amount of the second reactant Y that is sucked into the device is solely dependent upon the excluded volume V, and is independent of volume V' of Y made available at the opening of the flow channel.

While FIGS. 36A-36D show a simple embodiment of the present invention involving a single reaction chamber, in more complex embodiments parallel structures of hundreds or thousands of reaction chambers could be actuated by a pressure increase in a single control line.

Moreover, while the above description illustrates two reactants being combined at a relative concentration that fixed by the size of the control and reaction chambers, a volume exclusion technique could be employed to combine several reagents at variable concentrations in a single reaction chamber. One possible approach is to use several, separately addressable control chambers above each reaction chamber. An example of this architecture would be to have ten separate control lines instead of a single control chamber, allowing ten equivalent volumes to be pushed out or sucked in.

Another possible approach would utilize a single control chamber overlying the entire reaction chamber, with the effective volume of the reaction chamber modulated by varying the control chamber pressure. In this manner, analog control over the effective volume of the reaction chamber is possible. Analog volume control would in turn permit the combination of many solutions reactants at arbitrary relative concentrations.

An embodiment of a method of metering a volume of fluid in accordance with the present invention comprises providing a chamber having a volume in an elastomeric block separated from a control recess by an elastomeric membrane, and supplying a pressure to the control recess such that the membrane is deflected into the chamber and the volume is reduced by a calibrated amount, thereby excluding from the chamber the calibrated volume of fluid.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used herein and in the appended claims, the singular forms "a", "and", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A chemostat chip comprising one or more chemostats, wherein each of the chemostats includes a first compartment adaptable to hold one or more cells and a second compartment adaptable to receive a lysis agent, and wherein the first and second compartments are separated by an actuatable valve that when opened can permit the one or more cells to travel from the first compartment to the second compartment, and when closed can isolate the one or more cells in the second compartment before exposing the second compartment to the lysis agent, wherein said chemostat chip further comprises a growth chamber having a plurality of compartments;

wherein each of the compartments may be fluidly isolated from the rest of the growth chamber by one or more actuatable valves;

wherein the compartments of the growth chamber are connected in a loop;

a nutrient supply-line to supply growth medium to the growth chamber; and an output port to remove fluids from the growth chamber.

2. The chemostat chip of claim 1, wherein an actuatable supply valve controls the delivery of the lysis agent to the compartment coupled to the supply channel.

3. The chemostat chip of claim 1, wherein the second compartment is fluidly coupled to an output channel to remove materials from the compartment.

4. The chemostat chip of claim 1, wherein the growth chamber comprises a silicone elastomer.

5. The chemostat chip of claim 1, wherein the chemostat comprises a peristaltic pump to circulate fluids in the growth chamber.

6. The chemostat chip of claim 1, wherein the growth chamber comprises a volume of about 50 nanoliters or less.

7. The chemostat chip of claim 1, wherein the growth chamber comprises a volume of about 16 nanoliters or less.

8. The chemostat chip of claim 1, wherein the growth chamber has 16 compartments.

9. The chemostat chip of claim 1, wherein during operation the chemostat chip consumes growth medium at a rate of about 40 µL/day or less.

10. The chemostat chip of claim 3, wherein the materials removed from the compartment comprise dissolved cell components.

11. The chemostat chip of claim 3, wherein an actuatable output valve controls the removal of the materials from the compartment.

12. The chemostat chip of claim 4, wherein the silicone elastomer is polydimethylsiloxane.

13. A chemostat chip comprising an array of chemostats, wherein each of the chemostats comprises:

a growth chamber having a plurality of compartments, wherein each of the compartments may be fluidly isolated from the rest of the growth chamber by one or more actuatable valves to give the growth chamber a variable volume;

a nutrient supply-line to supply growth medium to the growth chamber; and an output port to remove fluids from the growth chamber.

14. The chemostat chip of claim 13, wherein the chip comprises six or more chemostats.

15. The chemostat chip of claim 13, wherein the chip has a thickness of about 5 mm or less.

* * * * *